US009173604B2

(12) United States Patent
Yamanaka et al.

(10) Patent No.: US 9,173,604 B2
(45) Date of Patent: Nov. 3, 2015

(54) MEASUREMENT DEVICE, MEASUREMENT METHOD, MEASUREMENT RESULT PROCESSING DEVICE, MEASUREMENT SYSTEM, MEASUREMENT RESULT PROCESSING METHOD, CONTROL PROGRAM, AND RECORDING MEDIUM

(75) Inventors: Mikihiro Yamanaka, Osaka (JP); Megumi Hijikuro, Osaka (JP); Keita Hara, Osaka (JP)

(73) Assignee: SHARP KABUSHIKI KAISHA, Osaka (JP)

( * ) Notice: Subject to any disclaimer, the term of this patent is extended or adjusted under 35 U.S.C. 154(b) by 443 days.

(21) Appl. No.: 13/635,629

(22) PCT Filed: Nov. 17, 2010

(86) PCT No.: PCT/JP2010/070501
§ 371 (c)(1),
(2), (4) Date: Oct. 5, 2012

(87) PCT Pub. No.: WO2011/114578
PCT Pub. Date: Sep. 22, 2011

(65) Prior Publication Data
US 2013/0030306 A1 Jan. 31, 2013

(30) Foreign Application Priority Data

Mar. 19, 2010 (JP) ................................. 2010-064572
Apr. 6, 2010 (JP) ................................. 2010-088070

(51) Int. Cl.
*A61B 6/00* (2006.01)
*A61B 5/1455* (2006.01)
(Continued)

(52) U.S. Cl.
CPC ............. *A61B 5/1455* (2013.01); *A61B 5/0071* (2013.01); *A61B 5/14546* (2013.01); *A61B 5/743* (2013.01); *A61B 5/489* (2013.01); *A61B 5/6824* (2013.01); *A61B 5/6835* (2013.01); *A61B 2562/185* (2013.01)

(58) Field of Classification Search
CPC combination set(s) only.
See application file for complete search history.

(56) References Cited

U.S. PATENT DOCUMENTS

| 5,624,804 A | 4/1997 | Bucala |
| 5,629,408 A | 5/1997 | Bucala |
| 5,655,530 A | 8/1997 | Messerschmidt |

(Continued)

FOREIGN PATENT DOCUMENTS

| JP | 2-203255 A | 8/1990 |
| JP | 7-502534 A | 3/1995 |

(Continued)

OTHER PUBLICATIONS

"NEMOes, a new method to evaluate early atherosclerosis in rodent model", Hirotaka Watada Ryuzo Kawamori, Department of Medicine, Metabolism & Endocrinology, Juntendo University School of Medicine (Nov. 1, 2006) vol. 64, No. 11, pp. 2165-2175.

(Continued)

*Primary Examiner* — Long V Le
*Assistant Examiner* — Farshad Negarestan
(74) *Attorney, Agent, or Firm* — Birch, Stewart, Kolasch & Birch, LLP

(57) ABSTRACT

A measurement device (1) includes a probe (7) which irradiates a specific part or a specific location of a living body with excitation light and which receives fluorescence generated by irradiating the specific part or the specific location with excitation light.

8 Claims, 26 Drawing Sheets

(51) Int. Cl.
*A61B 5/145* (2006.01)
*A61B 5/00* (2006.01)

(56) References Cited

U.S. PATENT DOCUMENTS

| | | |
|---|---|---|
| 5,683,887 A | 11/1997 | Bucala |
| 5,702,704 A | 12/1997 | Bucala |
| 5,712,101 A | 1/1998 | Bucala |
| 5,733,546 A | 3/1998 | Bucala |
| 5,823,951 A | 10/1998 | Messerschmidt |
| 6,061,583 A | 5/2000 | Ishihara et al. |
| 6,070,093 A | 5/2000 | Oosta et al. |
| 6,094,300 A | 7/2000 | Kashima et al. |
| 6,115,673 A | 9/2000 | Malin et al. |
| 6,152,876 A | 11/2000 | Robinson et al. |
| 6,212,424 B1 | 4/2001 | Robinson |
| 6,240,306 B1 | 5/2001 | Rohrscheib et al. |
| 6,292,686 B1 | 9/2001 | Chaiken et al. |
| 6,349,227 B1 | 2/2002 | Numada |
| 6,389,306 B1 | 5/2002 | Chaiken et al. |
| 6,411,373 B1 | 6/2002 | Garside et al. |
| 6,415,167 B1 | 7/2002 | Blank et al. |
| 6,505,059 B1 | 1/2003 | Kollias et al. |
| 6,534,012 B1 | 3/2003 | Hazen et al. |
| 6,567,678 B1 | 5/2003 | Oosta et al. |
| 6,622,032 B1 | 9/2003 | Robinson et al. |
| 6,865,408 B1 | 3/2005 | Abbink et al. |
| 6,871,169 B1 | 3/2005 | Hazen et al. |
| 2001/0018560 A1 | 8/2001 | Robinson |
| 2002/0016534 A1* | 2/2002 | Trepagnier et al. ............ 600/316 |
| 2002/0035341 A1 | 3/2002 | Rohrscheib et al. |
| 2002/0038080 A1 | 3/2002 | Makarewicz et al. |
| 2002/0082487 A1 | 6/2002 | Kollias et al. |
| 2002/0091324 A1 | 7/2002 | Kollias et al. |
| 2002/0099278 A1 | 7/2002 | Makarewicz et al. |
| 2002/0174318 A1 | 11/2002 | Stuttard et al. |
| 2003/0007147 A1 | 1/2003 | Johnson |
| 2003/0023152 A1 | 1/2003 | Abbink et al. |
| 2003/0023170 A1 | 1/2003 | Gardner et al. |
| 2003/0069484 A1 | 4/2003 | Blank et al. |
| 2003/0152947 A1 | 8/2003 | Crossman et al. |
| 2003/0191378 A1 | 10/2003 | Davis, III et al. |
| 2003/0208111 A1 | 11/2003 | Mattu et al. |
| 2003/0216627 A1 | 11/2003 | Lorenz et al. |
| 2004/0024553 A1 | 2/2004 | Monfre et al. |
| 2004/0039271 A1 | 2/2004 | Blank et al. |
| 2004/0068163 A1 | 4/2004 | Ruchti et al. |
| 2004/0082070 A1 | 4/2004 | Jones et al. |
| 2004/0127777 A1 | 7/2004 | Ruchti et al. |
| 2004/0167382 A1 | 8/2004 | Gardner et al. |
| 2004/0215066 A1 | 10/2004 | Huang et al. |
| 2004/0235161 A1* | 11/2004 | Tabata et al. .................. 435/371 |
| 2004/0239461 A1 | 12/2004 | Kincaid et al. |
| 2004/0267105 A1 | 12/2004 | Monfre et al. |
| 2005/0010090 A1 | 1/2005 | Acosta et al. |
| 2005/0014997 A1 | 1/2005 | Ruchti et al. |
| 2005/0020892 A1 | 1/2005 | Acosta et al. |
| 2005/0049466 A1 | 3/2005 | Blank et al. |
| 2005/0054908 A1 | 3/2005 | Blank et al. |
| 2005/0090750 A1 | 4/2005 | Ediger et al. |
| 2005/0107676 A1 | 5/2005 | Acosta et al. |
| 2005/0119541 A1 | 6/2005 | Lorenz et al. |
| 2005/0148834 A1 | 7/2005 | Hull et al. |
| 2005/0149300 A1 | 7/2005 | Ruchti et al. |
| 2005/0159656 A1 | 7/2005 | Hockersmith et al. |
| 2005/0187439 A1 | 8/2005 | Blank et al. |
| 2005/0196821 A1 | 9/2005 | Monfre et al. |
| 2005/0203358 A1 | 9/2005 | Monfre et al. |
| 2005/0203359 A1 | 9/2005 | Blank et al. |
| 2005/0203364 A1 | 9/2005 | Monfre et al. |
| 2005/0209514 A1 | 9/2005 | Oshima et al. |
| 2005/0209515 A1 | 9/2005 | Hockersmith et al. |
| 2005/0211872 A1 | 9/2005 | Kawano et al. |
| 2005/0240090 A1 | 10/2005 | Ruchti et al. |
| 2005/0261560 A1 | 11/2005 | Ridder et al. |
| 2005/0267341 A1 | 12/2005 | Blank et al. |
| 2005/0267342 A1 | 12/2005 | Blank et al. |
| 2006/0116562 A1 | 6/2006 | Acosta et al. |
| 2006/0167349 A1 | 7/2006 | Gardner et al. |
| 2006/0173254 A1 | 8/2006 | Acosta et al. |
| 2006/0173255 A1 | 8/2006 | Acosta et al. |
| 2006/0173256 A1 | 8/2006 | Ridder et al. |
| 2006/0178570 A1 | 8/2006 | Robinson et al. |
| 2006/0183983 A1 | 8/2006 | Acosta et al. |
| 2006/0195022 A1 | 8/2006 | Trepangnier et al. |
| 2006/0195023 A1 | 8/2006 | Acosta et al. |
| 2006/0200017 A1 | 9/2006 | Monfre et al. |
| 2006/0206018 A1 | 9/2006 | Abul-Haj et al. |
| 2006/0211927 A1 | 9/2006 | Acosta et al. |
| 2006/0211928 A1 | 9/2006 | Hull et al. |
| 2006/0211931 A1 | 9/2006 | Blank et al. |
| 2006/0217602 A1 | 9/2006 | Abul-Haj et al. |
| 2006/0244186 A1 | 11/2006 | Wells |
| 2007/0038046 A1 | 2/2007 | Hayter |
| 2007/0038116 A1 | 2/2007 | Yamanaka et al. |
| 2007/0053940 A1 | 3/2007 | Huang et al. |
| 2007/0073118 A1 | 3/2007 | Ridder et al. |
| 2007/0088205 A1 | 4/2007 | Hull et al. |
| 2007/0142720 A1 | 6/2007 | Ridder et al. |
| 2007/0142727 A1 | 6/2007 | Zhang et al. |
| 2007/0149868 A1 | 6/2007 | Blank et al. |
| 2007/0179367 A1 | 8/2007 | Ruchti et al. |
| 2007/0193879 A1 | 8/2007 | Prengaman et al. |
| 2007/0197880 A1 | 8/2007 | Maynard et al. |
| 2007/0226458 A1 | 9/2007 | Stuttard et al. |
| 2007/0234300 A1 | 10/2007 | Leake et al. |
| 2007/0242074 A1 | 10/2007 | Stuttard et al. |
| 2007/0245123 A1 | 10/2007 | Stuttard et al. |
| 2007/0245130 A1 | 10/2007 | Stuttard et al. |
| 2007/0245132 A1 | 10/2007 | Stuttard et al. |
| 2007/0265532 A1 | 11/2007 | Maynard et al. |
| 2007/0276199 A1 | 11/2007 | Ediger et al. |
| 2007/0293743 A1 | 12/2007 | Monfre et al. |
| 2007/0293744 A1 | 12/2007 | Monfre et al. |
| 2007/0294510 A1 | 12/2007 | Stuttard et al. |
| 2008/0007562 A1 | 1/2008 | Stuttard et al. |
| 2008/0008393 A1 | 1/2008 | Stuttard et al. |
| 2008/0010436 A1 | 1/2008 | Stuttard et al. |
| 2008/0016318 A1 | 1/2008 | Stuttard et al. |
| 2008/0028184 A1 | 1/2008 | Stuttard et al. |
| 2008/0033275 A1 | 2/2008 | Blank et al. |
| 2008/0034185 A1 | 2/2008 | Stuttard et al. |
| 2008/0034186 A1 | 2/2008 | Stuttard et al. |
| 2008/0040575 A1 | 2/2008 | Stuttard et al. |
| 2008/0052492 A1 | 2/2008 | Stuttard et al. |
| 2008/0097174 A1 | 4/2008 | Maynard et al. |
| 2008/0098201 A1 | 4/2008 | Stuttard et al. |
| 2008/0103373 A1 | 5/2008 | Matter et al. |
| 2008/0103396 A1 | 5/2008 | Johnson et al. |
| 2008/0132793 A1 | 6/2008 | Kollias et al. |
| 2008/0146899 A1 | 6/2008 | Ruchti et al. |
| 2008/0162874 A1 | 7/2008 | Stuttard et al. |
| 2008/0162875 A1 | 7/2008 | Stuttard et al. |
| 2008/0184017 A1 | 7/2008 | Stuttard et al. |
| 2008/0199865 A1 | 8/2008 | Crossman et al. |
| 2008/0208018 A1 | 8/2008 | Ridder et al. |
| 2008/0221066 A1 | 9/2008 | Holmberg et al. |
| 2008/0319286 A1 | 12/2008 | Ridder et al. |
| 2008/0319299 A1 | 12/2008 | Stippick et al. |
| 2008/0319382 A1 | 12/2008 | Blank et al. |
| 2009/0003764 A1 | 1/2009 | Ridder et al. |
| 2009/0018415 A1 | 1/2009 | Robinson et al. |
| 2009/0041567 A1 | 2/2009 | Wells |
| 2009/0198898 A1 | 8/2009 | Stuttard et al. |
| 2009/0228683 A1 | 9/2009 | Stuttard et al. |
| 2009/0234204 A1 | 9/2009 | Ridder et al. |
| 2009/0247840 A1 | 10/2009 | Blank et al. |
| 2009/0318786 A1 | 12/2009 | Blank et al. |
| 2010/0010325 A1 | 1/2010 | Ridder et al. |
| 2010/0286529 A1 | 11/2010 | Carroll et al. |
| 2011/0178397 A1 | 7/2011 | Bahner |
| 2011/0178420 A1 | 7/2011 | Ridder et al. |
| 2011/0184260 A1 | 7/2011 | Robinson et al. |
| 2011/0270092 A1 | 11/2011 | Kang et al. |

(56) References Cited

U.S. PATENT DOCUMENTS

| | | |
|---|---|---|
| 2011/0282167 A1 | 11/2011 | Ridder et al. |
| 2012/0065484 A1 | 3/2012 | Hull et al. |
| 2012/0078075 A1 | 3/2012 | Maynard et al. |
| 2012/0078473 A1 | 3/2012 | Ridder et al. |

FOREIGN PATENT DOCUMENTS

| | | |
|---|---|---|
| JP | 8-117209 A | 5/1996 |
| JP | 8-252246 A | 10/1996 |
| JP | 10-10049 A | 1/1998 |
| JP | 10-206742 A | 8/1998 |
| JP | 11-231227 A | 8/1999 |
| JP | 2000-189391 A | 7/2000 |
| JP | 2000-329696 A | 11/2000 |
| JP | 2001-59814 | 3/2001 |
| JP | 2001-87249 A | 4/2001 |
| JP | 2001-524342 A | 12/2001 |
| JP | 2002-510515 A | 4/2002 |
| JP | 2002-512830 A | 5/2002 |
| JP | 2002-291722 A | 10/2002 |
| JP | 2003-52699 A | 2/2003 |
| JP | 2005-500032 A | 1/2005 |
| JP | 2005-49238 A | 2/2005 |
| JP | 2005-185575 A | 7/2005 |
| JP | 2005-296635 A | 10/2005 |
| JP | 2005-301065 A | 10/2005 |
| JP | 2006-98340 A | 4/2006 |
| JP | 2006-102191 A | 4/2006 |
| JP | 2006-132995 A | 5/2006 |
| JP | 2006-235423 A | 9/2006 |
| JP | 2006-524544 A | 11/2006 |
| JP | 2007-44512 A | 2/2007 |
| JP | 2007-510159 A | 4/2007 |
| JP | 2007-222669 A | 9/2007 |
| JP | 2008-32703 A | 2/2008 |
| JP | 2008-51772 A | 3/2008 |
| JP | 2008-125989 A | 6/2008 |
| JP | 2008-531133 A | 8/2008 |
| JP | 2009-8460 A | 1/2009 |
| JP | 2009-47540 A | 3/2009 |
| JP | 2009-519779 A | 5/2009 |
| JP | 2010-2380 A | 1/2010 |
| JP | 2010-19579 A | 1/2010 |
| WO | WO 97/24066 A1 | 7/1997 |
| WO | WO 2008/107471 A2 | 9/2008 |

OTHER PUBLICATIONS

"Pathognostic Image Pattern of a Spectrum of Photosensitizers", Applied Physics (Oyou Butsuri), vol. 70, No. 6, p. 666-671 (Jun. 10, 2001), Katsuo Aizawa.

U.S. Office Action for U.S. Appl. No. 13/499,226, dated Jun. 26, 2014.

U.S. Advisory Action for co-pending U.S. Appl. No. 13/499,226, dated Sep. 10, 2014.

U.S. Office Action for U.S. Appl. No. 13/499,226, dated Oct. 9, 2014.

U.S. Office Action for co-pending U.S. Appl. No. 13/499,226, dated Jan. 6, 2014.

English translation of an International Preliminary Report on Patentability for International Application No. PCT/JP2010/067254, dated May 18, 2012.

International Search Report for corresponding International Application PCT/JP2010/070501 dated Mar. 29, 2011.

International Search Report for International Application No. PCT/JP2010/067254 dated Nov. 9, 2010.

Masayoshi Takeuchi, "TAGE (toxic AGEs) hypothesis in life style-related disease" Hokuriku University, vol. 28, pp. 33-48, Oct. 2004.

\* cited by examiner

F I G. 1
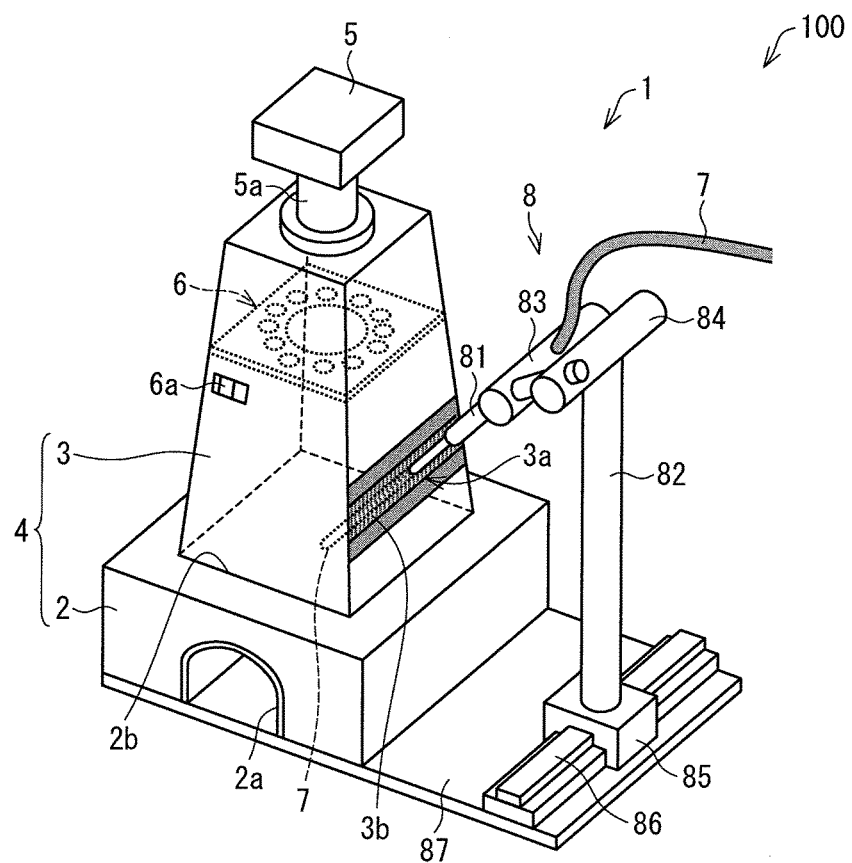

F I G. 1 2
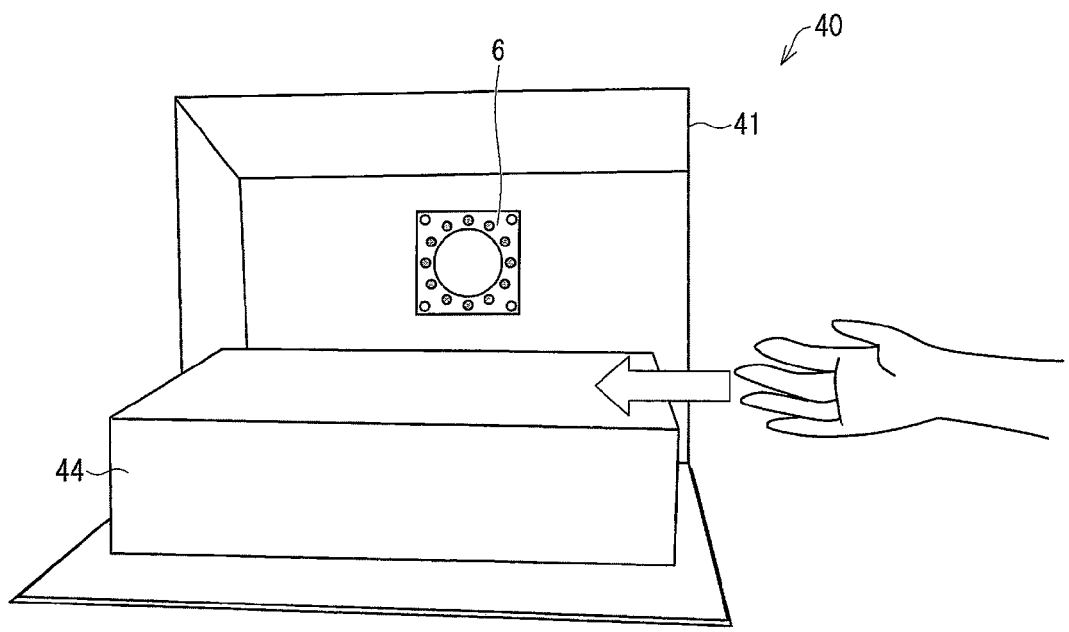

F I G. 1 5
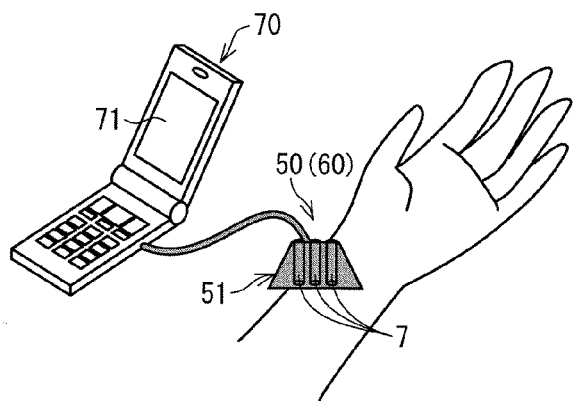
F I G. 1 6
RELATION BETWEEN EXCITATION LIGHT SOURCE AND
FLUORESCENT INTENSITY WITH RESPECT TO AGEs
| | EXCITATION LIGHT (Excitation)(nm) | FLUORESCENCE (Emissin)(nm) |
|---|---|---|
| COLLAGEN-LINKED NORMAL FLUORESCENCE (CLF collagen-linked fluoescence) | 370 | 440 |
| PENTOSIDINE (Pentosidine) | 328 (ACID-HYDROLYZED :335) | 378 (ACID-HYDROLYZED :385) |
| VESPERLYSINES (Vesperlysines) | 370 | 440 |

FIG. 25

| | ACTUAL AGE x | AVERAGE LIFE EXPECTANCY y |
|---|---|---|
| MALE | 1 | 75 |
| MALE | 2 | 74.1 |
| MALE | 3 | 73.2 |
| MALE | ⋮ | ⋮ |
| MALE | 50 | 30.8 |
| MALE | 51 | 29.9 |
| MALE | 52 | 29 |
| MALE | 53 | 28.1 |
| MALE | 54 | 27.2 |
| MALE | 55 | 26.3 |
| MALE | 56 | 25.4 |
| MALE | 57 | 24.5 |
| MALE | ⋮ | ⋮ |
| MALE | 82 | 2 |
| MALE | 83 | 1.1 |
| MALE | 84 | 0.2 |
| MALE | ⋮ | ⋮ |

| | ACTUAL AGE x | AVERAGE LIFE EXPECTANCY y |
|---|---|---|
| FEMALE | 1 | 82.9 |
| FEMALE | 2 | 82 |
| FEMALE | 3 | 81 |
| FEMALE | ⋮ | ⋮ |
| FEMALE | 50 | 36.6 |
| FEMALE | 51 | 35.7 |
| FEMALE | 52 | 34.7 |
| FEMALE | 53 | 33.8 |
| FEMALE | 54 | 32.8 |
| FEMALE | 55 | 31.9 |
| FEMALE | 56 | 30.9 |
| FEMALE | 57 | 30 |
| FEMALE | ⋮ | ⋮ |
| FEMALE | 82 | 6.4 |
| FEMALE | 83 | 5.4 |
| FEMALE | 84 | 4.5 |
| FEMALE | ⋮ | ⋮ |

FIG. 26

MALE : $y = -0.901x + 75.868$

FEMALE : $y = -0.9448x + 83.84$ (※ y = AVERAGE LIFE EXPECTANCY, x = ACTUAL AGE)

MEASUREMENT DEVICE, MEASUREMENT METHOD, MEASUREMENT RESULT PROCESSING DEVICE, MEASUREMENT SYSTEM, MEASUREMENT RESULT PROCESSING METHOD, CONTROL PROGRAM, AND RECORDING MEDIUM

CROSS REFERENCE TO RELATED APPLICATIONS

This application is the National Phase of PCT International Application No. PCT/JP2010/070501, filed on Nov. 17, 2010, which claims priority under 35 U.S.C. 119(a) to Patent Application No. JP-2010-64572, filed in Japan on Mar. 19, 2010 and to Patent Application No. JP-2010-088070, filed in Japan on Apr. 6, 2010, all of which are hereby expressly incorporated by reference into the present application.

TECHNICAL FIELD

The present invention relates to a measurement device, a measurement system, and a measurement method for measuring an intensity of fluorescence generated by irradiating a living body with excitation light. Further, the present invention relates to a method and a system for measuring chemical substances, in which a characteristic of light (fluorescence) radiated by use of excitation light is utilized.

BACKGROUND ART

Recently, with westernization of diets, patients of lifestyle-related disease are increasing, resulting in serious medical and social problems. At present, in Japan, the number of diabetic patients is 8,000,000, and the number of diabetic patients plus pre-diabetic patients is 20,000,000. The three main complications of diabetes are retinopathy, nephropathy, and neuropathy. Diabetes is also a cause for arteriosclerosis. Furthermore, diabetes may cause heart diseases and brain diseases.

A person develops diabetes in such a manner that improper diets and life styles, secretion from fat cells due to fatness, or oxidative stress decrease the function of pancreas, causing shortage of insulin that controls blood glucose level or reducing the effect of insulin. Diabetes has symptoms such as frequent urination and increased amount of urination, and increased thirst. However, such symptoms may not enable patients to realize that they develop diabetes, and most patients know their illness when they are subjected to inspection in hospitals etc. This tells why there are so many "silent" diabetic patients.

However, at the stage where abnormal symptoms resulting from the complications of diabetes are found in hospitals etc., conditions of the disease have advanced too far, making it difficult to completely cure the disease. In particular, many of the complications of diabetes are difficult to cure, and therefore prevention of diabetes is considered as important like many lifestyle-related diseases. For the prevention, early identification and early determination of therapeutic effect are essential, and there are many inspections for diabetes for this purpose.

When blood contains abnormal amounts of carbohydrates and lipids therein, oxidative stress causes (A) a protein and (B) a carbohydrate or a lipid to react with each other, so that a glycated protein is generated. The glycated protein is repeatedly dehydrated and condensed, so that AGEs (advanced glycation end products) are produced. AGEs are end products produced via nonenzymatic glycosylation reaction of protein (Maillard reaction). The glycated protein and a part of AGEs exhibit yellowish brown color, emit fluorescence, and form crosslink by binding to nearby proteins. Further, AGEs have such a biochemical property that AGEs are recognized by an AGEs receptor.

It can be said that AGEs are deposited on and invade a blood vessel wall, so as to affect macrophage partially responsible for an immune system. This causes, for example, an inflammation while releasing cytokine which is a protein, and ultimately causes arteriosclerosis to develop.

In particular, it is found that AGEs derived from aldehydes are particularly accumulated on a lesion area caused by a diabetic complication, so that such AGEs are advocated as an important component of the progress of a complication (see Non-Patent Literature 1). Such AGEs having biological toxicity is, in particular, called "TAGEs (toxic AGEs)".

As such, there is suggested a possibility that a glycated protein, a glycated amino acid, and AGEs etc. are used as an indicator of a health condition. Studies regarding a health condition on the basis of kinds of AGEs, an abundance of AGEs in a human body, etc. have been intensively carried out. In the case of diabetes, as the blood glucose level increases, the amount of AGEs increases. Accordingly, by monitoring AGEs, it is possible to identify diabetes at an early stage or comprehend progress of diabetes. In recent years, there have been developed some methods for monitoring glycated protein, glycated amino acid, AGEs, etc. One example of a method for screening diabetes mellitus by monitoring AGEs is disclosed in Patent Literature 1.

In this method, AGEs are monitored in such a manner that skin of a forearm is irradiated with excitation light and a spectrum of fluorescence from AGEs binding to skin collagen is detected, and the spectrum of the fluorescence thus measured and a predetermined model are compared with each other. This makes it possible to obtain data of AGEs in a non-invasive manner.

Note that Patent Literatures 2 to 4 disclose a living body measurement device which visualizes a blood vessel and includes a plurality of LEDs (light emitting diodes) each having a different wavelength.

CITATION LIST

Patent Literatures

Patent Literature 1
Japanese Translation of PCT International Application Tokuhyo No. 2007-510159 A (Publication date: Apr. 19, 2007)
Patent Literature 2
Japanese Patent Application Publication, Tokukai, No. 2000-189391 A (Publication date: Jul. 11, 2000)
Patent Literature 3
Japanese Patent Application Publication, Tokukai, No. 2001-59814 A (Publication date Mar. 6, 2001)
Patent Literature 4
International Publication WO 1997/24066 (Publication date: Jul. 10, 1997)

Non Patent Literature

Non Patent Literature 1
Takeuchi Masayoshi, "TACE (toxic AGEs) hypothesis in life style-related disease", the Bulletin of Hokuriku University Vol. 28 (October, 2004), pp. 33-48

SUMMARY OF INVENTION

Technical Problem

In a configuration disclosed in Patent Literature 1, a measurement value varies even in a case where the identical test subject measures similar parts repeatedly. This causes a problem that a reliable measurement result cannot be obtained. An inventor of the present invention found that a location irradiated with excitation light varies in each measurement opportunity.

The present invention has been made in view of the problem, and an object of the present invention is to provide a measurement device and a measurement method for reducing variation of measurement values, which variation is caused by a misalignment between locations irradiated with excitation light.

In order to attain the aforementioned object, a measurement device in accordance with the present invention, includes: an excitation light irradiation section for irradiating a specific part or a specific location of a living body with excitation light; and a light receiving section for receiving fluorescence generated by irradiating the specific part or the specific location with the excitation light.

According to the configuration, the excitation light irradiation section irradiates the specific part or the specific location of the living body with excitation light, and the light receiving section receives fluorescence generated by the excitation light. A fluorescent intensity is used as, for example, an indicator indicative of a health condition of a blood vessel.

It is therefore possible to reduce variation of measurement values caused by a misalignment between locations irradiated with excitation light in a case of measuring a measurement target whose fluorescence varies depending on irradiation locations (i.e., a measurement target containing multiple kinds of parts each having different fluorescent intensity).

In order to achieve the object, a measurement method of the present invention includes the steps of: (A) irradiating a specific part or a specific location of a living body with excitation light; and (B) receiving fluorescence generated by irradiating the specific part or the specific location with the excitation light.

According to the configuration, the excitation light irradiation section irradiates the specific part or the specific location of the living body with excitation light, and the light receiving section receives fluorescence generated by the excitation light. It is therefore possible to reduce variation of measurement values caused by a misalignment between locations irradiated with excitation light in a case of measuring a measurement target whose fluorescence varies depending on irradiation locations.

ADVANTAGEOUS EFFECTS OF INVENTION

As described above, a measurement device in accordance with the present invention includes: an excitation light irradiation section for irradiating a specific part or a specific location of a living body with excitation light; and a light receiving section for receiving fluorescence generated by irradiating the specific part or the specific location with the excitation light.

A measurement method in accordance with the present invention includes the steps of: (A) irradiating a specific part or a specific location of a living body with excitation light; and (B) receiving fluorescence generated by irradiating the specific part or the specific location with the excitation light.

Accordingly, in a case of measuring a measurement target whose fluorescence to be generated may vary depending on a location irradiated with excitation light, it is possible to reduce variation of measurement values, which variation is caused by a misalignment between locations irradiated with excitation light.

BRIEF DESCRIPTION OF DRAWINGS

FIG. 1 is a perspective view illustrating an appearance of a measurement device in accordance with one embodiment of the present invention.

FIG. 12 is a perspective view illustrating a state in which an image capturing housing included in the measurement device is tilted.

FIG. 15 is a view illustrating a state in which the portable measurement device is connected to a portable terminal.

FIG. 16 is a table showing a relationship between an excitation light source and a fluorescent intensity in AGEs.

FIG. 25 is a view illustrating a specific example of a correlation information between gender/age and an average life expectancy.

FIG. 26 is a view illustrating another specific example of a correlation information between gender/age and an average life expectancy.

DESCRIPTION OF EMBODIMENTS

[Embodiment 1]

An embodiment of the present invention will be described below with reference to FIG. 1 through FIG. 10. In Embodiment 1, the following description will discuss a measurement system 100 in which a location to be irradiated with excitation light is calculated by analyzing an image in which a part of a body of a test subject to be measured (referred to as "target measurement part") is captured.

(Configuration of Measurement System 100)

Figure 2:
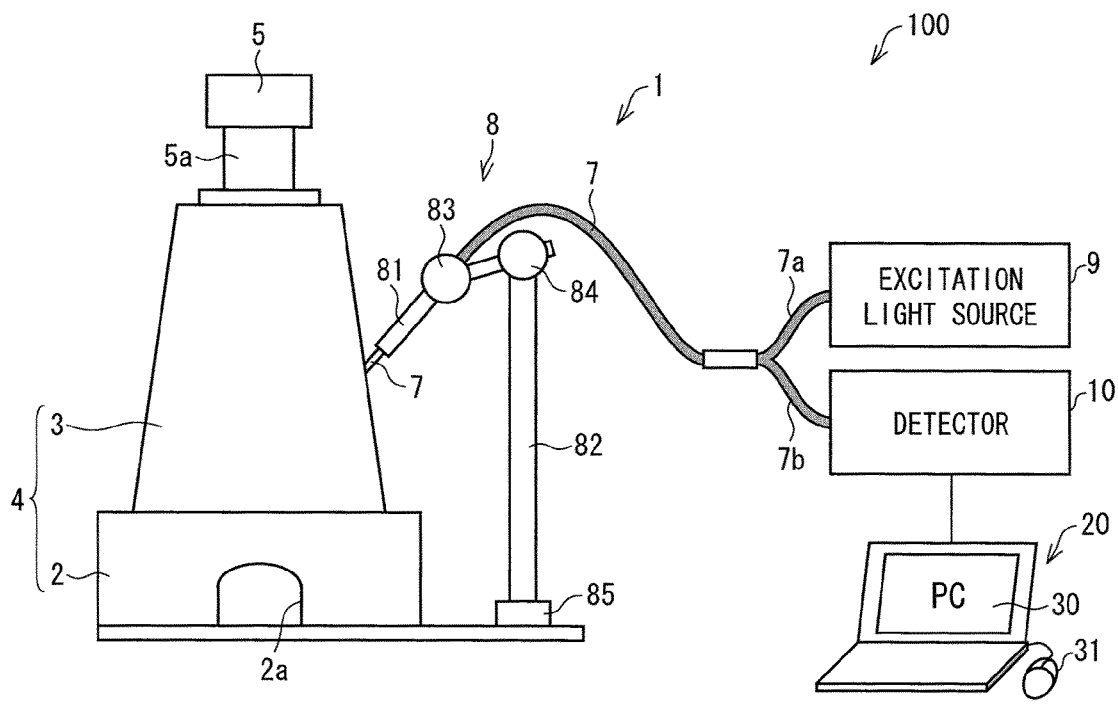
FIG. 2 is a schematic view illustrating a configuration of a measurement system in accordance with one embodiment of the present invention.

FIG. 2 is a schematic view illustrating a configuration of the measurement system 100. As illustrated in FIG. 2, the measurement system 100 includes a measurement device 1 and a control device 20.

The measurement device 1 is provided for measuring an amount of substance accumulated in a living body by (i) causing a specific part or a specific location contained in a target measurement part (such as arms, wrists, fingers, and palms of a test subject) to be irradiated with excitation light, (ii) receiving fluorescence generated by such irradiation; and (iii) measuring an intensity of the fluorescence thus received.

Examples of the specific part encompass arteries, veins, combinations of arteries and veins (i.e., blood vessels), and parts in which no blood vessel exists. Examples of the specific location encompass: a location which is calculated in a certain measurement opportunity; a predetermined location in a living body; and a location which is necessarily specified because of a structure of the measurement device 1. In Embodiment 1, a location to be irradiated with excitation light is calculated on the basis of an image of a target measurement part so that the specific part is irradiated with the excitation light. Such a location serves as a specific location. In the present invention, however, it is possible to determine a specific location without considering a specific part. Alternatively, it is possible to determine in advance a specific location based on a positional correlation between the measurement device 1 and a target measurement part, as described later.

Note that, in a case where a single part is located in the specific location, it can be expressed that the single part is irradiated with excitation light by use of a probe 7 (described later).

The control device 20 controls sections of the measurement device 1, and calculates a location to be irradiated with excitation light and an irradiation angle of excitation light by analyzing an image captured by the measurement device 1. Examples of the control device 20 encompass a general-purpose personal computer and a dedicated terminal device.

(Configuration of Measurement Device 1)

FIG. 1 is a perspective view illustrating an appearance of the measurement device 1. As illustrated in FIG. 1 and FIG. 2, the measurement device 1 includes: an image capturing housing (light-shielding section) 4 in which a cylindrical section 3 is provided on a bottom section 2; a camera (image capturing section) 5; a blood vessel visualizing light source (illuminating section) 6; a probe (excitation light irradiation section, light guiding section) 7; a probe operation section (location adjustment section) 8 for three-dimensionally adjusting a location and an angle of the probe 7; an excitation light source (excitation light irradiation section) 9; and a detector 10.

(Image Capturing Housing 4)

The image capturing housing 4 is provided for efficiently obtaining, by use of the probe 7, fluorescence generated by irradiation of excitation light. The image capturing housing 4 also functions as a light-shielding section for shielding environment light which is directed toward a target measurement part (a specific part or a specific location).

The image capturing housing 4 can be made from any material including (i) plastics such as light-shielding polystyrene and polyethylene, (ii) papers on which aluminum foil is attached so as to face an inner wall of the image capturing housing 4, metals, and woods. Light-shielding plastics are preferable in terms of portability, economical efficiency, and durability.

An insertion port 2a into which a target measurement part is to be inserted is provided in a side surface of the bottom section 2 of the image capturing housing 4. Further, an opening 2b is created in a top surface of the bottom section 2 so that the opening 2b and the cylindrical section 3 are communicated with each other. This causes a space to be secured for capturing a target measurement part.

In a case where the cylindrical section 3 is configured so as to be made up of decomposable several units, the cylindrical section 3 has improved portability because such decomposable several units can be assembled together to obtain the cylindrical section 3 when needed whereas can be disassembled and stored when not used. It is desirable that the cylindrical section 3 has a configuration, such as an inset configuration, which allows the cylindrical section 3 to be easily connected to the bottom section 2.

The measurement device 1 is an installed device, and the cylindrical section 3 has a height of, e.g., 25 cm, and the opening 2b has one side of, e.g., 12 cm. Embodiment is, however, not limited to this.

(Camera 5)

The camera 5 is an image capturing device for capturing a target measurement part, and examples of the camera 5 encompass CCD (charge coupled device) cameras, CMOS (complementary metal-oxide-semiconductor) cameras, and other image capturing devices. The camera 5 is provided on an upper part of the cylindrical section 3, and can capture a target measurement part inserted into the insertion port 2a.

The camera 5 includes a lens 5a, and can enlarge or reduce an image by adjusting the lens 5a. The lens 5a can be directly and manually adjusted by a user or can be adjusted via the control device 20.

An image captured by the camera 5 is supplied to the control device 20, and is displayed on a display section 30.

Note that, in some cases, a commercially available digital camera provides an IR cut filter in front of an image capturing element. The IR cut filter is a filter through which visible light is transmitted and from which infrared rays are reflected. However, the commercially available digital camera can be also arranged so as to remove the IR cut filter and add a band pass filter through which only light in a near-infrared region can be passed. In this case, it is necessary to further provide, in front of the probe 7, a band pass filter through which light having a wavelength of about 450 nm is transmitted. This configuration does not need a housing of the camera. It is therefore possible to downsize a measurement device.

(Blood Vessel Visualizing Light Source 6)

The blood vessel visualizing light source 6 is an illuminating device for irradiating a target measurement part by switching between multiple kinds of illumination light (specifically, red light and infrared light) whose respective wavelengths different from each other. The blood vessel visualizing light source 6 is provided in the cylindrical section and near the camera 5. Examples of the blood vessel visualizing light source 6 encompass Multi-Wavelength LED KED694M31D (manufactured by Kyosemi Corporation). A distance between the blood vessel visualizing light source 6 and the camera 5 is, for example, 4.5 cm.

Figure 3:
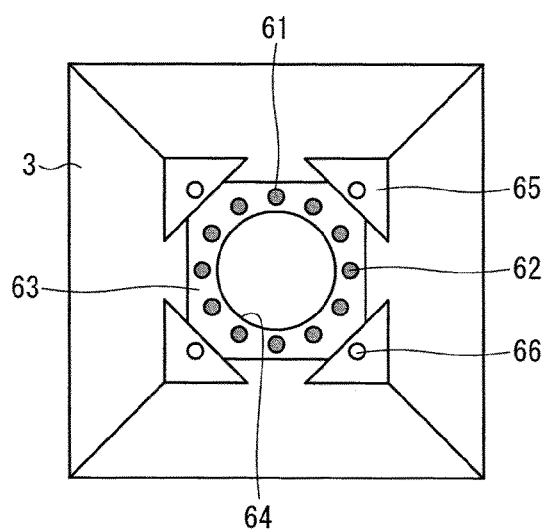
FIG. 3 is a plan view illustrating a configuration of a blood vessel visualizing light source included in the measurement device.

FIG. 3 is a plan view illustrating a configuration of the blood vessel visualizing light source. As illustrated in FIG. 3, a plurality of near-infrared LEDs (infrared color LEDs) 61 and red LEDs 62 serving as a light source in the blood vessel visualizing light source 6 are alternately provided around an opening 64 created in a substrate 63. The substrate 63 is attached to an inner side surface of the cylindrical section 3 by use of fixing washers 65 and screws 66. A center of the opening 64 substantially is coincident with a center of an optical axis of the camera 5. This causes the blood vessel visualizing light source 6 not to hinder the camera 5 from capturing the target measurement part.

The near-infrared LED 61 is a light source which emits light having a wavelength of about 945 nm (890 nm to 1010 nm) in the near-infrared region. By irradiating a skin surface with near-infrared light, it is possible to detect oxygenated hemoglobin. Accordingly, veins can be visualized.

The red LED 62 is a light source which emits light having a wavelength of about 660 nm (620 nm to 700 nm) in a red region. By irradiating a skin surface with red light, it is possible to detect reduced hemoglobin. Accordingly, arteries can be visualized.

Figure 4:
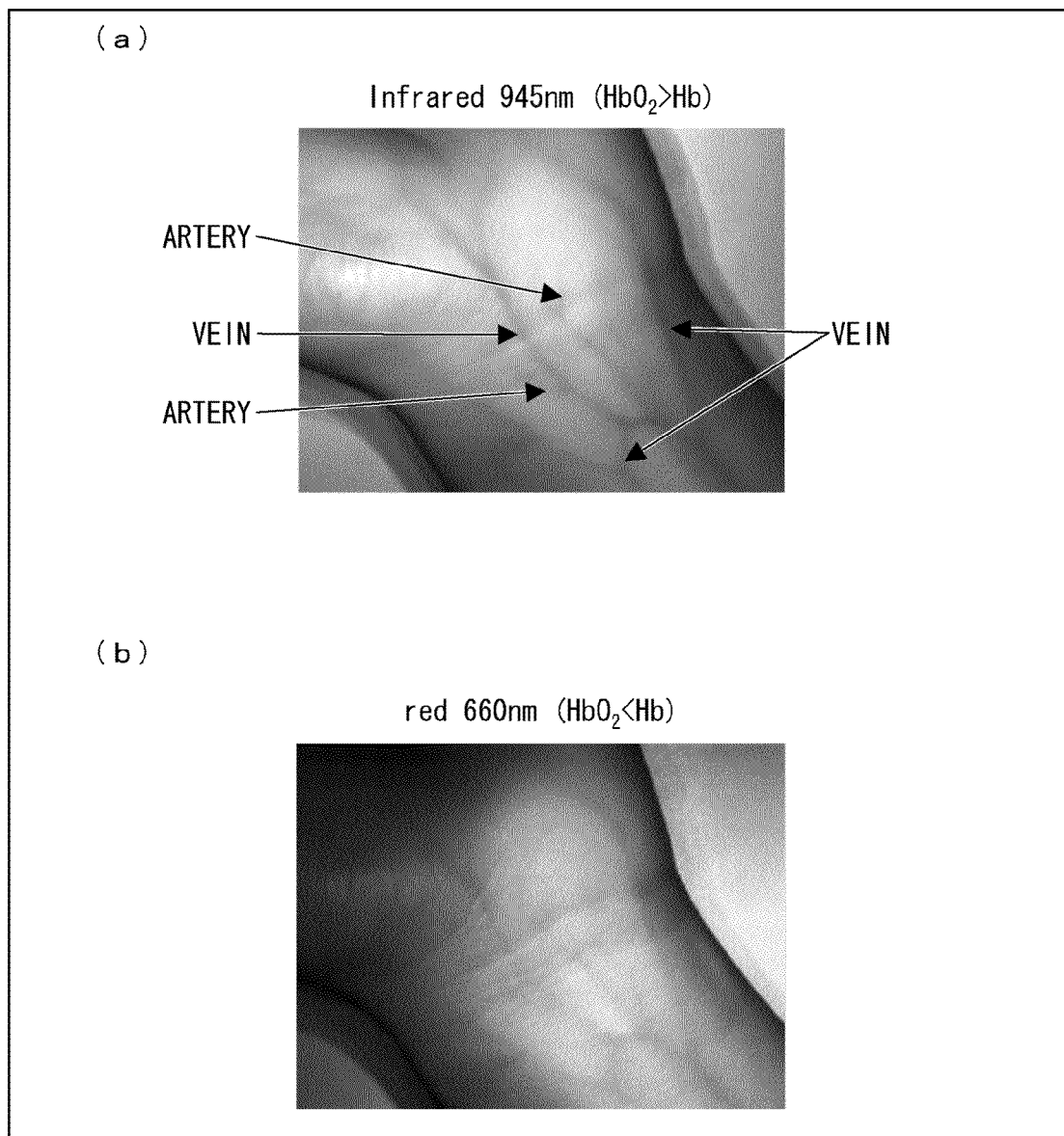
FIG. 4(a) of FIG. 4 is a view illustrating an example of a captured image in a case where a wrist is irradiated with near-infrared light; and (b) of FIG. 4 is a view illustrating an example of a captured image in a case where a wrist is irradiated with red light.

(a) of FIG. 4 is a view illustrating an example of a captured image obtained in a case where a wrist is irradiated with near-infrared light, and (b) of FIG. 4 is a view illustrating an example of a captured image obtained in a case where a wrist is irradiated with red light. In a case where the wrist is irradiated with the near-infrared light as illustrated in (a) of FIG. 4, veins can be visualized more clearly than arteries. On the contrary, in a case where the wrist is irradiated with the red light as illustrated in (b) of FIG. 4, arteries can be visualized more clearly than veins.

Switching between a state in which the near-infrared LEDs 61 are turned on and a state in which the red LEDs 62 are turned on can be carried out by means of a switch 6a provided on an outer side surface of the cylindrical section 3. Note that the switching can be carried out via the control device 20.

As such, by using the blood vessel visualizing light source 6, it is possible to visualize a capillary difficult to view by naked eyes. It is therefore possible to specify a measurement location without considering a size of a blood vessel or a distance of the blood vessel from a skin surface. It is further easy to distinguish between an artery and a vein.

(Probe 7)

The probe 7 (AGEs detection probe) functions as (A) an excitation light irradiation section which irradiates, with excitation light, a specific location (specific part) on a skin surface of the target measurement part in a plurality of measurement opportunities and (B) a light receiving section which receives fluorescence generated by irradiating the specific location (specific part) with excitation light. That is, the probe 7 is a combination of the excitation light irradiation section and the light receiving section.

Figure 5:
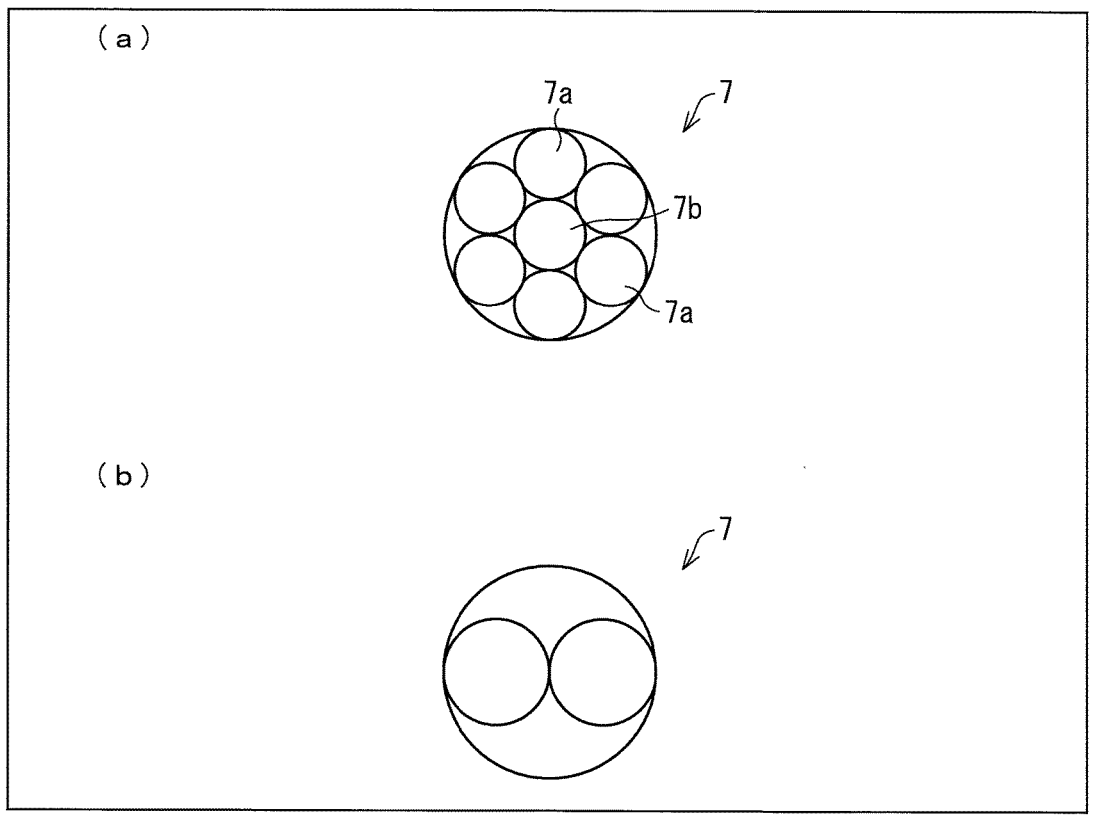
FIG. 5(a) and (b) of FIG. 5 are views each illustrating a cross-sectional view of a probe included in a measurement device (1 or 1001) of the present invention.

(a) and (b) of FIG. 5 are views illustrating cross-sectional shapes of the probe 7. As illustrated in (a) and (b) of FIG. 5, the probe 7 is an optical fiber probe having a coaxial incidence/reflection system. The probe 7 includes: an incident fiber(s) (excitation light irradiation section, light guiding section) 7a for guiding excitation light from the excitation light source 9 toward a specific location; and a reflection fiber(s) (light receiving section, light guiding section) 7b for guiding fluorescence generated in the specific location toward the detector 10. The incident fiber 7a and the excitation light source 9 are combined via an SMA connecter, and the reflection fiber 7b and the detector 10 are combined via an SMA connecter. Since an optical fiber is used as the probe 7, it is possible to guide excitation light toward the specific location as much as possible.

The number of the incident fiber(s) 7a, the number of the reflection fiber(s) 7b, and how to locate the incident fiber(s) 7a and the reflection fiber(s) 7b can be arbitrarily determined. For example, as illustrated in (a) of FIG. 5, a single reflection fiber 7b is provided to be surrounded by six incident fibers 7a.

In this case, diameters of the incident fibers 7a and the reflection fiber 7b are, for example, 600 μm, and cross-sectional areas of the incident fibers 7a and the reflection fiber 7b are 1.7 mm$^2$ and 0.28 mm$^2$, respectively.

Note that a ratio of (A) a fluorescent intensity obtained by a configuration illustrated in (a) of FIG. 5 to (B) a fluorescent intensity obtained by a configuration in which reflection fibers 7b are provided to surround a single incident fiber 7a, i.e., a relative fluorescent intensity is 3:1. Note that the fluorescent intensity does not always increase in accordance with the total cross-sectional area of the reflection fibers 7b.

Alternatively, as illustrated in (b) of FIG. 5, one (1) incident fiber 7a and one (1) reflection fiber 7b can be arranged to be adjacent to each other.

In this case, diameters of the incident fiber 7a and the reflection fiber 7b are, for example, 1800 μm, and a total cross-sectional area of the incident fiber 7a and the reflection fiber 7b is 2.5 mm$^2$.

If the fluorescent intensity obtained from the configuration of (a) of FIG. 5 is assumed to be "3", then the fluorescent intensity obtained from the configuration of (b) of FIG. 4 is "4". Note, however, that the configuration of (b) of FIG. 5 has a problem that the probe 7 is inflexible and the probe 7 is therefore difficult to handle.

The diameter of the reflection fiber 7b is preferably about 300 μm to 2000 μm, in terms of detection efficiency of fluorescence and easiness of handling of optical fibers.

In a case where a measurement is made with respect to a blood vessel, a preferable diameter of the probe 7 also depends on a size of the blood vessel. A diameter of an artery is about 4 mm, and a diameter of an arteriole is about 0.5 mm to 0.03 mm. In a case were an artery is to be measured, the diameter of the probe 7 is preferably about 600 μm.

Note that the incident fiber 7a and the reflection fiber 7b can be separately provided, instead of being coaxially provided. Also note that the excitation light irradiation section and the light receiving section of the present invention can be formed from a material other than optical fibers. For example, a single part to be measured can be irradiated with excitation light of the excitation light source 9 via a converging lens.

(Probe Operation Section 8)

The probe operation section 8 is a manipulator for adjusting (A) an irradiation location and an irradiation angle of excitation light by use of the probe 7 and (B) a distance between an end of the probe 7 and a surface of a target measurement part at the irradiation location (specific location).

Specifically, the probe operation section 8 adjusts a location of the end of the probe 7 so that an irradiation location calculated by a two-dimensional coordinate calculation section 22 of the control device 20 is irradiated with excitation light. The probe operation section 8 also adjusts a distance between the end of the probe 7 and the surface, on the basis of an adjustment value calculated by a distance calculation section 25 of the control device 20. Further, the probe operation section 8 adjusts an irradiation angle of the excitation light with respect to the surface, on the basis of an adjustment value calculated by an angle calculation section 23 of the control device 20.

The probe operation section 8 includes a probe guide 81, a support 82, a distance adjustment section 83, an angle adjustment section 84, a moving section 85, and a rack rail 86.

The probe guide 81 is a tubular member into which the probe 7 is to be inserted. It is difficult to accurately locate a probe 7 having flexibility. It is therefore preferable that, while the probe 7 is being inserted into the probe guide 81, a location and an angle of the probe 7 are adjusted by adjusting a location and an angle of the probe guide 81.

The probe guide 81 is inserted into a probe insertion port (slot section) 3a provided in the cylindrical section 3 or is extended in the proximity of the probe insertion port 3a, while the probe guide 81 is being supported by the support 82. The support 82 is provided on the moving section 85, and the moving section 85 is movable along the rack rail 86. The rack rail 86 is in substantially parallel with a long axis of the probe insertion port 3a. Accordingly, in a case where the moving section 85 moves on the rack rail 86, the probe guide 81 moves along a longitudinal direction of the probe insertion port 3a.

Figure 6:
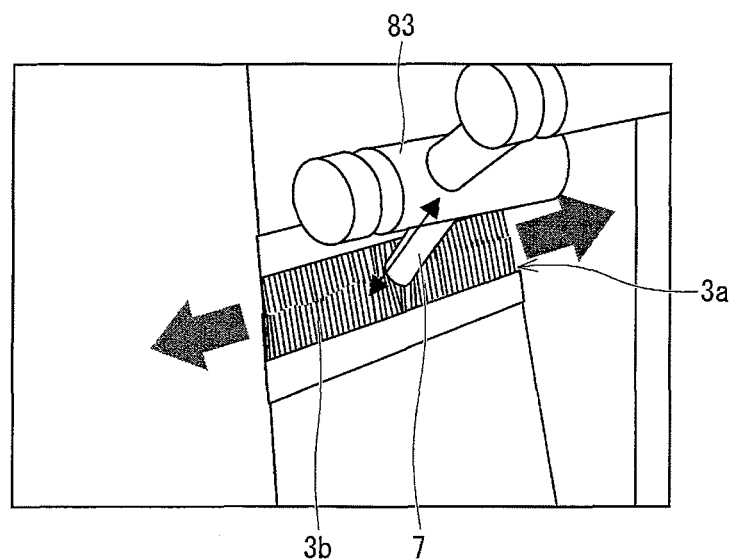
FIG. 6 is a view illustrating a state in which a probe guide is inserted into a probe insertion port provided with respect to the measurement device.

To put it another way, the cylindrical section 3 has the probe insertion port 3a through which the probe 7 can penetrate so as to move along a predetermined direction. FIG. 6 is a view illustrating a state in which the probe guide 81 is inserted into the probe insertion port 3a.

The probe insertion port 3a has a blocking member 3b made from a fibrous material made up of a plurality of fibers having light-shielding property and flexibility. The blocking member 3b is made from, for example, an organic material such as SUS (stainless steel), a metal member (such as aluminum), silicon rubber, or plastic. Note, however, that the blocking member 3b is not limited to those materials.

By providing the blocking member 3b, it is possible to prevent (i) ambient light from entering the cylindrical section 3 through the probe insertion port 3a and (ii) dust and dirt from entering the cylindrical section 3. Since the blocking member 3b is made from the fibrous material made up of the plurality of flexible fibers, the blocking member 3b does not prevent the probe guide 81 (or the probe 7) from moving along the longitudinal direction of the probe insertion port 3a.

The moving section 85 moves on the rack rail 86, and, for example, includes a wheel or a gear driven by an electric motor.

The distance adjustment section 83 adjusts a degree of insertion of the probe guide 81 into the probe insertion port 3a. This causes a distance to be adjusted between the end of the probe 7 and the surface of the target measurement part at the irradiation location. There can be used a well-known mechanism in which the adjustment section 83 adjusts the degree of insertion of the probe guide 81 into the probe insertion port 3a. For example, the degree of insertion of the probe guide 81 can be increased or decreased in conjunction with an extension/contraction motion of a cylinder rod included in an electric cylinder which is provided as a part of the distance adjustment section 83.

The angle adjustment section 84 adjusts an angle of the probe guide 81 with respect to the support 82. This causes a change in irradiation angle of excitation light with respect to the surface. A well-known mechanism for adjusting an angle can be used in the angle adjustment section 84. For example, an angle between the support 82 and the probe guide 81 can be adjusted by rotating a gear in conjunction with an extension/contraction motion of a cylinder rod included in an electric cylinder provided as a part of the angle adjustment section 84.

Further, the angle adjustment section 84 includes a mechanism in which a location of the support 82 of the angle adjustment section 84 (i.e., a height of the angle adjustment section 84 from a stage 87 on which the rack rail 86 is provided) is adjusted. A well-known mechanism for adjusting the height can be used.

The distance adjustment section 83, the angle adjustment section 84, and the moving section 85 are operated under control of the control device 20. A controlling method will be described later.

(Excitation Light Source 9)

The excitation light source 9 is a light source for generating excitation light which projects a target measurement part. The excitation light is light which detects fluorescence derived from AGEs, and has a wavelength range appropriate for measuring AGEs. Examples of the kinds of light sources serving as the excitation light source 9 encompass (a) bulb-type light sources such as a halogen light source and a xenon light source, (b) an LED, and (c) an LD.

There are known about twenty kinds of AGEs whose structures have become clear. Some of them emit fluorescence upon irradiation with excitation light. The table of FIG. 16 shows examples of those AGEs.

In the table of FIG. 16, CLF (collagen-linked fluorescence) is fluorescence caused by AGEs binding to collagen, and is used as a general index for total production of AGEs and accompanying collagen crosslink.

Representative examples of AGEs are pentosidine and vesperlysine. Pentosidine is a fluorescent substance which becomes stable after acid hydrolysis, and has a chemical structure in which lysine and arginine each being equimolar to pentose are cross-linked with each other. It is reported that pentosidine increases in development of diabetes and the end stage of nephropathy. Vesperlysine is acid hydrolyzed and is then isolated as a main fluorescent substances from acid-hydrolyzed AGE-bovine serum albumin (BSA), and has a structure in which two molecules of lysine are cross-linked with each other.

As is clear from the table of FIG. 16, the wavelength of the excitation light source 9 is most preferably 370 nm or proximity thereof. The appropriate wavelength range of the excitation light source set according to the kind of AGEs is 315 to 400 nm (a UVA region) or 315 to 600 nm (a visible light region).

(Detector 10)

The detector 10 receives, via the reflection fiber 7b of the probe 7, fluorescence generated by irradiating a specific location with excitation light, and measures wavelengths of the fluorescence and an intensity in each of the wavelengths. That is, the detector 10 detects wavelengths of fluorescence and respective intensities of fluorescence. Examples of the detector 10 encompass semiconductor detectors such as a CCD array and a CMOS imaging sensor, a photomultiplier tube (PMT), and a channeltron detector. The semiconductor detectors are preferable in terms of portability of the measurement device 1.

Fluorescence has a wavelength longer than that of excitation light. As such, the detector 10 detects light whose wavelength falls within a range from 350 nm to 500 nm. Note, however, that a wavelength of fluorescence to be detected varies depending on kinds of AGEs. As such, it is possible to use a semiconductor detector which can detect a wavelength which falls within a range from 320 nm to 900 nm. Note that a detector 10 including a spectrograph can also be used.

(Configuration Of Control Device 20)

Figure 7:
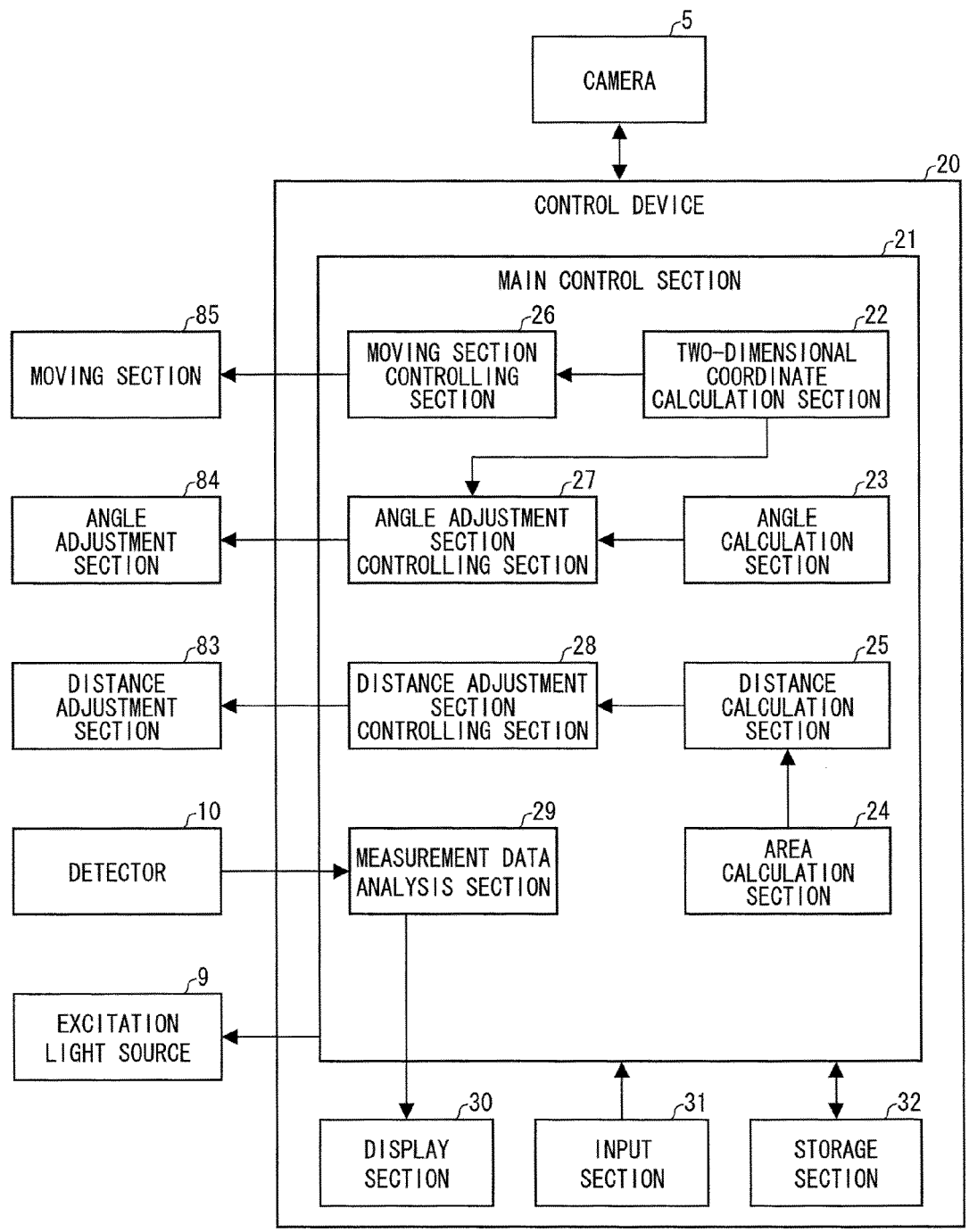
FIG. 7 is a block diagram illustrating a configuration of a control device for controlling the measurement device.

FIG. 7 is a block diagram illustrating a configuration of the control device 20. As illustrated in FIG. 7, the control device 20 includes a main control section 21, the display section 30, an input section 31, and a storage section (first storage section) 32.

The main control section 21 has a function of controlling sections of the measurement device 1, and includes the two-dimensional coordinate calculation section 22, the angle calculation section 23, an area calculation section 24, the distance calculation section 25, a moving section controlling section 26, an angle adjustment section controlling section 27, a distance adjustment section controlling section 28, and a measurement data analysis section 29. Note that the main control section 21 also has a function as an image capturing section controlling section for controlling the camera 5, a function as an excitation light source controlling section for controlling the excitation light source 9, and a function as a display section controlling section for controlling the display section 30.

The display section 30 is provided for displaying a measurement result and an image captured by the camera 5. Examples of the display section 30 encompass a liquid crystal display.

The input section 31 is an input device which accepts an input operation by a user, and examples of the input section 31 encompass keyboards, mice, and input buttons.

The storage section 32 is provided for storing (1) control programs of the sections, (2) an OS program, (3) application programs executed by the main control section 21, and (4) various kinds of data which are read out while the program(s) is/are being executed. In particular, an image captured by the camera 5 is stored by the storage section 32 so as to be correlated with an irradiation location calculated by the two-dimensional coordinate calculation section 22. The storage section 32 is realized by a non-volatile storage device such as a hard disk or a flash memory.

(Details of Sections of Main Control Section 21)

(Two-Dimensional Coordinate Calculation Section 22)

The two-dimensional coordinate calculation section 22 calculates, in the form of a two-dimension coordinate, an irradiation location to be irradiated with excitation light by analyzing an image captured by the camera 5. Note that the two-dimension coordinate in the image and a two-dimension coordinate which is used by the probe operation section 8 in order to locate the probe 7 are identical with each other.

The two-dimensional coordinate calculation section 22 specifically calculates an irradiation location on the basis of a location of a blood vessel of the target measurement part (location of a blood vessel in the image captured by the camera 5). In this case, the two-dimensional coordinate calculation section 22 can calculate (i) an irradiation location so that the blood vessel is irradiated with excitation light or (ii) a location in which no blood vessel exists.

In a case where a blood vessel is irradiated with excitation light, the two-dimensional coordinate calculation section 22 can differentiate an artery from a vein and calculate an irradiation location so that a blood vessel (artery or vein) differentiated by a user is irradiated with excitation light.

In a case where an irradiation location is calculated by the two-dimensional coordinate calculation section 22, an image of a blood vessel (blood vessel pattern) is extracted from an image acquired from the camera 5 (referred to as "captured image"). Such an extraction of the blood vessel pattern can be carried out by a well-known technique. For example, the extraction can be carried out by causing the captured image to be subjected to a differential filter.

The differential filter is a filter for outputting a large value as an output value in a case where a difference is large between a target pixel and respective surrounding pixels. To put it another way, the differential filter is a filter for emphasizing a line or an edge in an image by performing calculation by use of a difference between a pixel value of a target pixel and respective pixel values of surrounding pixels.

After the blood vessel pattern is extracted, the two-dimensional coordinate calculation section 22 calculates, as a location to be irradiated with excitation light, a specific part of the blood vessel pattern or a part which is a predetermined distance away from the specific part. Note that the predetermined distance can be appropriately determined by a person skilled in the art, provided that a measurement value of AGEs in a blood vessel can be clearly distinguished from a measurement value of AGEs measured at a part in which no blood vessel exists.

A method for determining the specific part is not particularly limited. For example, a part of a blood vessel pattern, which part is located at a location closest from a center of a captured image, can be determined as the specific part. Alternatively, a part of the blood vessel pattern, which part has a highest contrast, can be determined as the specific part. The specific part is located at a location to be irradiated with excitation light or in the proximity of the location. This causes the end of the probe 7 to be located at the specific part. It is therefore preferable that the specific part is determined to be located at a part in which the end of the probe 7 is easily located, i.e., a part which is close to an initial location of the end of the probe 7.

Note that the number of calculated location(s) irradiated with the excitation light can be one or more. In a case where a plurality of irradiation locations are calculated, a plurality of times measurements are made. Note, however, that the measurement device 1 includes a plurality of probes 7 so that the plurality of probes 7 measure the respective plurality of irradiation locations. In this case, ends of the plurality of probes 7 can be located at respective irradiation locations (which are calculated by the two-dimensional coordinate calculation section 22).

In a case where (A) switching between a state in which the near-infrared LEDs 61 are turned on and a state in which the red LEDs 62 are turned on is carried out by a user and (B) an irradiation location is calculated on the basis of a blood vessel (artery or vein) intended by a user, the two-dimensional coordinate calculation section 22 does not need to discriminate between (i) a captured image supplied from the camera 5 mainly including an image of an artery and (ii) the captured image mainly including an image of a vein.

On the contrary, in a case where the two-dimensional coordinate calculation section 22 (i) distinguishes, in a captured image, between an artery and a vein and (ii) determines an irradiation location, it is preferable to add, to a captured image supplied from the camera 5, an identifier which is used to discriminates between (a) the captured image being captured while the near-infrared LEDs 61 are being turned on and (b) the captured image being captured while the red LEDs 62 are being turned on.

In a case where the two-dimensional coordinate calculation section 22 calculates a plurality of irradiation locations, it is preferable to (i) add, to a captured image supplied from the camera 5, an identifier which is used to discriminate between (a) each of the plurality of irradiation locations being above an artery, (b) the each of the plurality of irradiation locations being above a vein, and (c) the each of the plurality of irradiation locations being a part in which no blood vessel exists and (ii) add a similar identifier to measurement data thus obtained.

The two-dimensional coordinate calculation section 22 supplies irradiation location information indicative of the irradiation location(s) thus calculated to the moving section controlling section 26 and the distance adjustment section controlling section 28, and controls the storage section 32 to store the irradiation location information so that the irradiation location information is correlated with the captured image thus acquired.

(Angle Calculation Section 23)

The angle calculation section 23 calculates an adjustment value for causing an irradiation angle of excitation light with respect to a surface of the target measurement part at a specific location to fall within a predetermined range of angle (or to be a predetermined angle). The adjustment value is calculated on the basis of a shape of a projection image (spot) of excitation light which is projected toward an irradiation location calculated by the two-dimensional coordinate calculation section 22 by use of an image captured by the camera 5. The captured image, used by the angle calculation section 23, has been captured while (A) the end of the probe 7 is being located at an irradiation location calculated by the two-dimensional coordinate calculation section 22 and (B) excitation light is being projected toward the irradiation location.

The angle calculation section 23 extracts a projection image of excitation light by extracting, from the captured image, a pixel having a predetermined pixel value or more. Then the angle calculation section 23 calculates a ratio of a length of a long axis (major axis) to a length of a short axis (minor axis) of the projection image thus extracted. In a case where the ratio does not fall within a predetermined range, the adjustment value is calculated so that the ratio falls within the predetermined range. This adjustment value is a value indicative of a difference between (A) a current angle of the probe and (B) a preset preferable angle of the probe 7.

A mathematical formula indicative of a relationship between (A) an angle between the probe 7 and the support 82 and (B) a major axis of the projection image projected by the excitation light is stored in the storage section 32 in advance. The angle calculation section 23 can calculate the adjustment value by use of the mathematical formula.

In a case where the excitation light is projected to be perpendicular to the surface of the target measurement part, a projection image of the excitation light becomes a circle. Meanwhile, in a case where an irradiation axis of excitation light is not perpendicular, the projection image becomes an oval. An optimum value of an irradiation angle of excitation light may vary depending on a target measurement part. It is therefore difficult to unconditionally determine a certain optimum value. It is therefore necessary to determine a preferable range of the irradiation angle in advance in accordance with a target measurement part and to adjust an actual irradiation angle so that the actual irradiation angle falls within the preferable range.

The angle calculation section 23 supplies an adjustment value thus calculated to the angle adjustment section controlling section 27.

(Area Calculation Section 24)

The area calculation section 24 calculates an area of a projection image which has been projected by excitation light toward an irradiation location calculated by the two-dimensional coordinate calculation section 22 by use of an image captured by the camera 5. The captured image used by the area calculation section 24 has been captured while (A) the end of the probe 7 has been located at the irradiation location calculated by the two-dimensional coordinate calculation section 22 and (B) the irradiation location has been irradiated with excitation light.

The area calculation section 24 extracts a projection image of excitation light by extracting a pixel having a predetermined pixel value or more from the captured image. This causes the area of the projection image to be calculated.

(Distance Calculation Section 25)

The distance calculation section 25 calculates an adjustment value on the basis of the area calculated by the area calculation section 24. The adjustment value causes a distance between the end of the probe 7 and a surface of a target measurement part at a specific location to be a predetermined distance. Specifically, the distance calculation section 25 calculates a current distance between the end of the probe 7 and the surface on the basis of an area of the projection image calculated by the area calculation section 24, and calculates a difference between the current distance and a predetermined set value. The distance calculation section 25 calculates the distance by use of the mathematical formula, indicative of a relationship between the area of the projection image and the distance, which is stored in the storage section 32 in advance.

Then, the distance calculation section 25 supplies the difference thus calculated, as the adjustment value, to the distance adjustment section controlling section 28.

(Moving Section Controlling Section 26)

The moving section controlling section 26 is provided for transmitting a control signal to the moving section 85, and controls the moving section 85 so that an x-coordinate included in irradiation location information supplied from the two-dimensional coordinate calculation section 22 is identical with an x-coordinate of the end of the probe 7. Note that an x-coordinate axis is parallel with a longitudinal direction of the rack rail 86.

(Angle Adjustment Section Controlling Section 27)

The angle adjustment section controlling section 27 is provided for transmitting a control signal to the angle adjustment section 84, and controls the angle adjustment section 84 so that a y-coordinate included in irradiation location information supplied from the two-dimensional coordinate calculation section 22 is identical with a y-coordinate of the end of the probe 7. Note that a y-coordinate axis is perpendicular to the longitudinal direction of the rack rail 86, and an xy-plan is parallel with the stage 87.

The angle adjustment section controlling section 27 adjusts the height of the angle adjustment section 84 from the stage 87 on the basis of an adjustment value supplied from the angle calculation section 23. During such an adjustment, the angle adjustment section controlling section 27 also adjusts an angle between the probe guide 81 and the support 82 so that the x-coordinate and the y-coordinate of the end of the probe 7 are not misaligned. That is, the angle adjustment section controlling section 27 controls the angle adjustment section 84 so that the irradiation angle of excitation light changes, by an angle indicated by the adjustment value calculated by the angle calculation section 23, while the x-coordinate and the y-coordinate of the end of the probe 7 are being kept.

Note that processes, carried out by the angle calculation section 23 and the angle adjustment section controlling section 27, are not essential for irradiating a target measurement part with excitation light. This is because, in a case where the height of the angle adjustment section 84 from the stage 87 is fixed, then the irradiation angle of the excitation light is automatically determined when the y-coordinate of the end of the probe 7 is determined. However, it is preferable that the main control section 21 includes the angle calculation section 23 in order to irradiate the target measurement part with excitation light at a more preferable irradiation angle.

(Distance Adjustment Section Controlling Section 28)

The distance adjustment section controlling section 28 is provided for transmitting a control signal to the distance adjustment section 83, and controls the distance adjustment section 83 in accordance with an adjustment value calculated by the distance calculation section 25. That is, the distance adjustment section controlling section 28 controls the distance adjustment section 83 so that the distance between the end of the probe 7 and the surface of the target measurement part at the specific location is adjusted to become the predetermined distance.

Note that, as described later, the probe 7 is lowered in a direction perpendicular to the target measurement part, and the target measurement part can be captured in an oblique direction. In this case, the angle between the probe 7 and the surface of the target measurement part is a substantially right angle. As such, there is no need to adjust the angle. Therefore, the probe operation section 8 can easily carry out an operation in which the distance between the end of the probe 7 and the surface of the target measurement part is adjusted to be a certain distance. In this case, there can be provided a guide for keeping a certain distance (for example, about 1 mm) between the end of the probe 7 and the surface of the target measurement part.

(Measurement Data Analysis Section 29)

The measurement data analysis section 29 synthesizes a screen for displaying a measurement result by use of measurement data supplied from the detector 10, and displays a synthesized screen on the display section 30. The measurement result can be displayed as a fluorescence spectrum or can be displayed as a numerical value indicative of a fluorescent intensity in a predetermined wavelength. Further, the measurement data analysis section 29 has a function of carrying out various kinds of calculation with respect to measurement data.

(Meaning of Irradiating Identical Irradiation Locations)

The following description will discuss the meaning of irradiating the identical locations (i.e., measurement locations) with excitation light in a plurality of measurement opportunities.

Figure 8:
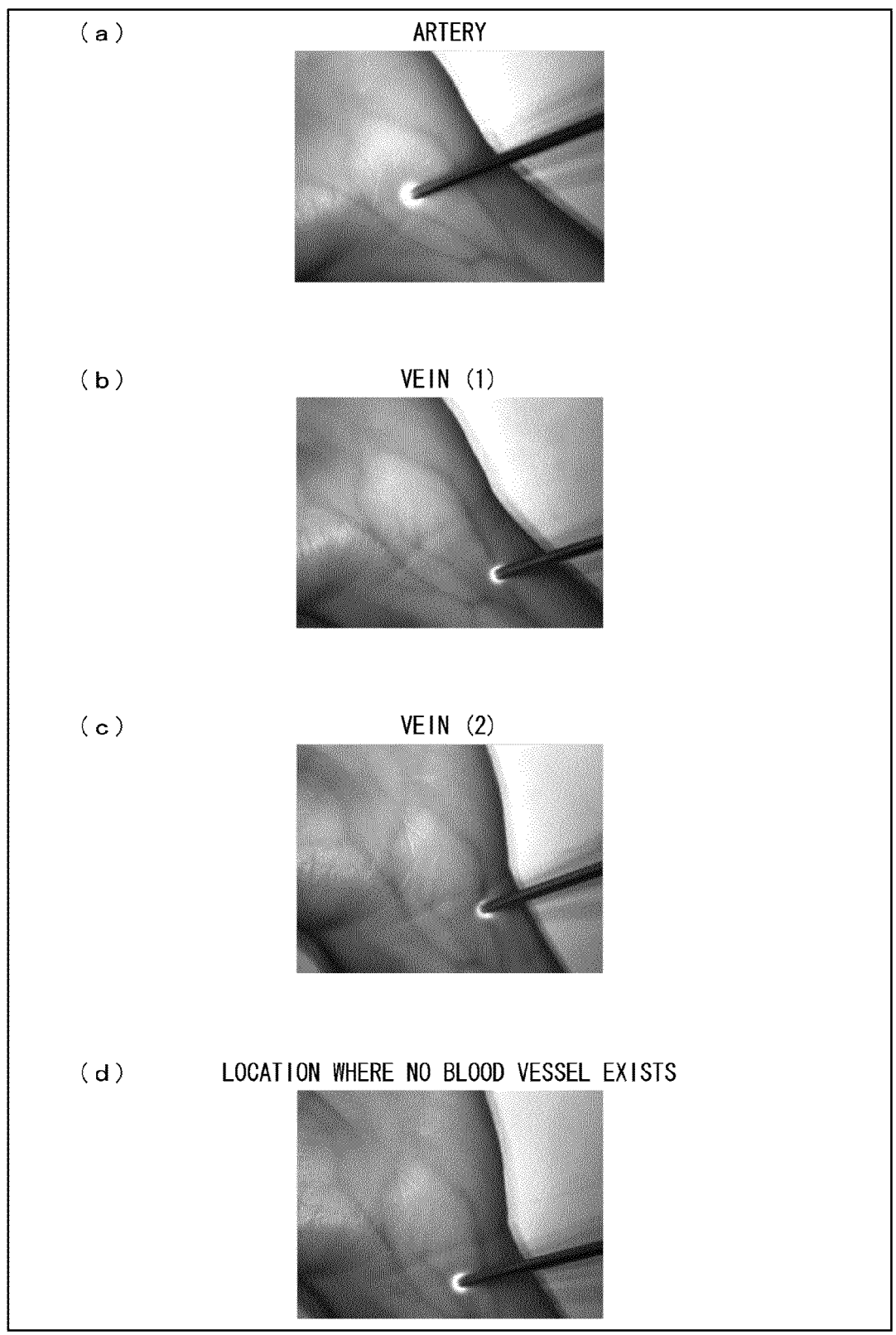
FIG. 8(a) of FIG. 8 is a view illustrating a state in which an end of a probe is located at an artery; (b) of FIG. 8 is a view illustrating a state in which an end of a probe is located at a vein; (c) of FIG. 8 is a view illustrating a state in which an end of a probe is located at a location of a vein, which location is different from that of (b) of FIG. 8; and (d) of FIG. 8 is a view illustrating a state in which an end of a probe is located at a part in which no blood vessel exists.
Figure 9:
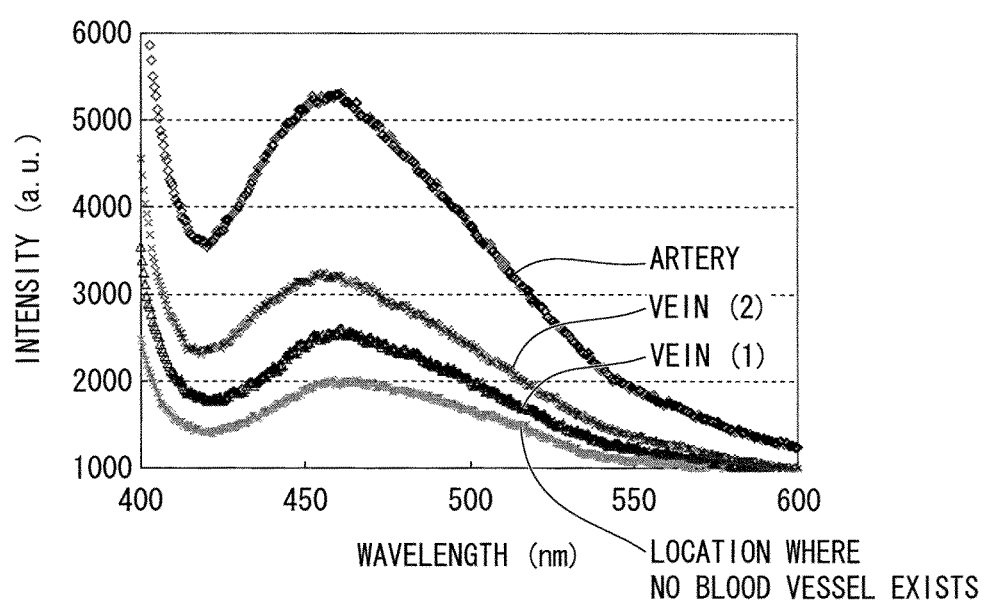
FIG. 9 is a graph showing results measured at locations indicated in (a) to (d) of FIG. 8.

(a) through (d) of FIG. 8 are views illustrating states in which the end of the probe 7 is located at respective different locations of a wrist. Specifically, (a) of FIG. 8 is a view illustrating a state in which the end of the probe 7 is located at an artery, (b) of FIG. 8 is a view illustrating a state in which the end of the probe 7 is located at a vein, (c) of FIG. 8 is a view illustrating a state in which the end of the probe 7 is located at another vein different from that of (b) of FIG. 8, and (d) of FIG. 8 is a view illustrating a state in which the end of the probe 7 is located at a part in which no blood vessel exists. FIG. 9 is a graph illustrating results measured at the locations indicated in respective (a) through (d) of FIG. 8.

As illustrated in FIG. 9, a generated fluorescent intensity varies depending on a location of the wrist which location is irradiated with excitation light. In particular, a stronger fluorescent intensity is detected when a blood vessel is irradiated with excitation light than when a part in which no blood vessel exists is irradiated with excitation light, and a stronger fluorescent intensity is generated when an artery is irradiated with excitation light than when a vein is irradiated with excitation light.

Such facts were found by the inventor of the present invention, and have not been known before. Therefore, according to conventional AGEs measurement devices, no particular attention has been paid to a location to be irradiated with excitation light. This has caused a problem that, in the conventional AGEs measurement devices, measurement values are changed every time AGEs are measured even in a case where the measurements are made with respect to an identical test subject.

In the present invention, locations to be irradiated with excitation light in a plurality of measurement opportunities are adjusted to be identical locations. This allows an improvement in reproducibility of measurement result. This ultimately makes it possible to improve reliability of the measurement result.

No conclusion has been arrived yet as to whether a measurement is preferably made with respect to an artery or a vein when AGEs are measured. However, it is sure that a stronger fluorescent intensity is generated when a measurement is made with respect to an artery than when a measurement is made with respect to a vein. It is therefore preferable that, in a case where a measurement is made with respect to a test subject whose amount of AGEs accumulated in a body is low, it is preferable for AGEs to be measured at an artery. This is because, if the fluorescent intensity is too low, then a measurement value is liable to be affected by a background.

Note that the reason why the fluorescent intensity generated when AGEs are measured at an artery is stronger than that generated when AGEs are measured at a vein has not yet been solved at present. However, it is highly possible that a blood vessel wall is damaged in an artery, and therefore cholesterol is attached to the artery in order to repair such damage, which results in arteriosclerosis. This possibility seems to relate to the reason.

(Flow of Processing in Measurement System 100)

Figure 10:
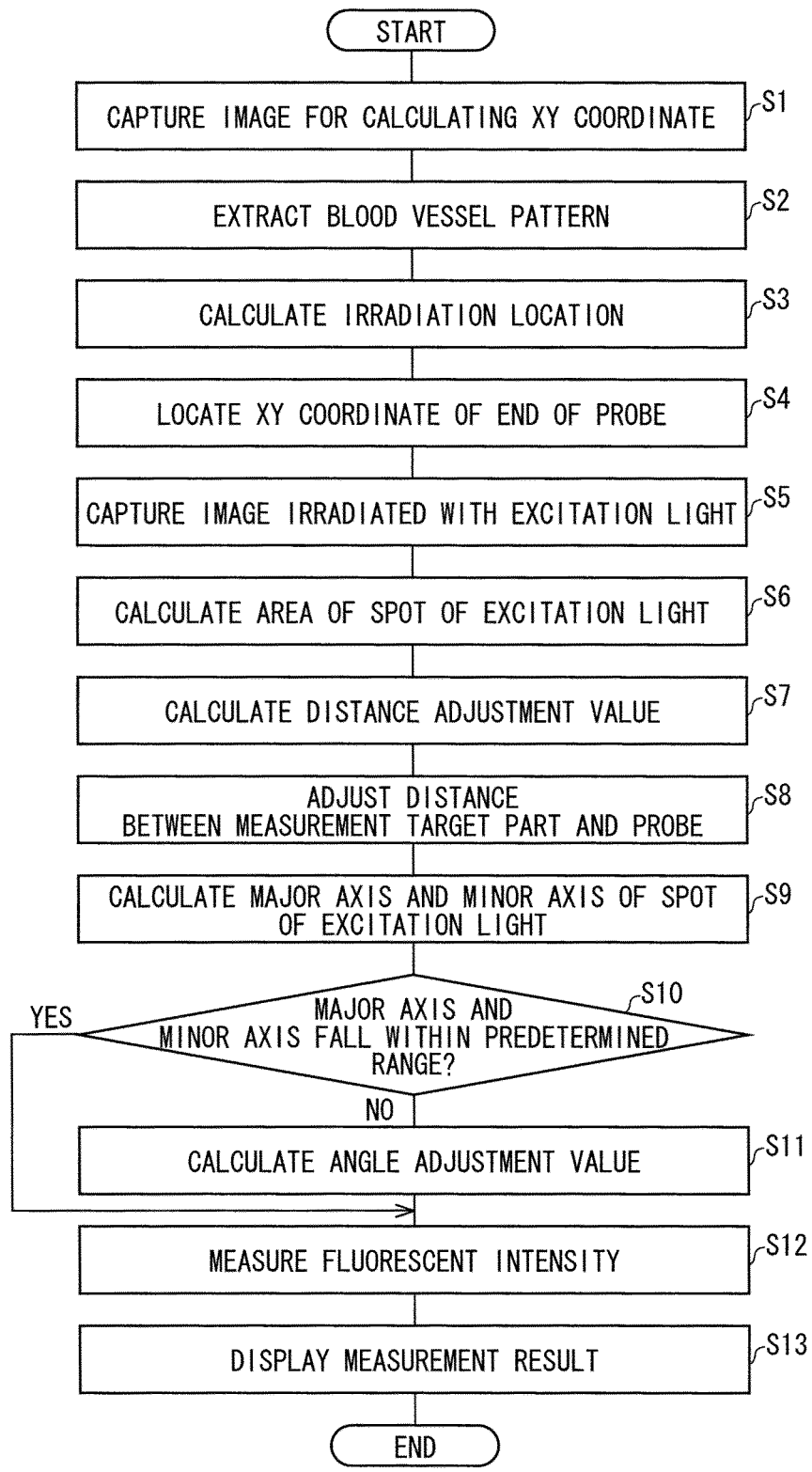
FIG. 10 is a flowchart showing an example flow of processing in the measurement system.

An example flow of processing in the measurement system 100 will be described below. FIG. 10 is a flowchart showing an example flow of processing in the measurement system 100. The following description will discuss a case where AGEs are measured at an artery.

First, a test subject inserts a target measurement part into the insertion port 2a, and then the near-infrared LEDs 61 or the red LEDs 62 is turned on so that an artery is visualized. After that, the test subject enters an instruction for starting a measurement via the input section 31.

Upon receipt of the instruction, the main control section 21 controls the camera 5 to capture a target measurement part (S1). A captured image is used to calculate an irradiation location (x-coordinate and y-coordinate), and is supplied to the two-dimensional coordinate calculation section 22.

Upon receipt of the captured image, the two-dimensional coordinate calculation section 22 extracts an artery pattern from the captured image (S2). Then, the two-dimensional coordinate calculation section 22 calculates a part of an artery pattern which is the closest to a center of the captured image, and determines the part of the artery pattern as a location to be irradiated with excitation light (i.e., measurement location) (S3). The two-dimensional coordinate calculation section 22 supplies, to the moving section controlling section 26 and the angle adjustment section controlling section 27, irradiation location information indicative of a coordinate of the irradiation location thus calculated.

Upon receipt of the irradiation location information, the moving section controlling section 26 controls the moving section 85 so that an x-coordinate included in the irradiation location information supplied from the two-dimensional coordinate calculation section 22 is identical with an x-coordinate of the end of the probe 7. Further, the angle adjustment section controlling section 27 controls the angle adjustment section 84 so that a y-coordinate included in the irradiation location information supplied from the two-dimensional coordinate calculation section 22 is identical with a y-coordinate of the end of the probe 7. By controlling the moving section 85 and the angle adjustment section 84, the end of the probe 7 is located at coordinates (x, y) calculated by the two-dimensional coordinate calculation section 22 (S4).

Thereafter, the main control section 21 controls the excitation light source 9 to emit excitation light. This causes a specific location of the target measurement part to be irradiated with the excitation light emitted from the end of the probe 7. In this state, the main control section 21 controls the camera 5 to capture again an image of the target measurement part, and the image thus captured (referred to as "excitation light irradiation image") is supplied to the area calculation section 24 and the angle calculation section 23 (S5).

Upon receipt of the excitation light irradiation image, the area calculation section 24 calculates an area of a projection image of excitation light, which projection image is included in the excitation light irradiation image, and then supplies the area thus calculated to the distance calculation section 25 (S6).

A current distance between the end of the probe 7 and a surface of the target measurement part at the specific location is calculated by the distance calculation section 25 on the basis of the area of the projection image calculated by the area calculation section 24. The distance calculation section 25 calculates a difference between the distance and a predetermined set value (S7). Then, the distance calculation section 25 supplies the adjustment value indicative of the difference thus calculated to the distance adjustment section controlling section 28.

Upon receipt of the adjustment value, the distance adjustment section controlling section 28 controls the distance adjustment section 83 so that the distance between the end of the probe 7 and the surface changes by a distance indicated by the adjustment value (S8).

Then, the angle calculation section 23 extracts the projection image of the excitation light from the excitation light irradiation image, and then calculates a ratio of a length of a long axis (major axis) to a length of a short axis (minor axis) of the projection image thus extracted (S9). The angle calculation section 23 determines whether or not the ratio falls within a predetermined range. In a case where the ratio does not fall within the predetermined range (NO in S10), the angle calculation section 23 calculates an adjustment value (angle adjustment value) which causes the ratio to fall within the predetermined range (S11).

Meanwhile, in a case where the ratio falls within the predetermined range (YES in S10), the angle calculation section 23 terminates processing (and the processing proceeds to S12).

Note that (i) the processing in the area calculation section 24 and the distance calculation section 25 and (ii) the processing in the angle calculation section 23 can be executed in the inverse order.

After that, the main control section 21 controls the excitation light source 9 to emit excitation light with which the specific location of the target measurement part is again irradiated (excitation light emitting step). Fluorescence generated by the excitation light is received by the reflection fiber 7b (light receiving step). Then the fluorescence is guided toward the detector 10 via the reflection fiber 7b. Upon receipt of the fluorescence, the detector 10 measures wavelengths of the fluorescence and intensities for respective wavelengths, then supplies such measurement data to the measurement data analysis section 29 (S12). Note that the image, in which the specific location is irradiated with excitation light is captured, can be (i) displayed on the display section 30 and (ii) stored in the storage section 32.

Upon receipt of the measurement data, the measurement data analysis section 29 prepares a graph etc. for display by use of the measurement data, and the graph etc. is displayed on the display section 30 (S13).

Note that, in order to measure a fluorescence intensity more accurately, it is preferable to (i) project excitation light toward a specific reference substance so as to generate fluorescence and (ii) correct, by use of the fluorescence as a reference, an intensity of fluorescence received by the detector 10.

That is, a measurement method of the present invention can include the steps of: a standard fluorescence receiving step in which fluorescence to be a standard of measurement of a fluorescent intensity is received; and a correcting step in which the intensity of the fluorescence received in the light-receiving step is corrected by use of the intensity of the fluorescence received in the standard fluorescence receiving step. It is preferable that the standard fluorescence receiving step and the correcting step are carried out during a short time period before or after the detector 10 receives fluorescence from the specific location. Such correction of the intensity of the fluorescence allows an improvement in reliability of measurement values.

Examples of calculation carried out when the intensity is corrected by use of the reference encompass calculating a ratio of a measurement value to the reference.

It is preferable to select, as such a reference substance, a substance whose fluorescent intensity is less liable to decrease even in a case where the substance is irradiated with excitation light for a long time. It is preferable to use, as the reference substance, a nano particle fluorescent material in which a nanometer-size particle is included. A fluorescent intensity of the nano particle fluorescent material is less liable to decrease even in a case where the nano particle fluorescent material is continuously irradiated with excitation light. In a case where (i) fluorescent beads are used as the reference substance and (ii) excitation light is continuously projected, a problem occurs that the fluorescent intensity is gradually decreased. Note that a fluorescence wavelength of the nano particle fluorescent material can be adjusted by adjusting a size of the nano particle.

In a case where the fluorescent intensity obtained in Step S12 does not reach a predetermined fluorescent intensity, the two-dimensional coordinate calculation section 22 can correct a location irradiated with excitation light. In this case, for example, the two-dimensional coordinate calculation section 22 can increase or decrease an x-coordinate and/or a y-coordinate of the location irradiated with excitation light by a predetermined value. The predetermined value can be appropriately set in advance by a person skilled in the art. The measurement device 1 irradiates the location thus corrected with excitation light, and again measures the fluorescent intensity.

In this configuration, in a case where a blood vessel is not irradiated with excitation light for some reason, a location to be irradiated is slightly moved and is irradiated again. This makes it possible to raise a possibility to detect fluorescence having a predetermined intensity or more.

(Effect of Measurement System 100)

As is clear from the description, the measurement system 100 analyzes an image in which a target measurement part is captured, and calculates a location irradiated with excitation light on the basis of a location of a blood vessel. Since the location of the blood vessel scarcely changes in a short time period, this irradiation location is calculated on the basis of the location of the blood vessel. This makes it possible to irradiate the identical locations of the identical test subject's body with excitation light in different measurement opportunities.

Even in a case where the measurement system 100 makes a measurement in which values may change due to the fact that locations irradiated with excitation light are different, the measurement system 100 can provides measurement results whose measurement values are less liable to vary and which have high reproducibility.

The description has discussed an example where the measurement is made with respect to AGEs, however, the present invention is not limited to the measurement of AGEs. The present invention can be applied to a measurement device in which measurement values may change due to the fact that locations irradiated with excitation light are different. To put it another way, a wavelength of the excitation light emitted from the excitation light source is not limited to a wavelength suitable for measuring advanced glycation end products.

(Modification)

In the measurement system 100, it is not always necessary to calculate an irradiation location for each measurement opportunity. A coordinate calculated by the two-dimensional coordinate calculation section 22 in a first measurement opportunity, an adjustment value calculated by the angle calculation section 23, and an adjustment value calculated by the distance calculation section 25 are stored in the storage section 32 in advance. Then, the irradiation location can be irradiated with the excitation light from a second measurement opportunity by use of location coordinates (x, y) indicated by the information stored in the storage section 32, an irradiation angle of the excitation light, and a degree of insertion of the probe guide 81 to the probe insertion port 3a.

That is, the control device 20 includes the storage section 32 for storing irradiation location information indicative of a location to be irradiated with excitation light. The measurement device 1 can further include a probe operation section 8 for adjusting a location of the probe 7 so that a location indicated by the irradiation location information stored in the storage section 32 is irradiated with excitation light.

With the configuration, it is unnecessary to calculate an irradiation location for each measurement opportunity. This makes it possible to reduce a throughput of the control device 20.

Note that, according to the configuration, it is preferable to separately provide a configuration which causes locations of the target measurement part with respect to the probe operation section 8 to be identical with each other in a plurality of measurement opportunities. For example, a protruding part for defining a location of an end of a fist can be provided in the bottom section 2 while a wrist is being inserted into the insertion port 2a and the fist is being clenched.

Alternatively, the control device 20 acquires, from a user via the input section 31, the irradiation location information indicative of the location to be irradiated with the excitation light, and controls the storage section 32 to store the irradiation location information. In the next measurement opportunity, the control device 20 can control the probe operation section 8 so that the end of the probe 7 is located at the irradiation location indicated by the irradiation location information stored in the storage section 32.

With the configuration, a user personally determines a location to be irradiated with excitation light and enters the location to the control device 20. Once information on the location is entered by the user, the location is irradiated with excitation light from the next measurement opportunity. This makes it possible for identical locations to be irradiated with excitation light in a plurality of measurement opportunities.

Instead of a step in which a location of the end of the probe 7 is located at an irradiation location calculated by the two-dimensional coordinate calculation section 22, the user can manually and directly operate the probe operation section 8 so that the location of the end of the probe 7 is located at the irradiation location. In this case, the control device 20 does not need to have a function of controlling the probe operation section 8. Instead, the control device 20 controls the irradiation location calculated by the two-dimensional coordinate calculation section 22 to be displayed, in real time, in an image captured by the camera 5. A user can operate the probe operation section 8 while watching the real-time image displayed on the display section 30, so that the end of the probe 7 is located at the displayed irradiation location.

The image, in which the target measurement part (measured part) irradiated with excitation light is captured, is stored in the storage section (second storage section) 32 in the first measurement opportunity. And, the display section 30 can display not only the image captured by camera 5 in real time, but also the image stored in the storage section 32, from the second measurement opportunity.

With the configuration, by watching a first captured image displayed on the display section 30, a user can know where to locate the end of the probe 7. By comparing the real-time captured image with the first captured image, it is possible to easily locate the end of the probe 7 at an irradiation location of the first measurement opportunity. This makes it easier to irradiate identical locations with excitation light in a plurality of measurement opportunities. In this configuration, the probe operation section 8 can be manually operated by a user, or alternatively, can be operated by a user via the control device 20.

According to the configuration in which the probe operation section 8 is operated by a user, a case is assumed in which it is difficult to accurately project excitation light toward the irradiation location calculated by the two-dimensional coordinate calculation section 22. It is therefore preferable to provide an informing section for informing a user of whether or not the irradiation location calculated by the two-dimensional coordinate calculation section 22 is being irradiated with excitation light. Such informing can be carried out by use of sound (beep), an image, light, and/or the like. That is, the informing section is, for example, a speaker, a display section, a light emitting device alone or in combination. The display section 30 included in the control device 20 can be used as the display section. The speaker included in the control device 20 can be used as a speaker.

The light emitting device is, for example, an LED provided in the measurement device 1. In a case where an LED is used as the informing section, a user can be informed of whether or not the irradiation location calculated by the two-dimensional coordinate calculation section 22 (referred to as "target irradiation location") is irradiated with excitation light by switching between lighting patterns on the basis of a distance between the target irradiation location and an actual irradiation location (hereinafter, referred to as "actual-measured irradiation location") of excitation light.

For example, four lighting patterns (including OFF-pattern) are prepared in advance, and can be selected as follows: the LED is turned off in a case where an actual-measured irradiation location is a first distance (e.g., 3 mm) or more away from the target irradiation location; the LED is blinking (at a low speed) at predetermined lighting time intervals in a case where an actual-measured irradiation location is located between the first distance and a second distance (e.g., 0.5 mm); the LED is blinking (at a high speed) at time intervals shorter than the predetermined lighting time intervals in a case where the actual-measured irradiation location is located between the second distance and a third distance (e.g., 0.1 mm); and the LED can be turned on in a case where the actual-measured irradiation location is located between the location to be irradiated and the third distance (e.g., an error is less than 0.1 mm).

Two lighting patterns or three lighting patterns can be employed instead of the four lighting patterns. In a case where the two lighting patterns are used, for example, the LED can be turned on when an actual-measured irradiation location is substantially identical with a target irradiation location (when the actual-measured irradiation location falls within a predetermined tolerance range), and otherwise, the LED can be turned off. In a case where the three lighting patterns are used, for example, three lighting patterns can be made up of OFF-pattern, blinking-pattern, and lighting-pattern.

In order to realize such configuration, the main control section 21 includes a determination section for determining whether or not an irradiation location calculated by the two-dimensional coordinate calculation section 22 is identical with a location actually irradiated with excitation light (irradiation location adjusted by the probe operation section 8).

The location actually irradiated with excitation light can be calculated on the basis of an image (second captured image) of the camera 5 in which a part irradiated with excitation light is captured. In this case, the main control section 21 can include an irradiation location calculation section for calculating an irradiation location of excitation light on the basis of the second captured image.

In a case where the probe operation section 8 is operated by a user via the control device 20, a location of the end of the probe 7 can be regarded as a location which is actually irradiated with excitation light. The location of the end is calculated on the basis of operation history of the probe operation section 8. The location thus calculated can be used as a current location irradiated with excitation light. This processing can be carried out by the determination section.

The measurement device 1 can have a configuration in which a plurality of probes 1each having a different diameter are provided so as to be switched from one to another. That is, according to the configuration, the probe 7 is made up of a plurality of probes each having a different diameter, and a switching section for selecting one of the plurality of probes which should receive fluorescence (or emit excitation light) can be provided in the measurement device 1.

As early described, a suitable diameter of the probes 7 varies depending on a size of a blood vessel. Accordingly, by selecting one of the plurality of probes 7 each having a different size, it is possible to suitably make a measurement with respect to multiple blood vessels each having a different size.

Examples of the mechanism for switching between the plurality of probes (switching section) 7 encompass a configuration in which the plurality of probes 7 are all connected to the excitation light source 9 and the detector 10 in advance, and one of the plurality of probes 7 which should emit excitation light. Alternatively, according to another mechanism, one of the plurality of probes 7 which should be connected to the excitation light source 9 and the detector 10 is selected.

The measurement device 1 can include a plurality of probes 7 and measure at least three parts including, as specific parts, an artery, a vein, and a part in which no blood vessel exists. In this case, the two-dimensional coordinate calculation section 22 calculates the at least three irradiation parts including parts above the artery, the vein, and the part in which no blood vessel exists, and the probe operation section 8 locates at least three ends of the plurality of probes 7 at respective irradiation locations.

With the configuration, measurements are simultaneously made with respect to a plurality of parts. It is highly possible that measurement values of the artery, the vein, and the part in which no blood vessel exists differ from each other. This can broaden options to analyze measurement values. For example, the most reliable one of the three measurement values can be selected.

It is possible to simultaneously make measurements with respect to a plurality of parts of an artery and/or a vein. Note that the plurality of parts serve as specific parts each having a different size. In this case, the two-dimensional coordinate calculation section 22 can calculate, as the irradiation locations of excitation light, the plurality of parts of blood vessels each having a different size by analyzing the image of the camera 5.

Also in this configuration, it is possible to broaden options to analyze measurement values. For example, the most reliable one of the plurality of measurement values thus obtained can be selected.

[Embodiment 2]

Embodiment 2 of the present invention will be described below with reference to FIG. 11 through FIG. 13. Note that sections having the like functions as the sections described in Embodiment 1 are denoted by the like reference signs and the detailed description thereof is omitted. In Embodiment 2, the following description will discuss a measurement device 40 which repeatedly locates an end of a probe at identical locations of an arm (target measurement part) by placing the arm on an arm pillow 44.

Figure 11:
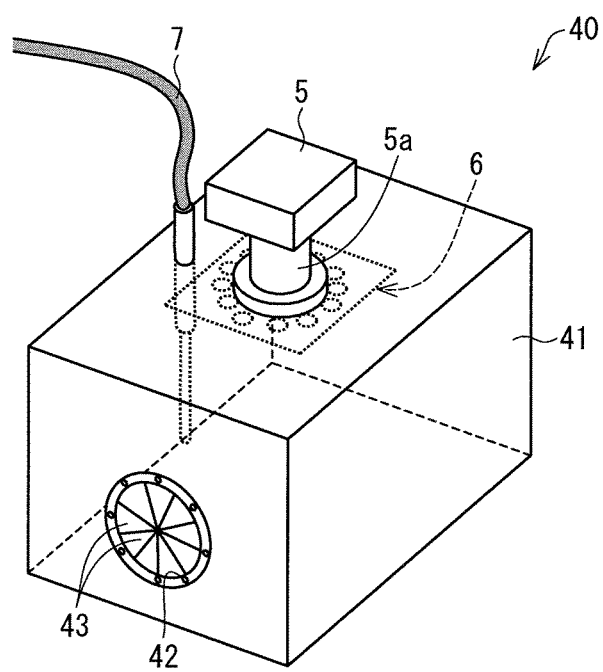
FIG. 11 is a perspective view illustrating an appearance of a measurement device in accordance with another embodiment of the present invention.

FIG. 11 is a perspective view illustrating an appearance of the measurement device 40. FIG. 12 is a perspective view illustrating a state in which an image capturing housing 41 included in the measurement device 40 is tilted.

As illustrated in FIG. 11 and FIG. 12, the measurement device 40 includes the image capturing housing (light-shielding section) 41, a camera 5, a blood vessel visualizing light source 6, a probe 7, and the arm pillow (fixing section) 44. Note that (i) the arm pillow 44 is not illustrated in FIG. 11 and (ii) the probe 7 is not captured in FIG. 12.

The image capturing housing 41 is made from a material having a light-shielding property, which is similar to the image capturing housing 4, and secures an image capturing space in which a target measurement part is captured. The camera 5 and the blood vessel visualizing light source 6 are provided on a top surface of the image capturing housing 41. The image capturing housing 41, like the measurement device 1, is configured so that an image can be captured in a state in which a blood vessel is visualized.

Figure 13:
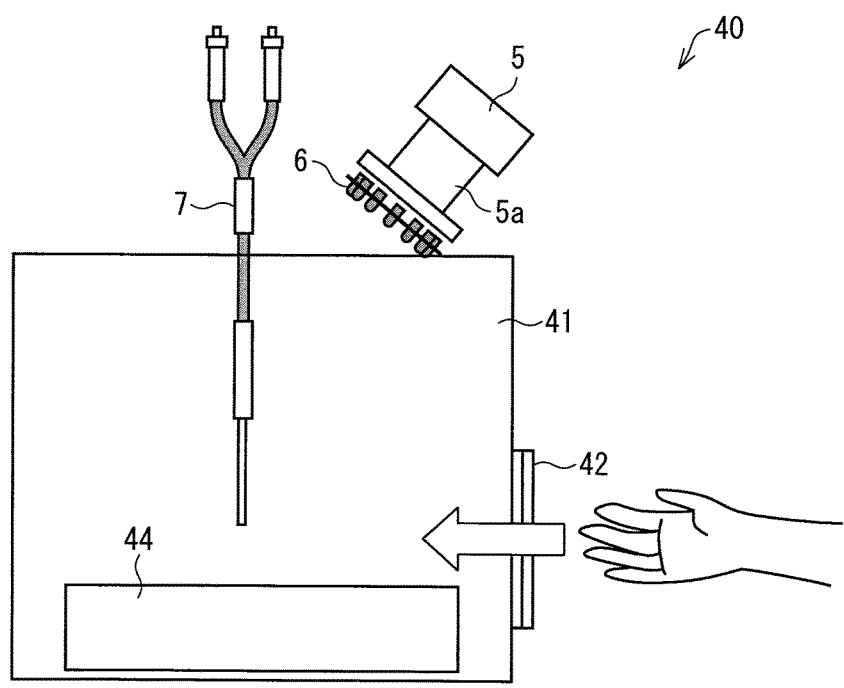
FIG. 13 is a view illustrating a modification in which locations of a camera and a blood vessel visualizing light source in the measurement device are modified.

Note that, as illustrated in FIG. 13, the camera 5 and the blood vessel visualizing light source 6 can be located in a state of being tilted with respect to the top surface of the image capturing housing 41. FIG. 13 is a view illustrating a modification in which locations of the camera 5 and the blood vessel visualizing light source 6 are modified.

An opening 42, through which a target measurement part of a test subject is to be inserted is created on a side surface of the image capturing housing 41. A plurality of valvate members 43, each made from a material which blocks ambient light and has flexibility, are provided on an inner periphery of the opening 42. In a case where the target measurement part is inserted into the opening 42, the plurality of valvate members 43 are bent inwardly toward the image capturing housing 41 in accordance with this insertion of the opening 42.

By thus providing the plurality of valvate members 43, it is possible to prevent (i) ambient light from entering the image capturing housing 41 and (ii) dust and dirt from entering the image capturing housing 41 while the target measurement part is inserted into the opening 42.

The probe 7 is inserted from the top surface of the image capturing housing 41 into the image capturing housing so as to be substantially perpendicular to the image capturing housing 41. The probe 7 can be moved in a direction perpendicular to the top surface of the image capturing housing 41 by an operation section (not shown).

Two other ends of the probe 7 are connected to the excitation light source 9 and the detector 10, as in the measurement device 1.

The arm pillow 44 is a rest for fixing a location of the target measurement part with respect to an end of the probe 7. It is preferable that, on a surface of the arm pillow 44, a recessed or protruding part which defines a place where the target measurement part is placed. For example, a protruding part, with which a fingertip or an elbow can be brought into contact, can be provided. Alternatively, a recess having a shape like a wrist can be provided.

A size and a shape of the arm pillow 44 are not particularly limited. For example, a rectangular parallelepiped of 12 cm×18 cm×5 cm can be used as the arm pillow 44.

Sections of the measurement device 40 are connected to the control device 20 so as to be controlled by the control device 20, which is similar to the measurement device 1.

(Effect of Measurement Device 40)

According to the measurement device 40, the probe 7 can be moved in a perpendicular direction. However, unlike the measurement device 1, the probe 7 cannot be three-dimensionally operated. In a case where the target measurement part is placed on the arm pillow 44, the end of the probe 7 is located at a location identical to locations of the target measurement part in a plurality of measurement opportunities. This makes it possible for identical locations to be irradiated with excitation light in the plurality of measurement opportunities.

Note that, in the measurement device 40, a distance between the end of the probe 7 and the surface of the target measurement part can be adjusted by use of functions of the area calculation section 24 and the distance calculation section 25. Also note that the control device 20 connected to the measurement device 40 does not need to include the two-dimensional coordinate calculation section 22 and the angle calculation section 23.

[Embodiment 3]

Figure 14:
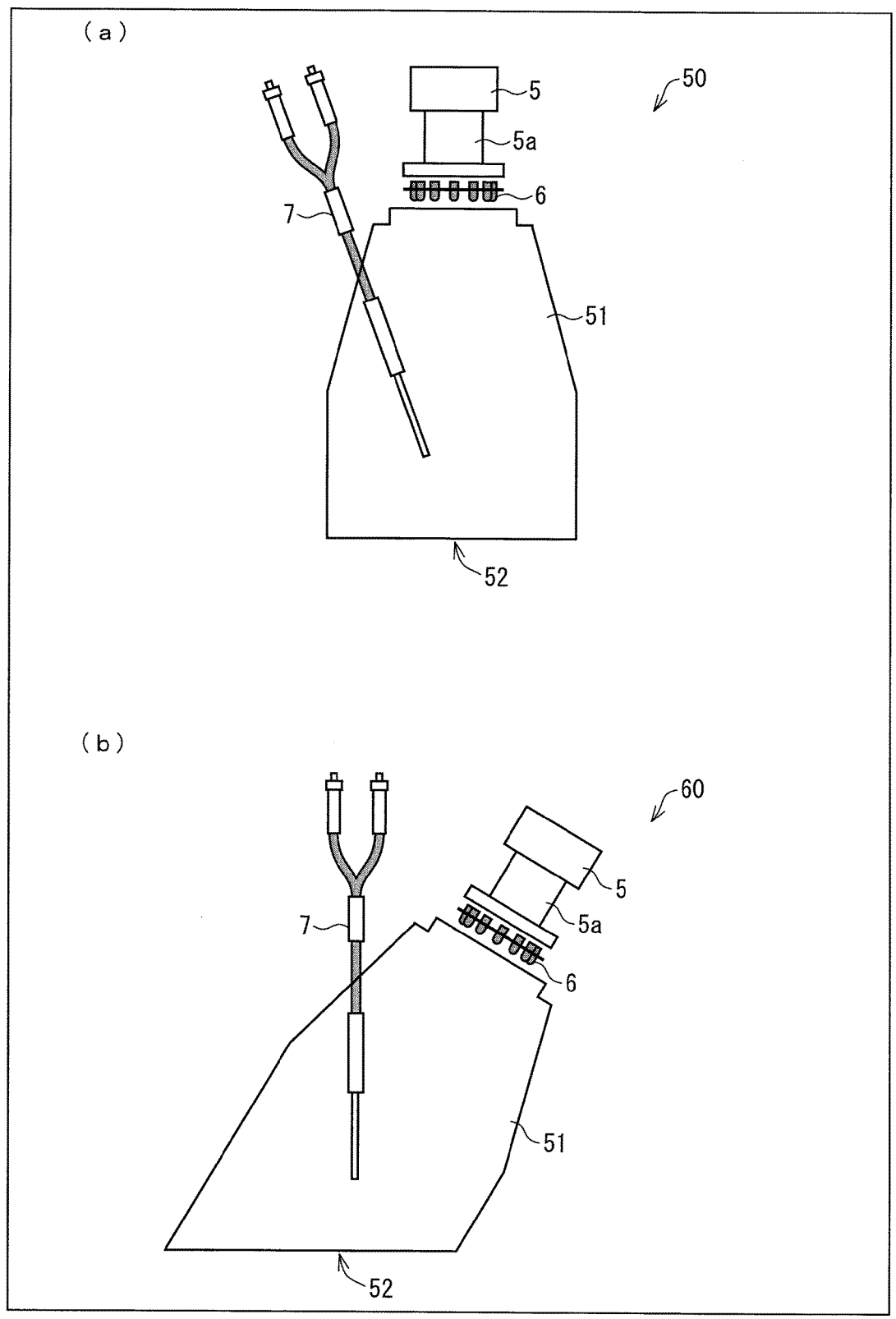
FIG. 14(a) and (b) of FIG. 14 are cross-sectional views each illustrating a configuration of a portable measurement device in accordance with a still another embodiment of the present invention.

Embodiment 3 of the present invention will be described below with reference to FIG. 14 and FIG. 15. Note that sections having the like functions as the figures described in Embodiments 1 and 2 are denoted by the like reference signs and the detailed description thereof is omitted. In Embodiment 3, a portable measurement devices 50 and 60 will be described.

A measurement device of the present invention can be realized as a portable measurement device. (*a*) and (*b*) of FIG. 14 are cross-sectional views illustrating configurations of the respective measurement devices 50 and 60. As illustrated in (*a*) and (*b*) of FIG. 14, each of the measurement devices 50 and includes an image capturing housing (light-shielding section) 51. The image capturing housing 51 is a hollow member made from a light-shielding material which is identical to that of the image capturing housing 4. A height of the image capturing housing 51 in the measurement device 50 is, for example, 9 cm.

The image capturing housing 51 has an opening 52 on its bottom part, and is brought into contact with a target measurement part. This causes a closed image capturing space to be secured.

A camera 5 and a blood vessel visualizing light source 6 are provided on a top surface of the image capturing housing 51. A camera axis of the camera 5 can be perpendicular to a plan including the opening 52 as illustrated in (*a*) of FIG. 14. Alternatively, the camera axis can be tilted with respect to the plan including the opening 52 as illustrated in (*b*) of FIG. 14. The same applies to an angle of a probe 7.

As illustrated in FIG. 15, the portable measurement devices 50 and 60 can be connected to a small portable terminal 70 instead of connecting to the control device 20. Examples of the portable terminal 70 encompass mobile phones, PDAs (personal digital assistants), and portable game machines. FIG. 15 is a view illustrating a state in which the portable measurement device 50 or 60 is connected to the portable terminal 70. In a configuration illustrated in FIG. 15, an excitation light source 9 and a detector 10 are provided in the image capturing housing 51. Three probes 7 are also illustrated in FIG. 15. The number of the probes 7 can be, however, one probe or more probes.

In the measurement devices 50 and 60, a real-time image captured by the camera 5 and an image captured when a previous measurement has been made are displayed on a display section 71 of the portable terminal 70. That is, the portable terminal 70 causes a storage section to store the image in which a target measurement part (measured part) irradiated with excitation light has captured in a first measurement opportunity. And, the display section 71 displays not only the real-time image captured by the camera 5 but also the image stored in the storage section, from a second measurement opportunity.

With the configuration, by watching a first captured image displayed on the display section 30, a test subject can know where to locate the end of the probe 7. By comparing a real-time captured image with the first captured image, it is possible to easily locate ends of the probes 7 at irradiation locations of the first measurement opportunity. This makes it easier to irradiate identical locations with excitation light in a plurality of measurement opportunities.

According to the measurement devices 50 and 60, locations of the ends of the probes 7 (i.e., locations irradiated with excitation light) are changed by changing a location of the image capturing housing 51 with respect to the target measurement part.

[Measurement Result Processing Device]

(Technical Problem)

A method disclosed in Patent Literature 1 further causes the following problem.

According to the method disclosed in Patent Literature 1, it is necessary to have expertise and perform complicated calculations in order to read a feature relating to existence of and a state of a disease from an obtained fluorescence spectrum. It is therefore difficult for a general user who does not have any special knowledge to understand a measurement result. This causes a problem that the measurement device could not be provided, to a general user, as a tool for individuals' health managements and as a tool for preventing diseases.

The present invention has been made in view of the aforementioned problem, and another object of the present invention is to provide (A) a measurement result processing device, (B) a measurement system, (C) a method of processing measurement result, and (D) a control program each of which (A) through (D) provides, as information which can be easily understood without any special knowledge, a measurement result obtained by a measurement system for measuring chemical substances by use of a radiation property obtained by use of excitation light, and (E) a recording medium in which the control program is recorded.

(Means for Solving Problem)

In order to attain the aforementioned object, the measurement result processing device of the present invention includes: feature extraction means for extracting a fluorescence characteristic of fluorescence emitted from a target measurement part, which fluorescence is obtained by irradiating, with excitation light, a part serving as the target measurement part of a body (living body) of a test subject; substance amount specifying means for specifying an amount of fluorescent substances contained in the target measurement part on the basis of the fluorescence characteristic extracted by the feature extraction means; and damage degree determination means for determining a damage degree indicative of a degree of damage received by the target measurement part or a part of the target measurement part on the basis of the amount of fluorescent substances specified by the substance amount specifying means.

In order to attain the aforementioned object, a measurement system of the present invention includes: a measurement device for acquiring measurement data of fluorescence generated by irradiating a target measurement part of a test subject (living body) with excitation light; and any one of the measurement result processing devices, which processes the measurement data acquired by the measurement device, said measurement device including: a light-shielding section for shielding environment light which is directed toward the target measurement part of the test subject; an excitation light source for irradiating the target measurement part of the test subject with excitation light; and a detector for generating the measurement data by analyzing the fluorescence generated by irradiating the target measurement part with the excitation light.

In order to attain the aforementioned object, a method of processing measurement result in accordance with the present invention includes the steps of: (A) extracting a fluorescence characteristic in fluorescence generated by a target measurement part obtained by irradiating, with excitation light, a part serving as the target measurement part of a body (living body) of a test subject; (B) specifying an amount of fluorescent substances contained in the target measurement part on the basis of the fluorescence characteristic extracted in the step (A); and (C) determining a damage degree indicative of a degree of damage received by the target measurement part or a part of the target measurement part on the basis of the amount of fluorescent substances specified in the step (B).

With the configuration, the substance amount specifying means outputs a target amount of fluorescent substances on the basis of a fluorescence characteristic obtained by measuring the target measurement part of the test subject, and in addition, the damage degree determination means outputs the damage degree indicative of a degree of damage of the target measurement part on the basis of the amount of fluorescent substances.

An amount of fluorescent substances, serving as a measurement result, is often expressed by a numerical value by use of a unit or an amount which is not used so much in daily life, which is similar to a case where amounts of other chemical substances are expressed. Accordingly, in a case where the amount of fluorescent substances is outputted, it is difficult for a user with poor knowledge of chemistry to lead to some conclusions by analyzing the measurement result or to understand a state of a test subject (target measurement part).

On the contrary, the present invention can replace the amount of fluorescent substances of the measurement result with a damage degree, and output the damage degree. The damage degree means a value indicative of how much damage a target measurement part receives, and can more directly indicate a state of a test subject (target measurement part) than a numerical value indicative of an amount of chemical substances.

The measurement result processing device outputs the damage degree serving as an imaginable indicator indicative of a state of a test subject (target measurement part). It has been difficult for a general user who does not have a special knowledge to understand a measurement result, however, the present invention can provide the measurement result as information which the general user can easily understand.

It is therefore possible to provide, to a user, the measurement result as information that a user can easily understand without any special knowledge. The measurement result is obtained in a measurement system of chemical substances, in which measurement system a radiation property obtained by use of excitation light is used.

[Embodiment 4]

Embodiment 4 of the present invention will be described below with reference to FIG. 17 through FIG. 31. Embodiment 4 will discuss a measurement system 1100 for measuring an amount of AGEs accumulation (amount of fluorescent substances) of a target measurement part by analyzing a fluorescence spectrum (fluorescence property) obtained by irradiating, with excitation light, a part (hereinafter, referred to as "target measurement part") of a living body to be measured (hereinafter, referred to as "test subject"). However, application of the measurement system of Embodiment 4 of the present invention is not limited to humans, and a measurement can therefore be made with respect to various living bodies (including dogs and cats) as a test subject.

[Configuration of Measurement System 1100]

Figure 18:
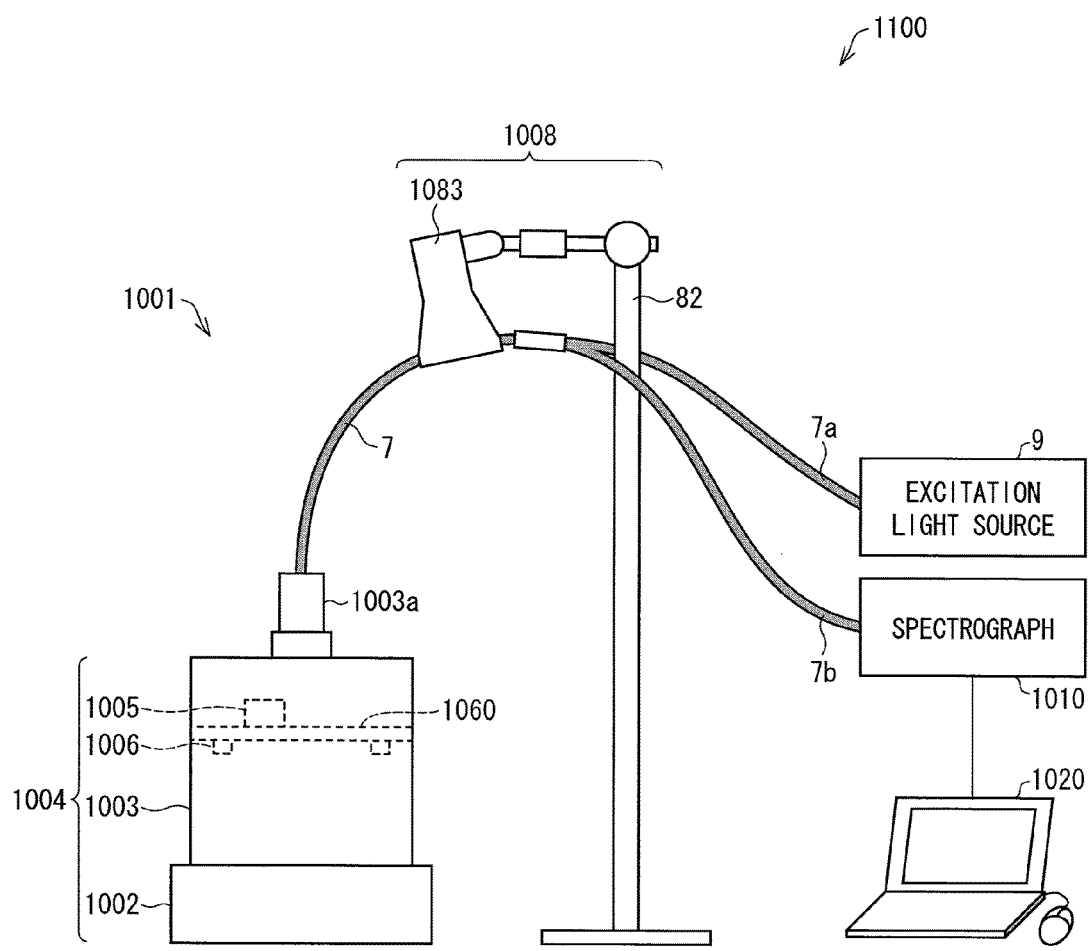
FIG. 18 is a schematic view illustrating a configuration of a measurement system in accordance with still another embodiment of the present invention.

FIG. 18 is a schematic view illustrating a configuration of the measurement system 1100 in accordance with Embodiment 4 of the present invention. As illustrated in FIG. 18, the measurement system 1100 includes a measurement device 1001 and a control device 1020.

The measurement device 1001 is a measurement device in which (i) a specific part of a target measurement part, such as an arm, a wrist, a finger, or a palm of a test subject, is irradiated with excitation light, (ii) fluorescence generated by irradiating the specific part is received, and then (iii) an intensity of the fluorescence thus received is measured (fluorescence spectrum is detected). An amount of substance accumulated in a living body can be measured on the basis of the fluorescence spectrum.

The specific part means: an artery; a vein; a combination of an artery and a vein (i.e., blood vessel); and a skin where no blood vessel exists. In Embodiment 4, the control device 1020 for controlling the measurement device 1001 has a function (measurement operation assisting function) of assisting an operation performed by a user (an operator of the measurement device 1001 and the control device 1020 and/or a test subject) on the basis of a captured image in which the target measurement part is captured so that a blood vessel in the proximity of a wrist of a test subject is irradiated with excitation light.

The control device 1020 for controlling sections of the measurement device 1001 also serves as an information processing device for processing various kinds of information obtained by the measurement device 1001. Examples of the control device 1020 encompass a general-purpose personal computer and a dedicated terminal device. Examples of the various kinds of information that the control device 1020 obtains from the measurement device 1001 encompass: an image of a target measurement part captured by the measurement device 1001; and a fluorescence spectrum (fluorescent intensity) of the target measurement part, which is measured by the measurement device 1001.

[Configuration of Measurement Device 1001]

As illustrated in FIG. 18, the measurement device 1001 includes: an image capturing housing 1004, a probe 7, a probe support section 1008 for supporting the probe 7, an excitation light source 9, and a spectrograph 1010. The image capturing housing 1004 is configured such that a measurement target housing section 1003 is provided on a bottom section 1002, and is provided so as to house a target measurement part.

(Image Capturing Housing 1004)

The image capturing housing (light-shielding section) 1004 is provided for efficiently obtaining, by use of the probe 7, fluorescence generated by irradiating a target measurement part with excitation light. The image capturing housing 1004 functions as a light-shielding section for (i) shielding ambient light which is directed toward the target measurement part (here, wrist) and (ii) preventing strong reflection of the excitation light. The image capturing housing 1004 is configured such that the measurement target housing section 1003 is provided on the bottom section 1002. The measurement target housing section 1003 houses a camera section 1005 for capturing a target measurement part, a blood vessel visualizing light source 1006, and an end of the probe 7 for irradiating the target measurement part with excitation light or for receiving fluorescence.

The measurement target housing section 1003 of the image capturing housing 1004 can be made from plastics such as PP (polypropylene), light-shielding polystyrene, polyethylene, or polyethylene-telephthalate. Instead of those resins, the measurement target housing section 1003 can be made from any materials such as papers on which aluminum foil is attached so as to face an inner wall of the image capturing housing 1004, metals, and woods. Light-shielding plastics are preferable in terms of transportability, economical efficiency, and durability.

The bottom section 1002 of the image capturing housing 1004 functions as a support section which stably supports the measurement target housing section 1003 even in a case where the target measurement part (wrist) is inserted into the measurement target housing section 1003 from a side surface of the bottom section 1002. A material for the bottom section 1002 is not particularly limited. However, it is preferable that the bottom section 1002 (i) has a light-shielding property, like the measurement target housing section 1003, and (ii) is made up of a pad made from a silicone resin having high adhesiveness to a human body.

Figure 19:
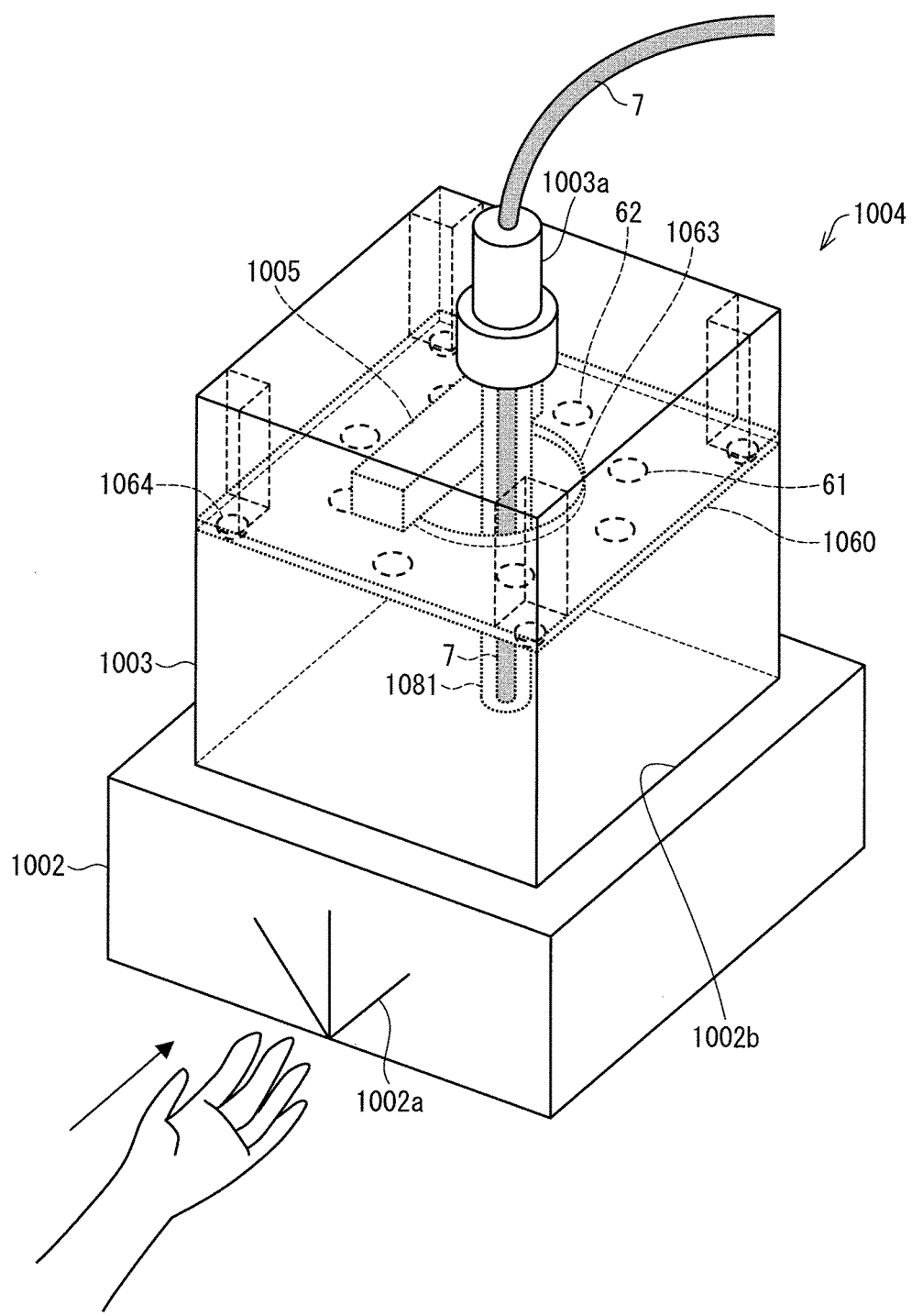
FIG. 19 is a perspective view illustrating an image capturing housing.
Figure 20:
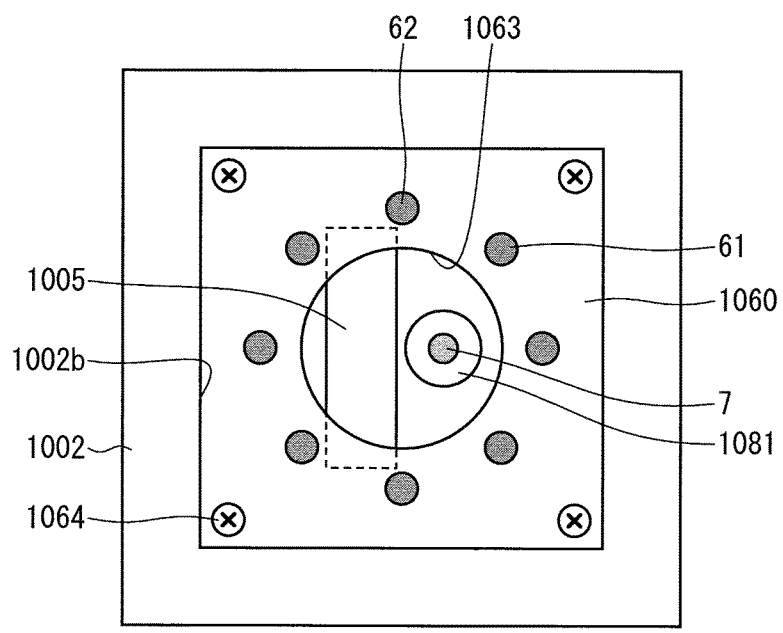
FIG. 20 is a plan view illustrating inside of an image capturing housing viewed from a bottom side.

FIG. 19 is a perspective view illustrating the image capturing housing 1004. FIG. 20 is a plan view illustrating inside of the image capturing housing 1004 viewed from a bottom section 1002 side.

As illustrated in FIG. 19, an insertion port 1002a through which a target measurement part (wrist) is to be inserted is provided in a side surface of the bottom section 1002. Further, as illustrated in FIG. 19 and FIG. 20, an opening 1002b is created in a top surface of the bottom section 1002, and the opening 1002b and the measurement target housing section 1003 are communicated with each other. Thus, a space is secured for capturing a target measurement part.

A size of the measurement target housing section 1003 is not limited to a specific one, provided that each assumed target measurement part can be housed.

Note, however, that it is preferable that the measurement target housing section 1003 is as small as possible in a case where the measurement device 1001 is realized by a device having excellent transportability and portability. In order to downsize the measurement device 1001, (i) the image capturing housing 1004 and the excitation light source 9 and (ii) the image capturing housing 1004 and the spectrograph 1010 can be directly connected to each other via respective sections such as hollow screws, instead of being connected via the probe 7. Small devices having excellent transportability can be also employed as respective of the excitation light source 9 and the spectrograph 1010.

Note that, in a case where (i) assumed target measurement parts are large and (ii) the measurement target housing section 1003 needs to be upsized, it is preferable that the measurement target housing section 1003 is constituted by decomposable several units. This causes an improvement in portability of the measurement target housing section 1003 because such several units can be assembled together only when needed whereas can be disassembled and stored when not used. It is desirable that the measurement target housing section 1003 has a configuration, such as an inset configuration, which allows the measurement target housing section 1003 to be easily connected to the bottom section 1002.

As illustrated in FIG. 18 to FIG. 20, a substrate 1060 on which various electronic components are mounted is fixed, in the measurement target housing section 1003, by screws 1064, and a space in the measurement target housing section 1003 is divided into an upper part and a lower part by the substrate 1060. The camera section 1005 and the blood vessel visualizing light source 1006 (near-infrared LEDs 61 and red LEDs 62) are mounted on an upper surface of and a lower surface of the substrate 1060 so as to be housed in the upper part of and the lower part of the space, respectively.

As illustrated in FIG. 19 and FIG. 20, the substrate 1060 has an opening 1063. Accordingly, as illustrated in FIG. 19, the probe 7, which is inserted into a probe insertion port 1003a provided on an upper surface outside the measurement target housing section 1003, is penetrated through the upper part and the lower part of the space of the measurement target housing section 1003. The end of the probe 7 can reach the target measurement part inserted into the insertion port 1002a of the bottom section 1002. Furthermore, the opening 1063 allows the camera section 1005 mounted on the substrate 1060 in the upper part of the space to capture the target measurement part which is housed in the lower part of the space.

(Camera Section 1005)

The camera section 1005 is an image capturing device for capturing a target measurement part, and examples of camera 5 encompass CCD (charge coupled device) cameras, CMOS (complementary metal-oxide-semiconductor) cameras, and other image capturing devices.

The camera section 1005 includes a lens (not shown), and can enlarge or reduce an image by adjusting the lens. The lens can be directly and manually adjusted by a user, or can be adjusted via the control device 1020.

An image captured by the camera section 1005 is supplied to the control device 1020, and is displayed on a display section of the control device 1020.

Note that, in some cases, a commercially available digital camera provides an IR cut filter in front of an image capturing element. The IR cut filter is a filter through which visible light is to be transmitted and to from which infrared rays are reflected. However, the commercially available digital camera can be also arranged so as to remove the IR cut filter and add a band pass filter through which only light in a near-infrared region can be passed. In this case, it is necessary further provide, in front of the probe 7, a band pass filter through which light having a wavelength of about 450 nm is to be transmitted. This configuration does not need a housing of the camera. It is therefore possible to downsize a measurement device.

(Blood Vessel Visualizing Light Source 1006)

The blood vessel visualizing light source 1006 is an illuminating device for irradiating a target measurement part by switching between multiple kinds of illumination light (specifically, red light and infrared light) each having whose respective wavelengths different from each other. The blood vessel visualizing light source 1006 is provided in the measurement target housing section 1003 and near the camera section 1005. Examples of the blood vessel visualizing light source 1006 encompass Multi-Wavelength LED KED694M31D (manufactured by Kyosemi Corporation). More specifically, as illustrated in FIG. 19 and FIG. 20, the blood vessel visualizing light source 1006 is realized by the plurality of near-infrared LEDs 61 and the red LEDs 62. The plurality of near-infrared LEDs 61 and the plurality of red LEDs 62 can cause an image to be visualized by use of an absorption property of oxygenated/reduced hemoglobin existing in a blood vessel. The near-infrared LEDs 61 and red LEDs 62 are alternately provided around the opening 1063 created in the substrate 1060. The substrate 1063 is attached to the inside of the measurement target housing section 1003 by use of the screws 1064. A center of the opening 1063 substantially corresponds to a center of an optical axis of the camera section 1005. This causes the blood vessel visualizing light source 1006 not to hinder the camera section 1005 from capturing the target measurement part.

The near-infrared LED 61 is a light source which emits light having a wavelength of about 945 nm (890 nm to 1010 nm) in the near-infrared region. By irradiating a skin surface with near-infrared light, it is possible to detect oxygenated hemoglobin. Accordingly, veins can be visualized.

The red LED 62 is a light source which emits light having a wavelength of about 660 nm (620 nm to 700 nm) in a red region. By irradiating a skin surface with red light, it is possible to detect reduced hemoglobin. Accordingly, arteries can be visualized.

Switching between a state in which the near-infrared LEDs 61 are turned on and a state in which the red LEDs 62 are turned on can be carried out via, for example, the control device 1020.

As such, in the measurement device 1001, by using the blood vessel visualizing light source 1006, it is possible to (i) visualize a capillary difficult to view by naked eyes and (ii) control the control device 1020 to display the image obtained from the camera section 1005. It is therefore possible to assist a user so that the user can specify a measurement location without considering a size of a blood vessel or a distance of the blood vessel from a skin surface. It is further easy to distinguish between an artery and a vein.

(Probe 7)

The probe 7 functions as (A) an excitation light irradiation section which irradiates, with excitation light, a specific part (e.g., blood vessel) on a skin surface of the target measurement part in a plurality of measurement opportunities and (B) a light receiving section which receives fluorescence generated by irradiating the specific part with excitation light. That is, the probe 7 is a combination of the excitation light irradiation section and the light receiving section.

(a) and (b) of FIG. 5 are views illustrating cross-sectional shapes of the probe 7. Since FIG. 5 has been described in Embodiments 1 through 3, description of FIG. 5 will be omitted.

(Probe Support Section 1008)

The probe support section 1008 is a support mechanism for stably keeping a distance between the end of the probe 7 and the surface of the target measurement part at the irradiation location (specific part). The probe support section 1008 includes: a probe guide 1081 (FIG. 19, FIG. 20) for housing the end of the probe 7; the support 82; and a clamp 1083 (FIG. 18).

The probe guide 1081 is a tubular member into which the probe 7 is to be inserted. It is difficult to accurately locate the end of the probe 7 having flexibility. It is therefore preferable that, while the end of the probe 7 is being inserted into the probe guide 1081, a location and an angle of the end of the probe 7 are adjusted by adjusting a location and an angle of the probe guide 1081.

As illustrated in FIG. 19 and FIG. 20, in Embodiment 4, the probe guide 1081 is inserted into the probe insertion port 1003a provided in the measurement target housing section 1003 or is coupled to the probe insertion port 1003a in the measurement target housing section 1003.

The support 82 and the clamp 1083 are provided between (A) the excitation light source 9 and the spectrograph 1010 and (B) the image capturing housing 1004 in order to support the probe 7 extending from the excitation light source 9 and the spectrograph 1010 to the image capturing housing 1004. In a case where the probe 7 having flexibility is inserted through the probe insertion port 1003a provided on the top surface of the measurement target housing section 1003, it is sometimes difficult to stabilize a direction of the end of the probe 7, depending on a positional relationship between (A) the excitation light source 9 and the spectrograph 1010 and (B) the image capturing housing 1004. In view of the circumstances, the clamp 1083, which is connected to the support 82 and whose height is adjusted, holds the probe 7. This allows the end of the probe 7 to be stably inserted into the measurement target housing section 1003.

(Excitation Light Source 9)

The excitation light source 9 is a light source for generating excitation light which projects a target measurement part. In Embodiment 4, the excitation light is light which detects fluorescence derived from AGEs, and has a wavelength range appropriate for measuring AGEs. Examples of the kinds of light sources serving as the excitation light source 9 encompass (a) bulb-type light sources such as a halogen light source and a xenon light source, (b) an LED, and (c) an LD.

There are known about twenty kinds of AGEs whose structures have become clear. Some of them emit fluorescence upon irradiation with excitation light.

For example, CLF (collagen-linked fluorescence) is fluorescence caused by AGEs binding to collagen, and is used as a general index for total production of AGEs and accompanying collagen crosslink.

Representative examples of AGEs are pentosidine and vesperlysine. Pentosidine is a fluorescent substance which becomes stable after acid hydrolysis, and has a chemical structure in which lysine and arginine each being equimolar to pentose are cross-linked with each other. It is reported that pentosidine increases in development of diabetes and the end stage of nephropathy. Vesperlysine is acid hydrolyzed and is then isolated as a main fluorescent substances from acid-hydrolyzed AGE-bovine serum albumin (BSA), and has a structure in which two molecules of lysine are cross-linked with each other.

The excitation light source 9 can project, for example, ultraviolet radiation (wavelength: 230 nm to 365 nm) or visible light (wavelength: 405 nm). In a case where excitation light having such a wavelength is projected toward a specific part of a target measurement part (e.g., blood vessel), fluorescence can be obtained from accumulated substance on a blood vessel wall of an irradiation location. The fluorescence thus obtained is guided toward the spectrograph 1010 and is then analyzed by the spectrograph 1010.

(Spectrograph 1010)

The spectrograph 1010 receives, via the reflection fiber 7b of the probe 7, fluorescence generated by irradiating a specific part with excitation light, and measures wavelengths of the fluorescence and an intensity in each of the wavelengths. That is, the spectrograph 1010 detects wavelengths of fluorescence and respective intensities of the fluorescence. Spec. of the spectrograph 1010 is not particularly limited, provided that the spectrograph 1010 can detect light having a desired range of wavelength. However, semiconductor detectors are preferable in terms of transportability of the measurement device 1001.

The spectrograph 1010 detects and analyzes the fluorescence, and then transmits measurement data, which is an electric signal into which an analysis result is converted, to the control device 1020 via a communication cable or via wireless communication means. In Embodiment 4, the control device 1020 or other personal computers can control the spectrograph 1010 via a communication cable, and can carry out control of, for example, setting of total time for detection and fetching of data. In Embodiment 4, for example, VisualSpectra2.1Sr can be used as spectrograph control software installed in the control device 1020.

The control device 1020 controls the spectrograph 1010, and processes measurement data received from the spectrograph 1010. It was found that the fluorescent intensity of the target measurement part, which is obtained from the measurement data, is in proportion to an abundance of accumulated substances in a blood vessel of the target measurement part. That is, the fluorescent intensity increases as the abundance of substances accumulated on a blood vessel increases, whereas decreases as the abundance of substances accumulated on a blood vessel decreases.

In view of the circumstances, the control device 1020 measures an amount of fluorescent-substance accumulation (amount of fluorescent substances), such as AGEs accumulated on a blood vessel wall of the target measurement part, on the basis of the fluorescent intensity thus obtained. Then, the control device 1020 converts a result of this measurement into information which is easy for a user to understand, and outputs the information. That is, the control device 1020 is a measurement result processing device which realizes a function (hereinafter, referred to a "measurement result processing function") of (i) converting information indicative of an amount of fluorescent-substance accumulated on a blood vessel wall into an indicator in which a health condition can be recognized at a glance and (ii) showing the indicator to the user. The control device 1020 provides the user with the result of the measurement thus converted, by controlling, for example, a display section to display the result of the measurement. A configuration of the control device 1020 will be described below in detail.

[Configuration of Control Device 1020]

Figure 17:
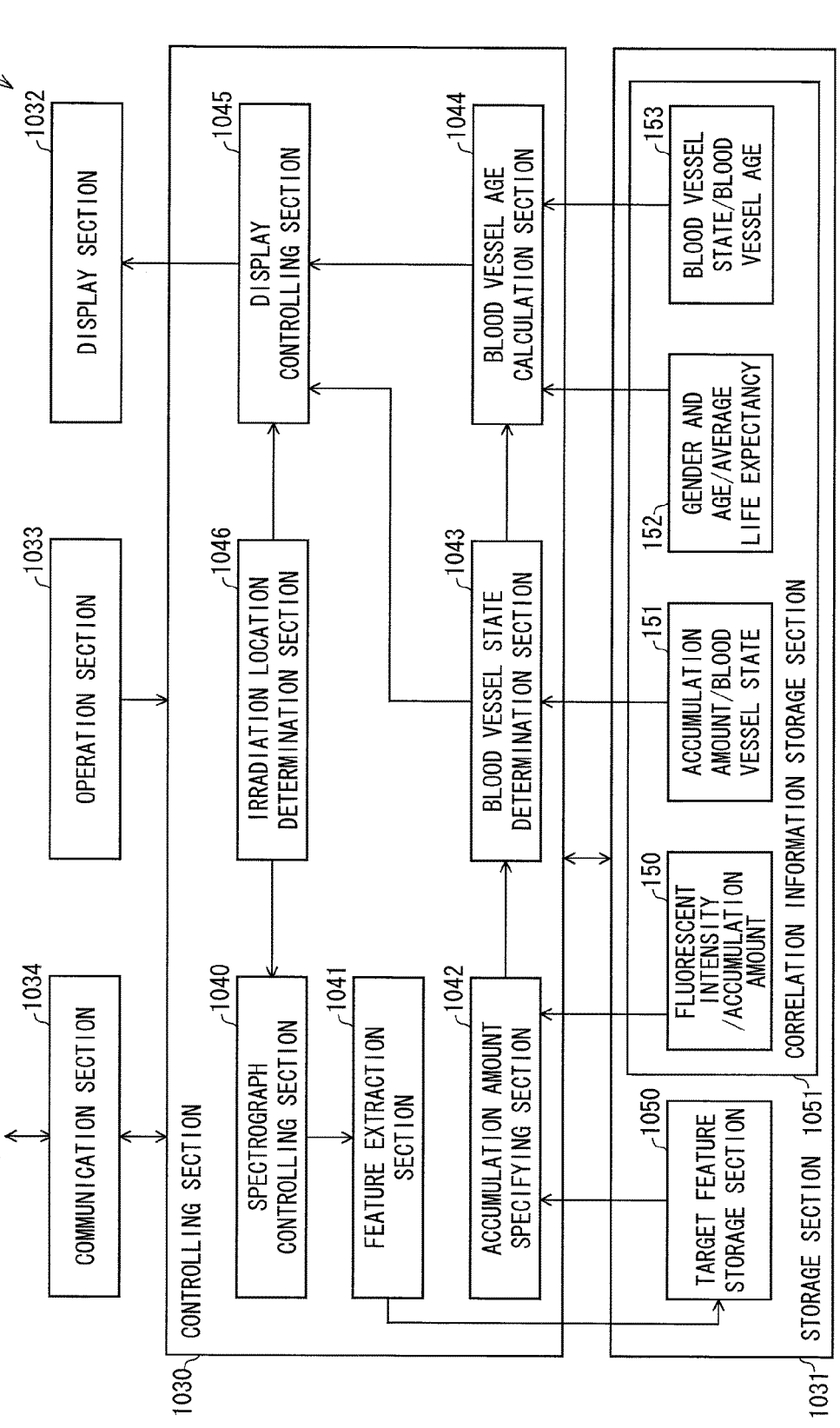
FIG. 17 is a block diagram illustrating a main configuration of a control device in accordance with still another embodiment of the present invention.

FIG. 17 is a block diagram illustrating a main configuration of the control device 1020 in accordance with Embodiment 4 of the present invention. As illustrated in FIG. 17, the control device 1020 in Embodiment 4 includes, a controlling section 1030, a storage section 1031, a display section 1032, an operation section 1033, and a communication section 34.

The display section 1032 displays (i) the various kinds of information that the control device 1020 obtains from the measurement device 1001, (ii) the various kinds of information stored in the control device 1020 in advance, (iii) the result of the measurement analyzed by the control device 1020, and (iv) an operation screen, as a GUI (graphical user interface) screen, via which a user operates the control device 1020. The display section 1032 is realized by a display device such as an LCD (liquid crystal display).

The operation section 1033 is a section via which an instruction signal is entered by the user so as to be supplied to the control device 1020. Examples of the operation section 1033 encompass appropriate input devices such as a keyboard, a mouse, a button, a touch panel, a touch sensor, a stylus, and a voice inputting section and voice recognizing section.

The communication section 34 is provided for communicating with an external device via wired or wireless communication network. In Embodiment 4, the communication section 34 communicates with the spectrograph 1010. Specifically, the communication section 34 receives various kinds of data, such as measurement data, from the spectrograph 1010, and transmits an instruction to the spectrograph 1010. The communication section 34 communicates with the excitation light source 9 and the blood vessel visualizing light source 1006 so as to control irradiation operations of respective light sources. Furthermore, the communication section 34 communicates with the camera section 1005 and acquires an image of a target measurement part (either a still image or a live view image) captured by the camera section 1005.

The storage section 1031 stores various kinds of data which is read out when the controlling section 1030 executes various functions of the control device 1020. The storage section 1031 is realized by, for example, a nonvolatile rewritable storage device. In particular, the storage section 1031 stores various programs and various kinds of data which are read out when the control device 1020 realizes the measurement operation assisting function and the measurement result processing function. Specifically, storage section 1031 includes a target feature storage section 1050 and a correlation information storage section 1051. Note that a control program and an OS program executed by the controlling section 1030 can be stored in a storage device such as a ROM (read only memory) (not illustrated), instead of the storage section 1031.

The controlling section 1030 is provided for carrying out overall control with respect to each section of the control device 1020. The controlling section 1030 includes, as function blocks, at least a spectrograph controlling section 1040, a feature extraction section 1041, an accumulation amount specifying section 1042, a blood vessel state determination section 1043, and a display controlling section 1045. The controlling section 1030 can further include, as a function block, a blood vessel age calculation section 1044 and an irradiation location determination section 1046.

Each of the function blocks of the controlling section 1030 can be realized by causing a CPU (central processing unit) to (i) read out a program in a RAM (random access memory) (not illustrated) etc., and (ii) execute the program stored in a storage device (not illustrated) realized by a ROM (read only memory) etc. or the storage section 1031.

The irradiation location determination section 1046 realizes the measurement operation assisting function of the control device 1020. The irradiation location determination section 1046 determines whether or not a positional relationship between the end of the probe 7 and a specific part of a target measurement part is appropriate. Specifically, the irradiation location determination section 1046 analyzes an image of the target measurement part and the probe 7, captured by the camera section 1005 in the measurement target housing section 1003, and determines whether or not the end of the probe 7 is located at a location where the specific part of the target measurement part can be appropriately irradiated.

In Embodiment 4, the target measurement part is a wrist of a test subject, and the specific part is a blood vessel (either an artery or a vein). The wrist of the test subject is irradiated with light projected from the blood vessel visualizing light source 1006 in the measurement target housing section 1003. This causes the blood vessel to be in a visualized state and excitation light to be projected from the end of the probe 7. As such, it is possible to visually confirm that a part irradiated with light is located at the end of the probe 7.

The irradiation location determination section 1046 analyzes the image, and then determines that the end of the probe 7 is located at an appropriate irradiation location in a case where the end is located above a blood vessel, whereas determines that the end is located at inappropriate irradiation location in a case where the end is not located above the blood vessel.

The spectrograph controlling section 1040 controls the spectrograph 1010 and acquires necessary data from the spectrograph 1010. For example, the spectrograph controlling section 1040 is realized by causing a CPU to read out and execute the VisualSpectra2.1Sr stored, as spectrograph control software, in the storage section 1031.

According to Embodiment 4, the spectrograph controlling section 1040 is configured to acquire the measurement data from the spectrograph 1010, in a case where (A) the irradiation location determination section 1046 determines that the positional relationship between the end of the probe 7 and the target measurement part is appropriate and (B) the spectrograph controlling section 1040 accepts an instruction to make a measurement from a user via the operation section 1033.

Note that it is preferable that the irradiation location determination section 1046 is configured to permits the spectrograph controlling section 1040 to acquire a fluorescence spectrum from the spectrograph 1010, only when the irradiation location determination section 1046 determines that the end of the probe 7 is located at an appropriate irradiation location. With the configuration, in a case where the end of the probe 7 is not located at an appropriate location, the irradiation location determination section 1046 does not allow the spectrograph controlling section 1040 to acquire a fluorescence spectrum from the spectrograph 1010. As such, it is possible to prevent the control device 1020 from processing a dishonest fluorescence spectrum. Note that, in a case where the fluorescent intensity (a peak or an average value of the fluorescent intensity) thus obtained is extremely small (e.g., 1000 a.u. or low), the spectrograph controlling section 1040 can feed back, to the sections of the control device 1020, a measurement error indicating that an adequate fluorescent intensity is not obtained even in a case where the irradiation location determination section 1046 permits the spectrograph controlling section 1040 to acquire a fluorescence spectrum from the spectrograph 1010. If there is the measurement error, the sections of the control device 1020 control the measurement device 1001 to carry out again processing of measuring the fluorescence of the target measurement part of the test subject. Note that the control device 1020 can output a message encouraging the user to make a measurement again. This makes it possible to prevent the control device 1020 from processing a fluorescence spectrum which may lead a wrong result because of an inadequate fluorescent intensity.

It is preferable that the irradiation location determination section 1046 supplies an image acquired from the camera section 1005 to the display controlling section 1045, so that the display section 1032 can display the image. This makes it possible that the user observes, on the basis of the image displayed on the display section 1032, a positional relationship between a current location of the end of the probe 7 and a blood vessel of the wrist, while the wrist is being housed in the measurement target housing section 1003. It is further preferable that the display section 1032 displays a live view image captured by the camera section 1005 in response to the irradiation location determination section 1046. Therefore, the user can appropriately adjust locations of the wrist or the probe 7 by moving the wrist or the probe 7 while the user is visually confirming the positional relationship between the end of the probe 7 and the blood vessel of the wrist.

It is preferable that the display controlling section 1045 controls, in response to the irradiation location determination section 1046, the display section 1032 to display (A) a message encouraging a user to adjust the end to a location of a blood vessel in a case where the end of the probe 7 is not located at an appropriate location, whereas (B) a message informing the user that the location is a right location and therefore the user should keep the right location in a case where the end is located at an appropriate location.

Therefore, the user can determine whether or not measurement can be started.

The display controlling section 1045 supplies, to the display section 1032, (i) the various kinds of information obtained by the control device 1020 and (ii) the data of the GUI screen as the video signal.

For example, the communication section 34 receives the image captured by the camera section 1005, and then supplies the image to the display section 1032 via the display controlling section 1045. The image is displayed on the display section 1032 so as to be visually confirmed by the user.

In accordance with an instruction of the irradiation location determination section 1046, the display controlling section 1045 supplies, to the display section 1032, a message which varies depending on a result determined by the irradiation location determination section 1046.

As is clear from the above, with the configuration including the camera section 1005 and the blood vessel visualizing light source 1006 of the image capturing housing 1004, the spectrograph controlling section 1040, the display controlling section 1045, and the irradiation location determination section 1046, it is possible to assist a measurement operation of a user (test subject and/or operator). An example of a display screen of the image and the message will be described below with reference to FIG. 21. Note that the display controlling section 1045 also supplies, to the display section 1032, a measurement result supplied from each of the blood vessel state determination section 1043 and the blood vessel age calculation section 1044 (later described). A specific example of the display screen of the measurement result will be described below with reference to other drawings.

Figure 21:
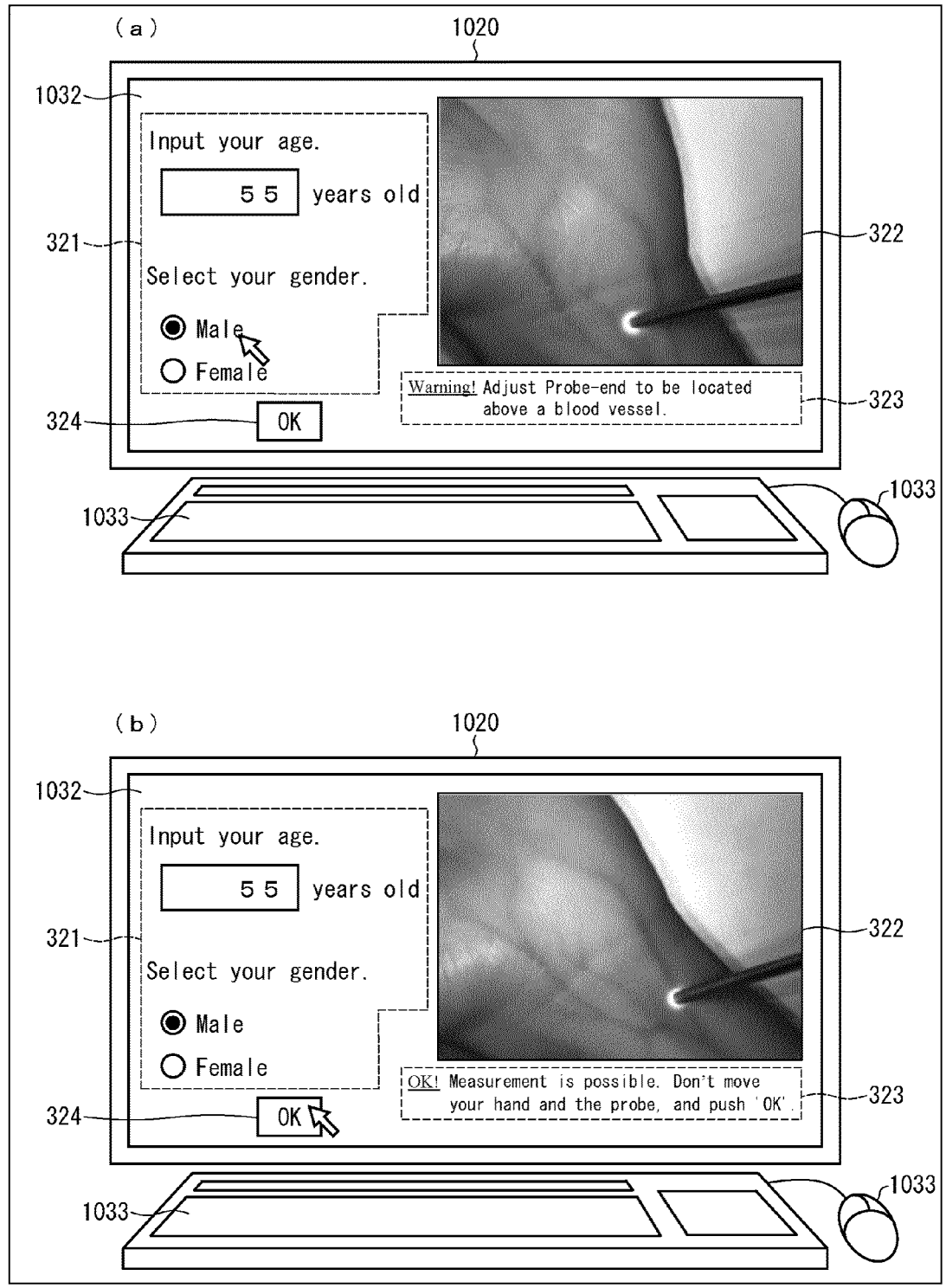
FIG. 21(a) and (b) of FIG. 21 are views each illustrating an example operation screen which is displayed on a display section of a control device and is used for operating a measurement device.

(a) and (b) of FIG. 21 are views each illustrating an example operation screen of the measurement device 1001, which operation screen is displayed on the display section 1032 of the control device 1020. Note that the operation screens illustrated in (a) and (b) of FIG. 21 do not intend to limit the present invention, and can be therefore appropriately designed in accordance with a function of the measurement device 1001 and a purpose of measurement.

As illustrated in (a) and (b) of FIG. 21, (i) a region 321 through which information on a test subject is to be entered, (ii) a region 322 where a live view image captured by the camera section 1005 is displayed, (iii) a region 323 where a message informing a user as to whether or not an irradiation location is appropriate is displayed, and (iv) an OK button 324 via which a measurement start (acquisition of fluorescence spectrum) is instructed, appear on the operation screen displayed on the display section 1032.

A user enters information on a test subject (actual age and gender) via the region 321 by operating the operation section 1033 constituted by a keyboard, a mouse, etc. The user also clicks the OK button 324 via which a measurement start is instructed.

In a case where the end of the probe 7 is not located above a blood vessel, the display controlling section 1045 controls the region 323 to display a message encouraging the user to adjust a location of the end to a location of the blood vessel in accordance with a result determined by the irradiation location determination section 1046 (see (a) of FIG. 21). This allows the user to adjust the location of the blood vessel to the end of the probe 7, by moving a wrist of the test subject while watching a live view image displayed on the region 322. It is preferable that the OK button 324 cannot be selected in a state illustrated in (a) of FIG. 21.

As illustrated in (b) of FIG. 21, in a case where the irradiation location determination section 1046 determines that the end of the probe 7 is located above the blood vessel, the display controlling section 1045 controls the region 323 to display a message informing a user that the location is a right location and therefore the user should keep the right location in accordance with the result determined by the irradiation location determination section 1046. Furthermore, the display controlling section 1045 controls the display section 1032 to display the OK button 324 so that the OK button 324 can be selected by a user. Then the display controlling section 1045 controls the display section 1032 to display a message encouraging a user to start measurement.

In a case where the OK button 324 is selected, the spectrograph controlling section 1040 accepts an instruction signal, and then acquires measurement data from the spectrograph 1010.

The feature extraction section 1041 analyzes the measurement data acquired from spectrograph 1010, and then extracts a feature contained in the measurement data.

Specifically, according to Embodiment 4, in a case where a target measurement part is irradiated with excitation light which has a certain excitation light wavelength (Ex) and is projected from the excitation light source 9, the measurement data supplied from the spectrograph 1010 contains (A) fluorescence wavelengths (Em) of fluorescence radiated from the target measurement part and (B) a spectrum indicative of intensities of the respective fluorescence wavelengths. The feature extraction section 1041 detects a peak intensity having a certain wavelength range in the spectrum, and extracts, as a feature of the target measurement part, a peak fluorescent intensity. In Embodiment 4, the feature extraction section 1041 extracts, as the peak fluorescent intensity, a maximum value in a wavelength range (434.664 nm to 474.308 nm).

Figure 22:
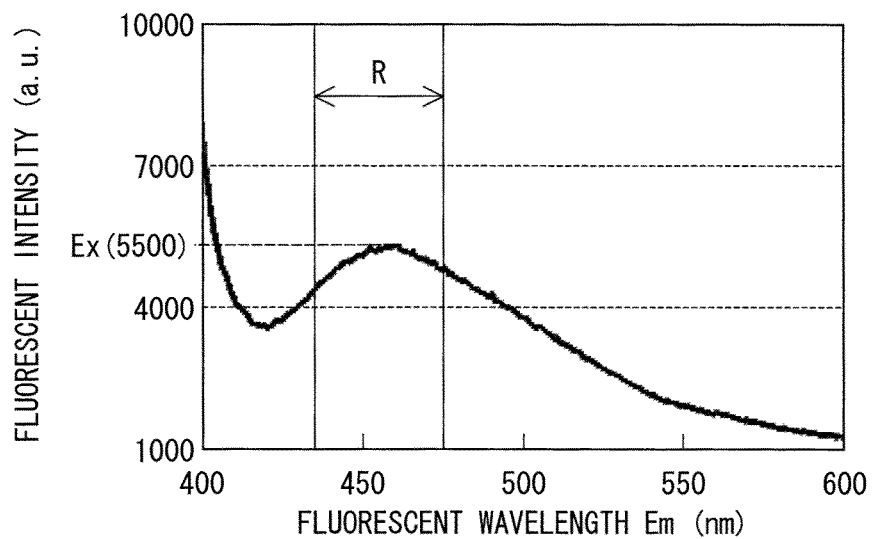
FIG. 22 is a view showing (A) a specific example of a fluorescence spectrum obtained from a spectrograph and (B) peak fluorescence intensity extracted as a feature.

FIG. 22 is a view illustrating (A) a specific example of a fluorescence spectrum acquired from the spectrograph 1010 and (B) a fluorescent intensity extracted as a feature.

In a graph of the fluorescence spectrum illustrated in FIG. 22, an abscissa indicates a wavelength Em of fluorescence radiated from a target measurement part, and an ordinate indicates a fluorescent intensity of the wavelength Em. As described above, the feature extraction section 1041 acquires, as a feature, a maximum value of fluorescent intensities in a certain wavelength range R (e.g., 434.664 nm to 474.308 nm) of fluorescence. In the example of FIG. 22, the fluorescent intensity Ex "5500 (a.u.)" is acquired as the feature.

In Embodiment 4, the feature extraction section 1041 causes the information on the test subject (region 321 of FIG. 21) and the fluorescent intensity (FIG. 22) to be stored by the target feature storage section 1050 so as to be associated with each other. Note that the information on the test subject is entered before the measurement is started and the peak fluorescent intensity is extracted from the fluorescence spectrum obtained from the target measurement part of the test subject. Alternatively, the target feature storage section 1050 can store the fluorescence spectrum of FIG. 22 as it is.

The peak fluorescent intensity Ex (nm) and the information on the test subject, such as age, gender, and test subject ID (if necessary) of the test subject, are stored in the target feature storage section 1050 so as to be associated with each other.

For example, in the examples illustrated in FIG. 21 and FIG. 22, at least (i) age of a test subject "55", (ii) gender of the test subject "male", and (iii) a fluorescent intensity "5500 (a.u.)" which is a feature, are stored in the target feature storage section 1050 so as to be associated with each other.

The accumulation amount specifying section 1042 specifies an amount of fluorescent-substance accumulated in a blood vessel on the basis of a fluorescent intensity of the blood vessel extracted by the feature extraction section 1041. Note that, in Embodiment 4, the accumulation amount specifying section 1042 specifies an amount of AGEs accumulation.

It can be said that AGEs are deposited on a blood vessel wall and will contribute to arteriosclerosis. Some AGEs emit fluorescence by being irradiated with excitation light. An intensity of the fluorescence is correlated to an amount of AGEs accumulated on the blood vessel wall or an amount of AGEs in blood. That is, it has become clear that the fluorescent intensity (A) becomes stronger as abundance of substances accumulated on the blood vessel increases, whereas (B) becomes weaker as the abundance of substances accumulated on the blood vessel decreases. AGEs accumulated on the blood vessel increase in accordance with aging. It is, however, noted that AGEs sharply increase in a case of hyperglycemia and/or hyperlipidemia, even in a case where a contributing factor of aging is not considered. It is therefore possible to externally observe an amount of AGEs accumulated on the blood vessel in a non-invasive manner on the basis of the actual age and a fluorescent intensity of the blood vessel of the test subject. This makes it possible to predict diseases by use of the amount of AGEs accumulation as an indicator of a health condition.

The control device 1020 has a proportion between a fluorescent intensity and an amount of AGEs accumulated on a blood vessel, and more specifically, has information indicative of such correlation (hereinafter, referred to as "correlation information") in advance. As illustrated in FIG. 17, the correlation information storage section 1051 of the control device 1020 stores fluorescent intensity/accumulation amount correlation information 150 indicative of a correlation between a fluorescent intensity and an amount of AGEs accumulation. The accumulation amount specifying section 1042 can specify more accurately, with reference the fluorescent intensity/accumulation amount correlation information 150, the amount of AGEs accumulated on the blood vessel of a test subject on the basis of the fluorescent intensity thus extracted.

Figure 23:
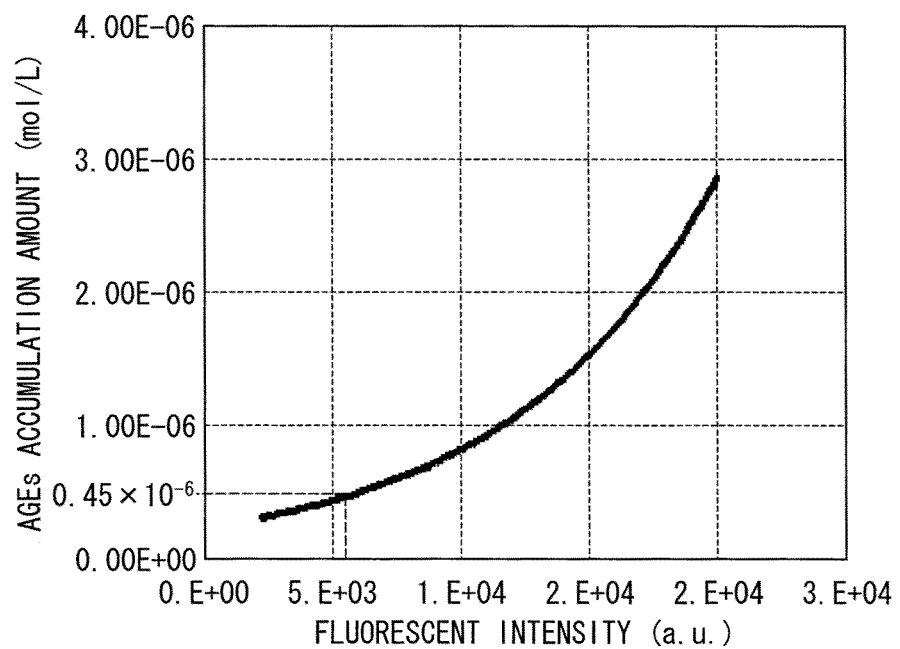
FIG. 23 is a graph showing a correlation between a peak fluorescent intensity and an amount of AGEs accumulation.

FIG. 23 is a graph showing a correlation between a fluorescent intensity and an amount of AGEs accumulation. The graph of FIG. 23 is stored, as the fluorescent intensity/accumulation amount correlation information 150, in the correlation information storage section 1051.

In the graph of FIG. 23, an abscissa indicates an fluorescent intensity (a.u.) extracted by the feature extraction section 1041 and an ordinate indicates an amount of AGEs accumulation (mol/L) correlated with the fluorescent intensity.

The fluorescent intensity/accumulation amount correlation information 150 of FIG. 23 is obtained from an evaluation experiment made in advance. Specifically, fluorescent intensities of all known various amounts of AGEs were evaluated, and an approximate function is derived from such evaluations.

A specific evaluation method is made, for example, as follows: a quartz tube containing a known amount of AGEs is sealed into skin of an artificially-made model of a human hand; the model is irradiated with excitation light; and a fluorescent intensity of the AGEs is measured. The AGEs that have not yet sealed into the model are prepared by use of, for example, AGE ELISA kit (produced by COSMO BIO CO., LTD.), AGE ELISA derived from glyceraldehyde in blood (produced by MIZUHO MEDY. Co., Ltd.), or FSK pentosidine (produced by FUSHIMI Pharmaceutical Co., Ltd.). By sealing the known amount of AGEs thus prepared into the model of the hand, it is possible to evaluate more accurately a relationship, obtained in a case of measuring a blood vessel of a wrist of a human body, between an fluorescent intensity and an amount of AGEs.

Note that, in Embodiment 4, the amount of AGEs accumulation means an amount of AGEs accumulated on a blood vessel wall. Embodiment 4 is, however, not limited to this. The accumulation amount specifying section 1042 can specify, as the amount of AGEs accumulation, AGEs density contained in blood or integration of AGEs density in blood and an amount of AGEs accumulated on a blood vessel wall. More indirectly, blood of a test subject is sampled, and AGEs density in the blood can be referred for evaluation. Alternatively, it is possible to obtain a correlation between AGEs intensity actually observed by a fluorescence method and AGEs density extracted from a blood vessel of a model animal.

In Embodiment 4, the accumulation amount specifying section 1042 specifies, with reference to the fluorescent intensity/accumulation amount correlation information 150 (graph of FIG. 23) stored in the correlation information storage section 1051, an amount of AGEs accumulated on a blood vessel of a test subject on the basis of an extracted fluorescent intensity in this measurement. For example, in the example of FIG. 22, the amount of AGEs accumulation is specified to be $0.45 \times 10^{-6}$ (mol/L) in a case where the fluorescent intensity is 5500 (a.u.).

The blood vessel state determination section 1043 determines a state of a blood vessel of a test subject on the basis of an amount of AGEs accumulated on the blood vessel specified by the accumulation amount specifying section 1042. It can be said that AGEs are deposited on and invade a blood vessel wall, so as to affect macrophage partially responsible for an immune system. This causes, for example, an inflammation while releasing cytokine which is a kind of protein, and ultimately causes arteriosclerosis to develop. In view of the circumstances, the blood vessel state determination section 1043 of Embodiment 4 determines, as a state of a blood vessel, a health condition of a blood vessel wall on the basis of an amount of AGEs accumulation. Specifically, the blood vessel state determination section 1043 determines how much damage the blood vessel wall receives from such deposition of AGEs.

More specifically, the blood vessel state determination section 1043 specifies a parameter called "blood vessel wall damage degree" which expresses a health condition of a blood vessel as a numerical value on the basis of a correlation between the amount of AGEs accumulation and the state of the blood vessel.

As described above, it has become clear that AGEs accumulated on a blood vessel partially cause circulatory diseases such as arteriosclerosis to develop. It can be said that risk of developing circulatory diseases becomes higher as an amount of AGEs accumulation is larger and damage of a blood vessel is larger. In view of the circumstances, a correlation between the amount of AGEs accumulation and the "blood vessel wall damage degree" is derived in accordance with a proportionality relation between an amount of AGEs accumulation and risk of developing diseases.

The correlation between the amount of AGEs accumulation and the blood vessel wall damage degree derived as described above is stored in advance, as accumulation amount/blood vessel state correlation information (first correlation information) 151 of the FIG. 17, in the correlation information storage section 1051.

Figure 24:
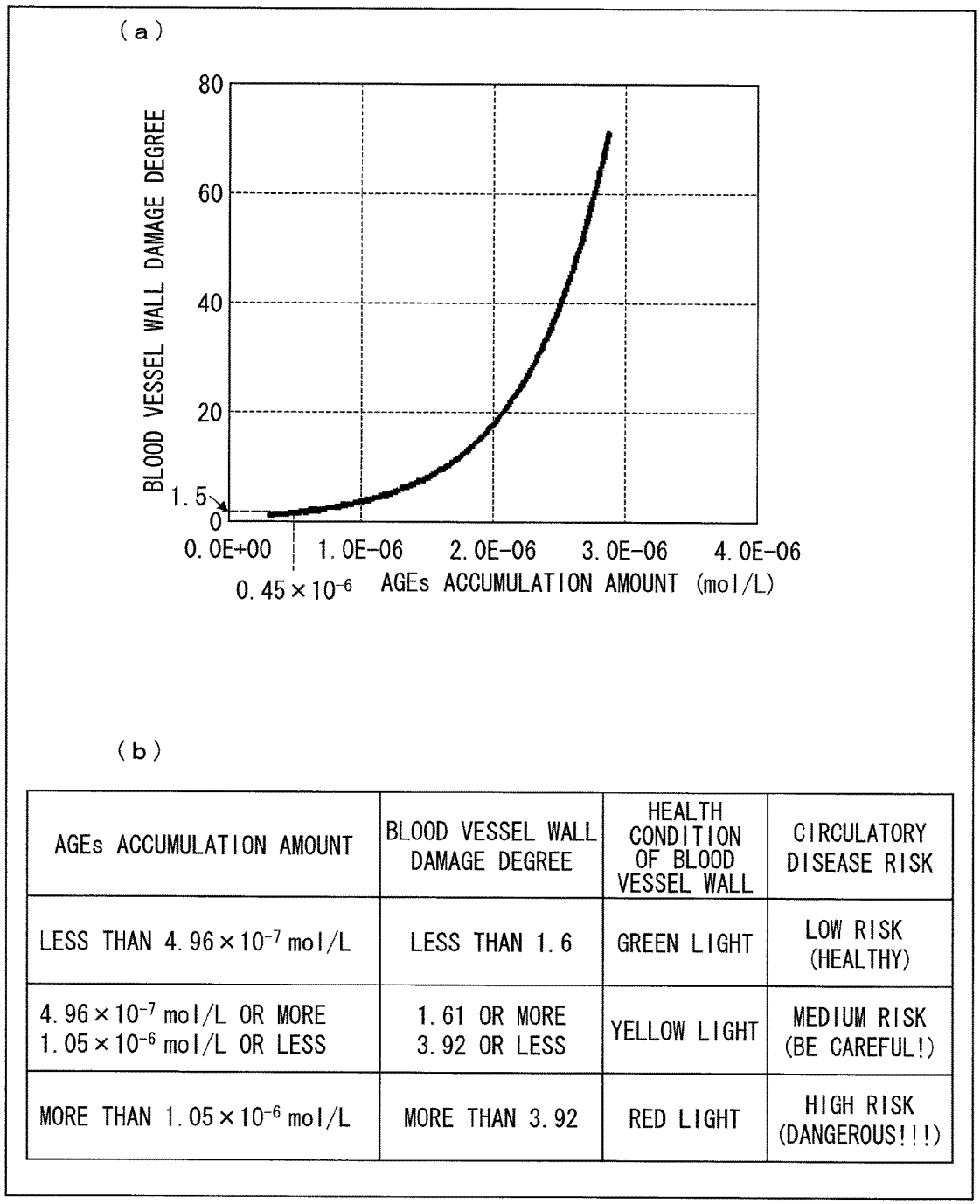
FIG. 24 (a) and (b) of FIG. 24 are views illustrating some specific examples of correlation information between an accumulation amount and a blood vessel state stored in a correlation information storage section.

(a) and (b) of FIG. 24 are views illustrating some examples of the accumulation amount/blood vessel state correlation information 151 stored in the correlation information storage section 1051.

(a) of FIG. 24 is a graph showing a correlation between an amount of AGEs accumulation and a blood vessel wall damage degree.

In (a) of FIG. 24, an abscissa indicates the amount of AGEs accumulation (mol/L) specified by the accumulation amount specifying section 1042, and an ordinate indicates the blood vessel wall damage degree correlated with the amount of AGEs accumulation.

In Embodiments of the present invention, the "blood vessel wall damage degree" is defined as a numerical value which falls within a range from 0 to about 80 (upper limit). A numerical value of the blood vessel wall damage degree of a healthy person falls within a range from 1 to 2 or so, irrespective of age. In a case where a numerical value of a blood vessel wall damage degree is more than 2, it is highly possible that damage to the blood vessel wall is advanced. This means that it is highly possible that aging of the blood vessel of a test subject is advanced more than that of his/her actual age. In Embodiment 4, the "blood vessel wall damage degree" indicative of a health condition of a blood vessel is an absolute value in which actual age is not taken into consideration. In contrast, as later described, "blood vessel age (measurement part age)" expressing how aging of a blood vessel progresses as a numerical value is a relative value in which actual age is taken into consideration. In this regard, the "blood vessel wall damage degree" and the "blood vessel age" are different from each other.

In Embodiment 4, the blood vessel state determination section 1043 determines, with reference to the accumulation amount/blood vessel state correlation information 151 (graph of (a) of FIG. 24) stored in the correlation information storage section 1051, the blood vessel wall damage degree of the blood vessel of the test subject on the basis of the specified amount of AGEs accumulation. For example, in examples of FIG. 22 and FIG. 23, the blood vessel wall damage degree is determined to be "1.5 (a.u.)" in a case where the amount of AGEs accumulation is $0.45 \times 10^{-6}$ (mol/L).

(b) of FIG. 24 is a table showing how an amount of AGEs accumulation corresponds to three ranks of a blood vessel wall damage degree in a case where a three-grade evaluation is made with respect to a blood vessel wall damage degree on the basis of risk of circulatory diseases.

The blood vessel state determination section 1043 (i) specifies, with reference to a table shown in (b) of FIG. 24, which one of the three ranks the specified amount of AGEs accumulation belongs to and (ii) makes the three-grade evaluation with respect to the blood vessel wall damage degree, the health condition of the blood vessel wall, and the risk of circulatory diseases are determined on the basis of the rank thus specified.

For example, in the examples of FIG. 22 and FIG. 23, in a case where the amount of AGEs accumulation is $0.45 \times 10^{-6}$ (mol/L), i.e., $4.5 \times 10^{-7}$ (mol/L), the blood vessel state determination section 1043 determines that (i) the blood vessel wall damage degree is "less than 1.61," (ii) the health condition of the blood vessel wall is a "green light," and (iii) the risk of circulatory diseases is "low risk (healthy)."

In Embodiment 4, alternatively, the blood vessel state determination section 1043 can be configured so that a numerical value of the blood vessel wall damage degree is calculated on the basis of a specified amount of AGEs accumulation, by use of the graph of (a) of FIG. 24, or can be configured so that the three-grade evaluation is made with respect to the blood vessel wall damage degree, the health condition of the blood vessel wall, and the risk of diseases, by use of the graph of (b) of FIG. 24, in accordance with the specified amount of AGEs accumulation. Alternatively, the graphs (a) and (b) of FIG. 24 can be both used.

The blood vessel age calculation section 1044 calculates blood vessel age of a test subject on the basis of (A) a blood vessel wall damage degree determined by the blood vessel state determination section 1043 and (B) information on test subject (age and gender) entered via the operation section degree of aging of the blood vessel of the test subject by use of a scale equivalent to that of age of the test subject by taking into consideration the blood vessel wall damage degree which is a damage degree of the blood vessel wall, the actual age, and the gender of the test subject.

Even in a case of a healthy person, an amount of AGEs accumulation and a blood vessel wall damage degree increase with age. In view of the circumstances, a test subject (user) can instinctively understand his/her health condition of a blood vessel with ease in comparison with actual age of the test subject, by (i) calculating, on the basis of the blood vessel wall damage degree, the blood vessel age expressed as a numerical value in which the actual age of a test subject is taken into consideration and then (ii) showing to the user a result of the calculation.

More specifically, according to Embodiment 4, the blood vessel age calculation section 1044 calculates blood vessel age on the basis of (i) actual age of a test subject, (ii) average life expectancy calculated based on actual age and gender of the test subject, and (iii) a blood vessel wall damage degree determined by the blood vessel state determination section 1043.

First, the blood vessel age calculation section 1044 calculates, with reference to gender and age/average life expectancy correlation information 152 stored in the correlation information storage section 1051, average life expectancy of a test subject on the basis of his/her gender and age entered via the operation section 1033.

FIG. 25 and FIG. 26 are views illustrating some specific examples of gender and age/average life expectancy correlation information 152. In Embodiment 4, the gender and age/average life expectancy correlation information 152 can be stored in any data format, provided that the gender and age/average life expectancy correlation information 152 includes a function which can specify average life expectancy on the basis of gender and actual age of a test subject. For example, as illustrated in FIG. 25, the gender and age/average life expectancy correlation information 152 is stored as a table showing a correspondence between the actual age and the average life expectancy for each gender. The blood vessel age calculation section 1044 can specify average life expectancy with reference to the table. In a case of, for example, (a) and (b) of FIG. 21, the gender of the information on test subject is: "male" and the actual age of the information on test subject is: "55 years old", and the blood vessel age calculation section 1044 specifies the average life expectancy of the test subject "26.3" in accordance with the table.

Alternatively, as illustrated in FIG. 26, a formula for calculating average life expectancy on the basis of gender and age can be stored in the gender and age/average life expectancy correlation information 152. The blood vessel age calculation section 1044 calculates the average life expectancy of the test subject by use of the formula for male on the basis of the information on test subject, and specifies his/her average life expectancy to be "26.313 ($\approx$26.3)".

Next, the blood vessel age calculation section 1044 calculates blood vessel age of the test subject on the basis of the average life expectancy, his/her actual age, and his/her blood vessel wall damage degree by use of the correlation between the blood vessel wall damage degree and the blood vessel age.

A blood vessel state/blood vessel age correlation information (second correlation information) 153 showing the correlation expressed by a formula is stored in the correlation information storage section 1051, and the blood vessel age calculation section 1044 calculates the blood vessel age of the test subject by use of the formula. In Embodiment 4, the blood vessel age calculation section 1044 calculates the blood vessel age by using the following formula as, for example, the blood vessel state/blood vessel age correlation information 153.

Blood vessel age=Average life expectancy−(Average life expectancy/Blood vessel wall damage degree)+(Actual age−10)

According to the blood vessel state/blood vessel age correlation information 153, it is possible to calculate the blood vessel age by use of a scale identical to that of the actual age in terms of the actual age. This makes it possible for the user to compare the actual age and the blood vessel age with each other. That is, the blood vessel age calculated on the basis of the blood vessel state/blood vessel age correlation information 153 can be shown to the user so that the user can easily understand how aging of the blood vessel wall progresses. The state of aging is caused only by a pathological cause of circulatory diseases, i.e., is subtracted from natural aging of the blood vessel caused by aging.

The blood vessel wall damage degree of the test subject in the specific example is "1.5". According to the formula, the blood vessel age calculation section 1044 can calculate the blood vessel age of the test subject as follows.

$$26.3-(26.3/1.5)+(55-10)\approx 53.77$$

In a case where the aforementioned blood vessel age is shown to the user, it is easily understood that the blood vessel age of the test subject is younger than the actual age (55 years old). Note that the blood vessel age calculation section 1044 can appropriately perform calculation, such as round-off, round-up, and/or round-down, so that the numerical value has an appropriate number of digits.

In a case where the blood vessel wall damage degree is 1.65, the blood vessel age of the test subject (55 years old, male) is about 55.3 years old. In this case, it is easily understood that the blood vessel age of the test subject is appropriate for the test subject's actual age.

In a case where the blood vessel wall damage degree is "80", the blood vessel age of the test subject (55 years old, male) is calculated to be about 71 years old. In this case, it is easily understood that the blood vessel age of the test subject greatly exceeds the actual age, so that aging of the blood vessel is highly accelerated.

Since the parameter of the average life expectancy which is correlated with the gender and the actual age is used in the formula, it is possible to calculate the blood vessel age based on the blood vessel wall damage degree in terms of the gender and the actual age of the test subject. Further, −10 is weighed in the last term of the formula; (actual age−10). Accordingly, in a case where the amount of AGEs accumulation of the test subject is lower than expected (blood vessel is barely blocked), the blood vessel age is calculated to be younger than the actual age. In a case where a measurement result in which the blood vessel age is younger than the actual age is outputted, consciousness of individuals' health management and motivation to keep a present condition of the test subject are improved. The control device 1020 can be preferable when used as a tool for the individuals' health management.

Note that the blood vessel state/blood vessel age correlation information 153 of the present invention is not limited to the formula. The blood vessel state/blood vessel age correlation information 153 can be any information, provided that the information indicates that damage of a blood vessel caused not by aging but by a pathological cause is derived from the blood vessel wall damage degree. Further, the blood vessel state/blood vessel age correlation information 153 does not need to be realized by a calculation formula, and can be realized by a graph showing the correlation between the blood vessel wall damage degree and the blood vessel age or can be realized by a correspondence table defining a correspondence between the blood vessel wall damage degree and the blood vessel age.

As described above, according to the configuration of the control device 1020 of the present invention, the feature extraction section 1041 extracts the peak intensity of the fluorescence from the measurement result acquired from the spectrograph 1010, and therefore the accumulation amount specifying section 1042 specifies the amount of AGEs accumulated on the blood vessel on the basis of the peak intensity. Further, the blood vessel state determination section 1043 determines a state of the blood vessel of the test subject on the basis of the specified amount of AGEs accumulation in accordance with the accumulation amount/blood vessel state correlation information 151. The state of the blood vessel is expressed by (A) a numerical value of the blood vessel wall damage degree or (B) a word directly expressing a health condition of the blood vessel wall or a risk of diseases. Such information about the blood vessel, expressed by numerical numbers or words, can be easily understood by a user, as compared with a case where the amount of AGEs accumulation is shown to the user. In a case where the user understands his/her health condition on the basis of information on the blood vessel, expressed by numerical numbers or words, the user does not need any special knowledge.

Accordingly, the present invention can provide, as information which can be easily understood without any special knowledge, a measurement result obtained by a measurement system for measuring chemical substances by use of a radiation property obtained by use of excitation light.

[Flow Of Measurement Processing Executed by Control Device]

Figure 27:
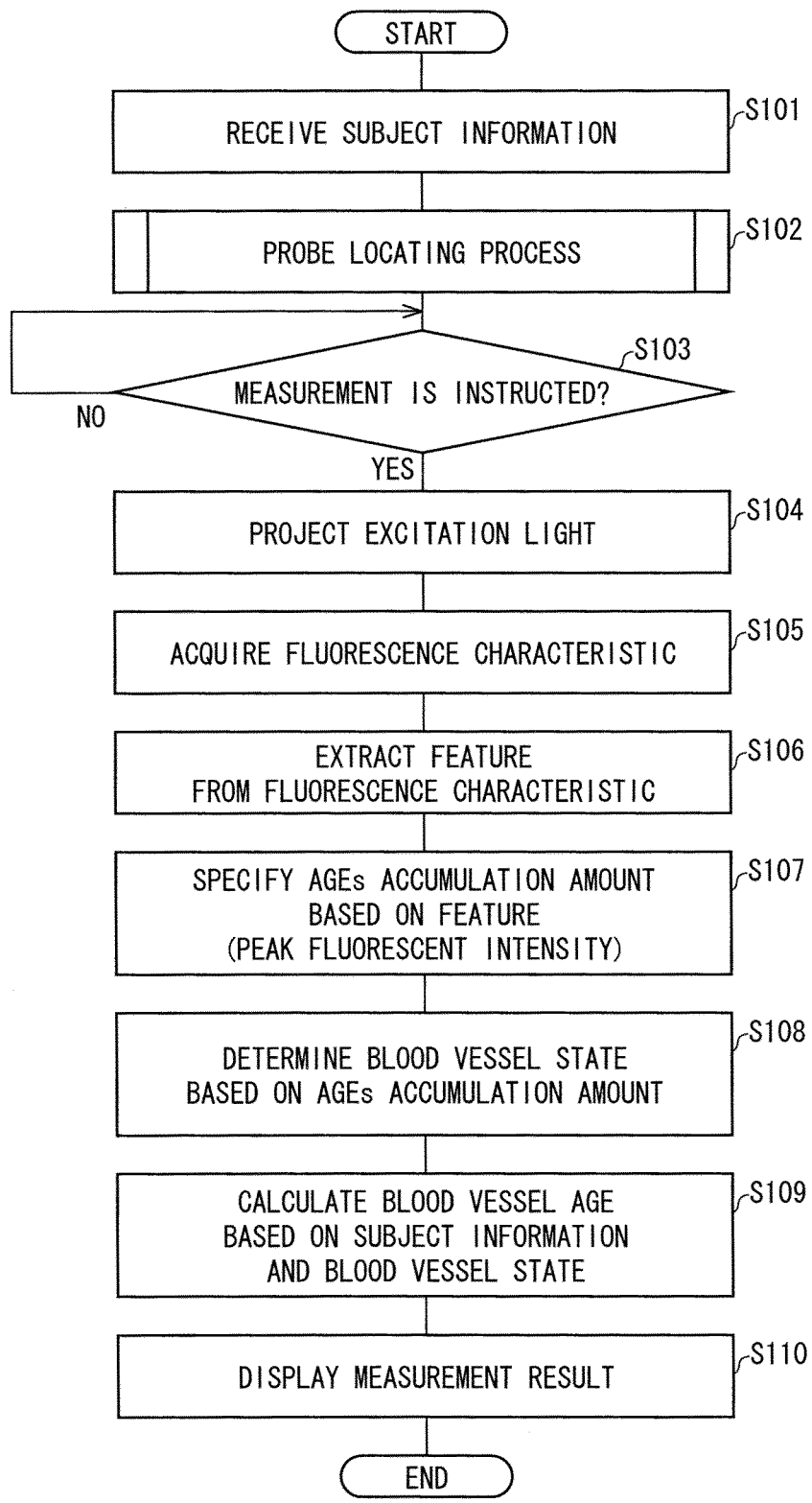
FIG. 27 is a flowchart showing processing executed by a control device in accordance with an embodiment of the present invention.
Figure 28:
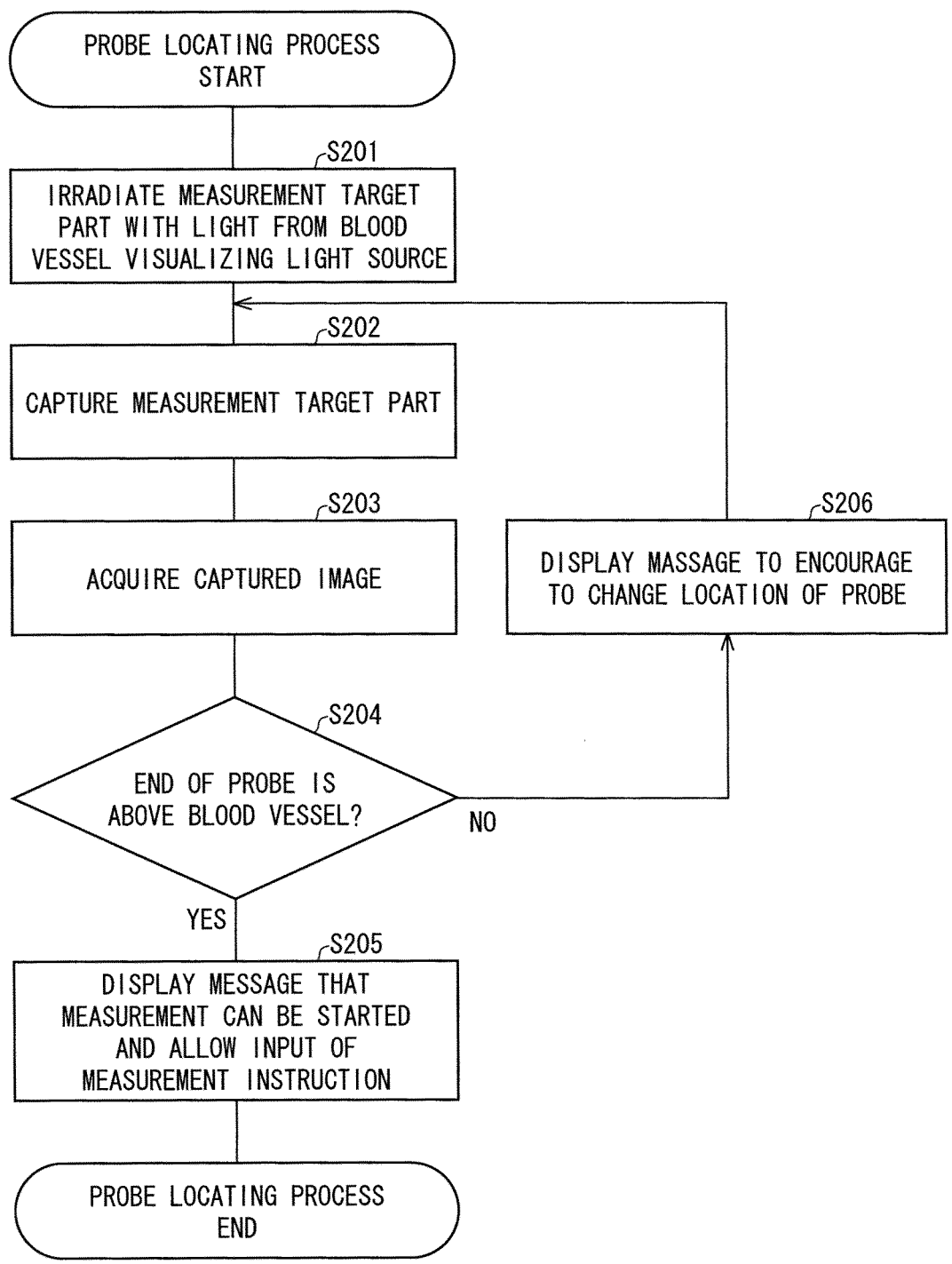
FIG. 28 is a flowchart showing a probe locating process executed by an irradiation location determination section of a control device.

FIG. 27 and FIG. 28 are flowcharts each showing processing executed by the control device 1020 in Embodiment 4 of the present invention. The control device 1020 realizes a measurement operation assisting function and a measurement result processing function by executing the following series of processes.

First, the display controlling section 1045 of the controlling section 1030 controls the display section 1032 to display an operation screen (see FIG. 21), and the controlling section 1030 accepts input of information on test subject (gender and age) via the operation section 1033 (S101). Then the controlling section 1030 executes a probe locating process (S102). The probe locating process is as follows: the controlling section 1030 controls the camera section 1005 and the blood vessel visualizing light source 1006 to acquire an image of a target measurement part of a test subject; and the irradiation location determination section 1046 determines whether or not a positional relationship between a blood vessel and an end of the probe 7 is appropriate on the basis of the image, however, details of the probe locating process will be described later with reference to FIG. 28. In a case where the irradiation location determination section 1046 determines that the positional relationship is appropriate and measurement can be started, the user can enter an instruction for starting the measurement.

In a case where the instruction for starting the measurement is entered to the control device 1020 via the operation section 1033 (YES in S103), the controlling section 1030 controls the excitation light source 9 to irradiate, with excitation light, a blood vessel of a wrist of the test subject housed in the image capturing housing 1004 (S104).

The spectrograph 1010 analyzes fluorescence radiated from the blood vessel, and the spectrograph controlling section 1040 of the control device 1020 acquires an obtained fluorescence characteristic (e.g., fluorescence spectrum of FIG. 22) (S105).

Then, the feature extraction section 1041 extracts a feature from the fluorescence characteristic thus acquired (S106). That is, as illustrated in the example of FIG. 22, the feature extraction section 1041 extracts a peak fluorescent intensity, which can be obtained when the fluorescent intensity becomes a peak, in a certain fluorescence wavelength range.

The accumulation amount specifying section 1042 specifies, with reference to fluorescent intensity/accumulation amount correlation information 150, an amount of AGEs accumulation on the basis of the feature thus extracted (peak fluorescent intensity) (S107).

The blood vessel state determination section 1043 determines, with reference to the accumulation amount/blood vessel state correlation information 151, a state of the blood vessel of the test subject on the basis of the specified amount of AGEs accumulation (S108). For example, the blood vessel state determination section 1043 calculates a blood vessel wall damage degree, and makes the three-grade evaluation with respect to a health condition of a blood vessel wall and a risk of circulatory diseases.

The blood vessel age calculation section 1044 calculates blood vessel age of the test subject on the basis of the information on test subject inputted in S101 and the blood vessel wall damage degree (S109). Specifically, first, the blood vessel age calculation section 1044 calculates, with reference to the gender and age/average life expectancy correlation information 152, an average life expectancy on the basis of the information on test subject. Then, the blood vessel age calculation section 1044 calculates the blood vessel age of the test subject on the basis of the actual age, the average life expectancy, and the blood vessel wall damage degree by use of a calculation formula serving as the blood vessel state/blood vessel age correlation information 153.

Finally, the display controlling section 1045 controls the display section 1032 to display the blood vessel age as a measurement result calculated by the blood vessel age calculation section 1044 (S101). The display controlling section 1045 can further controls the display section 1032 to display the blood vessel wall damage degree, the health condition of the blood vessel wall, and the risk of circulatory diseases which are determined by the blood vessel state determination section 1043. Furthermore, the display controlling section 1045 can control the display section 1032 to display the amount of AGEs accumulation, which is specified by the accumulation amount specifying section 1042, for a user having expertise.

FIG. 28 is a flowchart showing the probe locating process executed by the irradiation location determination section 1046.

First, the irradiation location determination section 1046 controls the blood vessel visualizing light source 1006 to irradiate the target measurement part (wrist) of the test subject which is housed in the image capturing housing 1004 with light emitted from a suitable light source (near-infrared LEDs 61, red LEDs 62, or the like) (S201). The irradiation location determination section 1046 also controls the camera section 1005 to capture the image of the wrist (S202). Then the irradiation location determination section 1046 acquires the image thus captured from the camera section 1005 (S203). The display controlling section 1045 can control the display section 1032 to display the image (either a video image or a still image).

The irradiation location determination section 1046 analyzes the image thus acquired, and determines whether or not the end of the probe 7 is located above the blood vessel of the wrist of the test subject (whether or not the positional relationship between the end and the blood vessel is appropriate) (S204).

In a case where the irradiation location determination section 1046 determines that the positional relationship is appropriate (YES in S204), the display controlling section 1045 controls the display section 1032 to display a message that the measurement can be started in response to the irradiation location determination section 1046 (e.g., (b) of FIG. 21). Further, the irradiation location determination section 1046 allows the user to enter an instruction for starting the measurement (S205). Alternatively, the irradiation location determination section 1046 can firstly permit the spectrograph controlling section 1040 to acquire measurement data from the spectrograph 1010.

Meanwhile, in a case where the irradiation location determination section 1046 determines that the positional relationship is inappropriate (NO in S204), the display controlling section 1045 controls the display section 1032 to display a message encouraging the user to change a location of the probe (e.g., (a) of FIG. 21) in response to the irradiation location determination section 1046 (S206).

After the user moves or locates the end of the probe 7, the irradiation location determination section 1046 goes back to the process, for example, the process of capturing the target measurement part (S202) or the process of analyzing the image (S203, S204). Those processes are repeatedly carried out until the irradiation location determination section 1046 determines that the end of the probe 7 is located above the blood vessel.

According to the method, it is possible to specify the amount of AGEs accumulated on the blood vessel on the basis of the peak fluorescence intensity in the measurement data acquired from the spectrograph 1010. It is also possible to convert a value of the amount of AGEs accumulation, which is difficult for a user to understand without any expertise, into numerical values (such as a blood vessel wall damage degree and a blood vessel age), or a word expressing the health condition of a blood vessel wall and the risk of diseases, which can be easily understood. Such information about the blood vessel, expressed by numerical numbers or words, can be easily understood by a user, as compared with a case where the amount of AGEs accumulation is shown to the user. In a case where the user understands his/her health condition on the basis of information on the blood vessel, expressed by numerical numbers or words, the user does not need any special knowledge.

Accordingly, the present invention can provide, as information which can be easily understood without any special knowledge, a measurement result obtained by a measurement system for measuring chemical substances by use of a radiation property obtained by use of excitation light.

[Display Example of Measurement Result]

Figure 29:
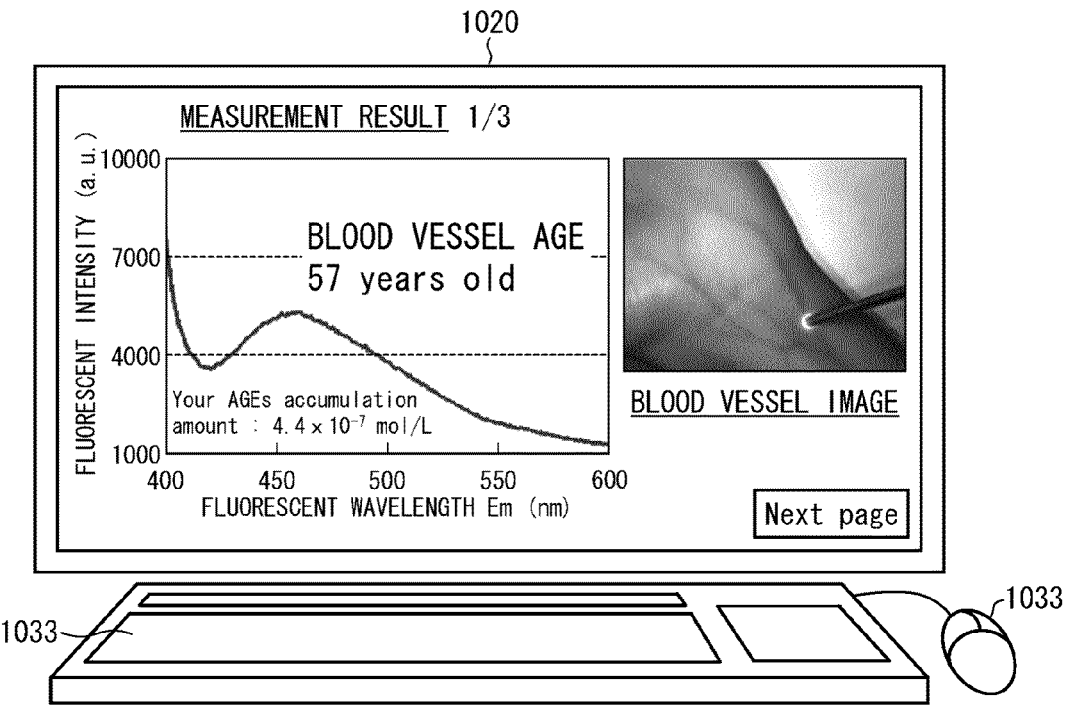
FIG. 29 is a view illustrating a specific example of a display screen displaying a measurement result.
Figure 30:
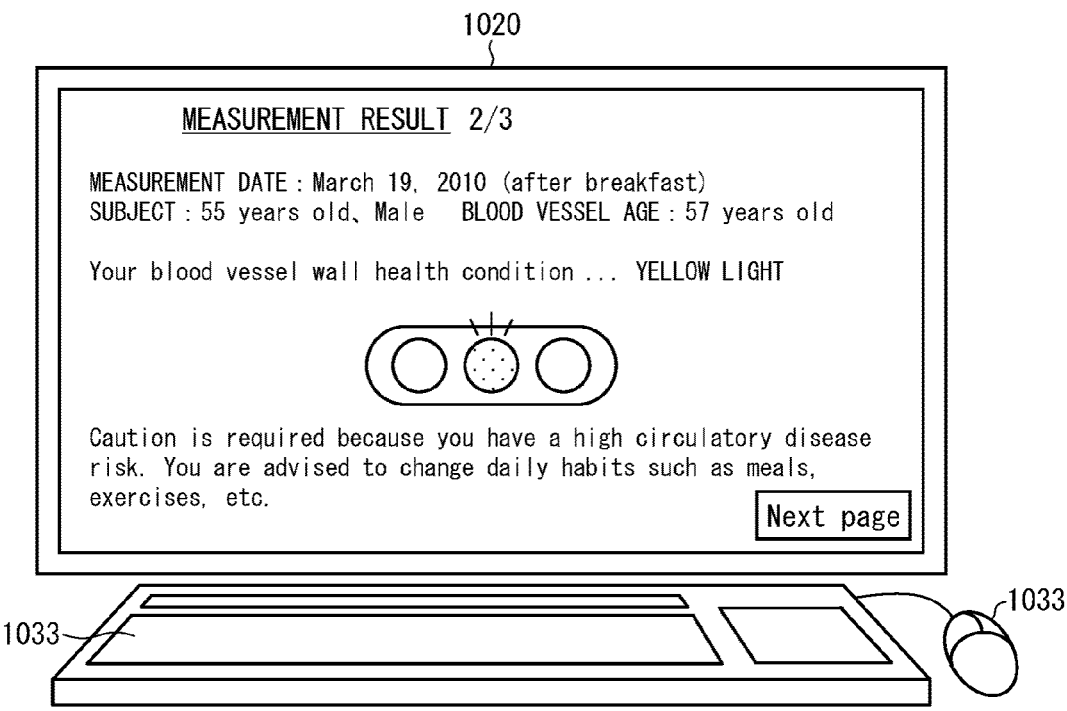
FIG. 30 is a view illustrating a specific example of a display screen displaying a measurement result.
Figure 31:
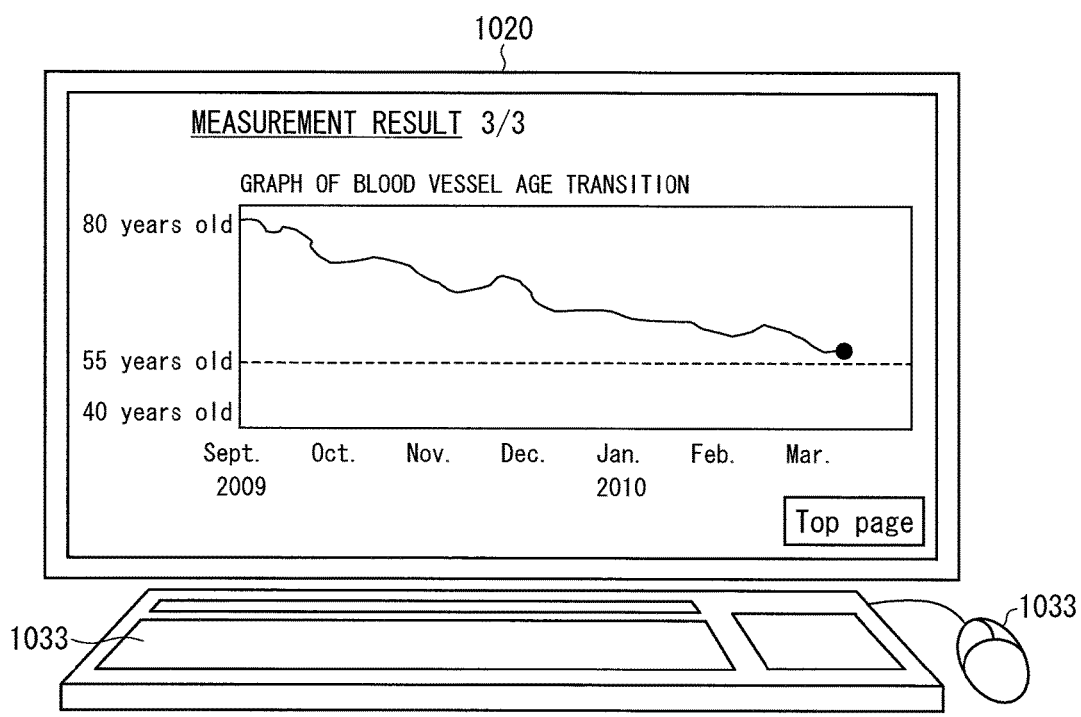
FIG. 31 is a view illustrating a specific example of a display screen displaying a measurement result.

FIG. 29 to FIG. 31 are views illustrating some examples of a display screen displaying a result of a measurement made by the measurement device 1001, which display screen is displayed to the display section 1032 of the control device 1020. A display screen shown in the drawings does not intend to limit the present invention, and can be therefore appropriately designed in accordance with a function of the measurement device 1001 and a purpose of measurement.

As illustrated in FIG. 29, the display controlling section 1045 can control the display section 1032 to display not only the blood vessel age calculated by the blood vessel age calculation section 1044 but also the graph of the fluorescence spectrum acquired from the spectrograph 1010 and the amount of AGEs accumulation specified by the accumulation amount specifying section 1042.

As illustrated in FIG. 30, the display controlling section 1045 can control the display section 1032 to display not only the blood vessel age, but also information on date and time when the measurement has been made and information on test subject. The display controlling section 1045 can further control the display section 1032 to display a result of the three-grade evaluation with respect to the state of the blood vessel. The result of the three-grade evaluation determined by the blood vessel state determination section 1043 can be expressed by illustration and letters.

In a case where the measurements are repeatedly made with respect to the identical test subject, as illustrated in FIG. 31, it is preferable that the display controlling section 1045 controls the display section 1032 to display a measurement result together with a past measurement result of a test subject so that a user can easily understand transition of a measurement result. It is therefore possible for the user to understand the transition of the measurement result more easily. For example, in a graph of FIG. 31, an abscissa indicates time, and an ordinate indicates blood vessel age, and the graph indicates transition of a blood vessel age and passage of time. In a case where an actual age is displayed in the graph, whether or not a blood vessel age of a test subject is higher than the actual age can be recognized at a glance. Also in a case where an actual age is displayed in the graph and the user aims to approximate a blood vessel age to his/her actual age, a user can aware daily changes at a glance in a case where the blood vessel age approximates to the actual age. As such, by displaying the measurement result as described above, it is possible to make the measurement system 1100 of the present invention more convenient as a tool for individuals' health management.

[Application Example]

A measurement result displayed on a display section 1032 can be compiled into a database by being stored every time when each test subject make a measurement.

For example, considering that a test subject measures a fluorescent intensity five times a day, i.e., (1) after he/she gets up, (2) to (4) at meals (5) before he/she sleeps. It is considered that information on test subject, measurement date, measurement timing ((1) to (5)), and food information in a case where the test subject make a measurement after meals, are recorded in a database so as to correspond to a measurement result (an amount of AGEs accumulation, a blood vessel wall damage degree, a blood vessel age, and the like). Information necessary to manage user's meals, such as the name of food, a food group, calories, and an image of the food that the user eats, is appropriately stored as the food information.

As such, in the measurement system 1100 of the present invention, the measurement results measured by the measurement device 1001 are managed in the form of database. It is therefore possible to keep, promote, improve a health condition by checking not only a health condition of one day before, but also a health conditions of one month before, six months before, and few years before. As described above, a measurement result is recorded in the database together with a content of a meal at a time of a day. This makes it possible to suitably use the measurement system 1100 of the present invention as individuals' health management system for managing a health condition by restricting dietary.

The measurement device of the present invention can be also expressed as follows.

It is preferable that the excitation light has a wavelength range suitable for measuring advanced glycation end products.

With the configuration, advanced glycation end products can be measured. The inventor of the present invention found that, in a case where a measurement target was irradiated with excitation light having wavelength suitable for measuring advanced glycation end products, a fluorescent intensity to be obtained largely varied depending on a location irradiated with excitation light. It is therefore useful to realize the present invention as a measurement device for measuring advanced glycation end products.

It is preferable that the measurement device further includes: an image capturing section for capturing the living body; a location calculation section (location calculation means) for calculating an irradiation location to be irradiated with the excitation light by analyzing an image captured by the image capturing section; and a location adjustment section for adjusting a location of the excitation light irradiation section so that the irradiation location calculated by the location calculation section is irradiated with the excitation light.

With the configuration, the location calculation section analyzes the image captured by the image capturing section, so that the irradiation location (irradiation location in a specific part or the irradiation location as a specific location) to be irradiated with excitation light is calculated. The location adjustment section adjusts the location of the excitation light irradiation section so that the irradiation location thus calculated is irradiated with the excitation light. An image of the living body is included in the image captured by the image capturing section, and, for example, a location to be irradiated with excitation light can be calculated on the basis of a feature existing on a surface of the living body (e.g., blood vessel, wrinkle, fingerprint, and mole). The surface of the living body to be captured as an image is less liable to largely change even in a plurality of measurement opportunities. It is therefore possible to set the irradiation location, which is to be irradiated with excitation light, to be located at a certain location.

It is preferable that the location calculation section calculates the irradiation location on the basis of a location of a blood vessel.

The location of the blood vessel scarcely changes even in a case where measurements are made repeatedly. A location to be irradiated with excitation light is calculated on the basis of the location of the blood vessel. This makes it possible to locate the irradiation location at the certain location.

It is preferable that the location calculation section calculates the irradiation location so that the blood vessel serving as the specific part is irradiated with the excitation light.

The inventor of the present invention found that, in a case where advanced glycation end products were measured, a stronger intensity of fluorescence could be obtained by irradiating a blood vessel (in particular, artery) with excitation light. With the configuration, since the stronger intensity of fluorescence can be obtained by irradiating the blood vessel with excitation light, a measurement value which is less affected by background and has high reliability can be obtained.

Further, it is preferable that: the measurement device further includes area calculation section (area calculation means) for calculating, by use of the image captured by the image capturing section, an area of a projection image of the excitation light projected toward the irradiation location; and distance calculation section (distance calculation means) for calculating an adjustment value for adjusting (i) a distance between the excitation light irradiation section and the specific part or (ii) a distance between the excitation light irradiation section and the specific location so as to be a predetermined distance on the basis of the area calculated by the area calculation section, the location adjustment section adjusting the distance on the basis of the adjustment value calculated by the distance calculation section.

With the configuration, (i) the distance between excitation light irradiation section and the specific part or (ii) the distance between excitation light irradiation section and the specific location is adjusted on the basis of the area of the projection image of excitation light. As the distance is short, the area of the projection image is small. As the distance is long, the area of the projection image is large. This makes it possible to adjust (i) the distance between the excitation light irradiation section and the specific part or (ii) the distance between the excitation light irradiation section and the specific location so that (i) the distance or (ii) the distance becomes a preferable predetermined distance on the basis of the area of the projection image of excitation light.

It is highly possible that a measurement value is changed in a case where (i) the distance or (ii) the distance thus adjusted is changed. By adjusting (i) the distance or (ii) the distance to become the predetermined distance, it is therefore possible to prevent the measurement value from varying.

It is preferable that the measurement device further includes: angle calculation means for calculating, by use of an image captured by the image capturing section, an adjustment value which causes an irradiation angle of the excitation light with respect to (i) a surface of the specific part or (ii) a living surface of the specific location to fall within a predetermined range of angle on the basis of a shape of a projection image of excitation light projected toward the irradiation location, the location adjustment section adjusting the irradiation angle on the basis of the adjustment value calculated by the angle calculation means.

With the configuration, the irradiation angle of the excitation light with respect to the surface of the living body is adjusted on the basis of the projection image of the excitation light. In a case where the excitation light is projected to be perpendicular to the surface of the living body, the projection image of the excitation light becomes a circle. Meanwhile, in a case where an irradiation axis of the excitation light is not perpendicular, the projection image becomes an oval. It is therefore possible to calculate the irradiation angle of the excitation light on the basis of a shape of the projection image of the excitation light.

It is highly possible that the measurement value is changed in a case where the irradiation angle is changed. By causing the irradiation angle to fall within a predetermined range of angle, it is possible to prevent the measurement value from varying.

It is preferable that the measurement device further includes a first storage section in which an image captured by the image capturing section and the irradiation location calculated by the location calculation section are stored so as to be associated with each other.

An image of the specific part or the specific location and the location to be irradiated with the excitation light are stored so as to be associated with each other. This makes it easier to irradiate an identical location with the excitation light even in a case where another measurement device is used.

It is preferable that the location calculation section corrects the irradiation location in a case where an intensity of the fluorescence received by the light receiving section is less than a predetermined fluorescent intensity.

A low fluorescent intensity is largely affected by the background. This decreases reliability of a measurement result. With the configuration, it is possible to improve a possibility to receive the fluorescence having a predetermined fluorescent intensity or more.

It is preferable that the measurement device further includes an illuminating section for irradiating the living body by switching between multiple kinds of illumination light whose respective wavelength ranges are different from each other.

A target can be easily or uneasily recognized depending on a wavelength of illumination light projected toward the measurement target. The surface of the living body is irradiated by switching between multiple kinds of illumination light whose respective wavelength ranges are different from each other, and therefore it is possible to improve recognition accuracy of the feature existing on the surface of the living body, which feature serves as a reference for locating the irradiation location.

It is preferable that the illuminating section emits light by switching between red light and infrared light.

It is possible to detect reduced hemoglobin by irradiating a skin surface with red light. This visualizes arteries. Further, it is possible to detect oxygenated hemoglobin by irradiating the skin surface with infrared light. This visualizes veins. Therefore, kinds of blood vessels can be easily detected by irradiating the skin surface while switching between red light and infrared light.

It is preferable that the measurement device further includes a light-shielding section for shielding environment light which is directed toward the specific part or the specific location.

The configuration can shield environment light which is directed toward the specific part or the specific location serving as the measurement target. The light receiving section can therefore receive more efficiently the fluorescence generated in the specific part or the specific location.

It is preferable that: the excitation light irradiation section includes: an excitation light source for generating the excitation light; and a light guiding section for guiding the excitation light emitted from the excitation light source, the light-shielding section having a slot section through which the light guiding section is to penetrate and in which the light guiding section is moved in a predetermined direction, the slot section including a blocking member made from a fibrous material made up of a plurality of fibers having light-shielding property and flexibility.

According to the configuration, the excitation light is projected toward the specific part or the specific location from the excitation light source via the light guiding section. Therefore, a location of the light guiding section is adjusted in order to adjust the location to be irradiated with excitation light. This makes it easier to adjust the irradiation location.

In this configuration, in a case where the light guiding section penetrates the light-shielding section, it is highly possible that ambient light enters the light-shielding section through a penetrated part in which the light guiding section penetrates the light-shielding section. In view of the circumstances, the blocking member made from the fibrous material made up of the plurality of fibers having light-shielding property and flexibility is provided in the slot section through which the light guiding section is to penetrate. This makes it possible to prevent (i) ambient light and (ii) dust and dirt from entering the light-shielding section even in a case where the location of the light guiding section is changed.

It is preferable that the measurement device further includes: a second storage section for storing location information indicative of a location to be irradiated with the excitation light; and a location adjustment section for adjusting a location of the excitation light irradiation section so that a location indicated by the location information which is stored in the second storage section is irradiated with the excitation light.

With the configuration, the location information indicative of a location to be irradiated with excitation light is stored, and the location of the excitation light irradiation section is adjusted so that the location indicated by the location information is irradiated with excitation light.

In a case where the irradiation location is determined once, a location identical to such a determined location will be irradiated with excitation light in the next measurement opportunity. Note that the location information which is stored in the second storage section can be calculated by the measurement device or can be inputted by a user.

It is preferable that the measurement device includes: a location adjustment section for adjusting an irradiation location of the excitation light emitted from the excitation light irradiation section; an image capturing section for capturing a part irradiated with the excitation light; a second storage section for storing an image captured by the image capturing section; and a display section for displaying the image stored in the second storage section.

According to the configuration, the user can know where to project excitation light by watching the past captured image(s) displayed on the display section. This makes it easier to irradiate identical locations with excitation light in a plurality of measurement opportunities.

It is preferable that the measurement device further includes a fixing section for fixing a location of the specific part or the specific location with respect to the excitation light irradiation section.

According to the configuration, since the location of the specific part or the specific location with respect to the excitation light irradiation section is fixed by use of the fixing section, it is possible to locate the excitation light irradiation section in the identical locations of the living body in the plurality of measurement opportunities. This makes it possible to irradiate the identical locations with excitation light in the plurality of measurement opportunities.

It is preferable that the light receiving section includes a plurality of light guiding sections each having a different diameter, said measurement device, further comprising: a switching section for switching between the plurality of light guiding sections each receiving the fluorescence.

An optimum diameter of the light receiving section varies depending on a size of the specific part (e.g., blood vessel) to be irradiated with excitation light. Accordingly, by switching between the plurality of light guiding sections each having a different size, it is possible to make an optimum measurement with respect to the multiple kinds of tissues and organs each having a different size.

It is preferable that the excitation light irradiation section and the light receiving section are provided so as to have a plurality of combinations of (i) respective excitation light irradiation sections and (ii) respective light receiving sections, and measurements are made with respect to respective locations.

With the configuration, the plurality of parts can be simultaneously measured, so that measurement time can be shortened.

It is preferable that, in the measurement device, the measurements are made with respect to at least respective three parts each serving as the specific part including an artery, a vein, and a part in which no blood vessel exists.

With the configuration, measurements are simultaneously made with respect to a plurality of parts. It is highly possible that measurement values of the artery, the vein, and the part in which no blood vessel exists differ from each other. This can broaden options to analyze measurement values. For example, the most reliable one of the three measurement values can be selected.

It is preferable that the measurements are made with respect to a plurality of parts each having a different size in the artery or the vein serving as the specific part.

With the configuration, it is possible to simultaneously measure the plurality of parts each having a different size in the artery or the vein. This can broaden options to analyze measurement values. For example, the most reliable one of the plurality of obtained measurement values can be selected.

It is preferable that the measurement device further includes: a location adjustment section for adjusting a first irradiation location to be irradiated with the excitation light emitted from the excitation light irradiation section; an image capturing section capturing a region containing the specific part or the specific location; location calculation section for calculating a second irradiation location to be irradiated with the excitation light by analyzing an image captured by the image capturing section; and an informing section for informing that the first irradiation location does not match the second irradiation location in a case where the first irradiation location does not match the second irradiation location.

According to the configuration, the location to be irradiated with excitation light is calculated by the location calculation section, and the informing section informs that the irradiation location is not irradiated with excitation light in a case where the irradiation location thus calculated is not irradiated with excitation light. This informing can be carried out by use of sound, image, light, or/and the like. That is, the informing section is a speaker, a display section, a light emitting device, or a combination of them.

This makes it easier to irradiate the location to be irradiated with excitation light in a case where the user (test subject) adjusts the location to be irradiated with excitation light by use of the location adjustment section.

It is preferable that the measurement device further includes the steps of: (C) receiving fluorescence which serves as a standard fluorescence in a case where an intensity of fluorescence is measured, (D) correcting an intensity of the fluorescence received in the step (B) by use of the intensity of the fluorescence received in the step (C).

With the configuration, the intensity of the fluorescence received in the step (B) can be corrected on the basis of the standard fluorescence (reference). This can improve reliability of a measurement value.

In order to achieve the aforementioned object, a method for controlling a measurement device in accordance with the present invention, the measurement device including: an excitation light irradiation section for irradiating a specific part or a specific location of a living body with excitation light; a light receiving section for receiving fluorescence generated by irradiating the specific part or the specific location with the excitation light; an image capturing section for capturing the living body; and a location adjustment section for adjusting a location of the excitation light irradiation section, said method comprising the steps of: (a) causing the measurement device to analyze an image captured by the image capturing section; (b) causing the measurement device to calculate an irradiation location to be irradiated with the excitation light on the basis of content thus analyzed in the step (a); and (c) causing the measurement device to control the location adjustment section so that the irradiation location calculated in the step (b) is irradiated with the excitation light.

Further, the measurement result processing device of the present invention can be expressed as follows.

The measurement result processing device further includes a correlation information storage section which stores first correlation information indicative of a correlation between the amount of fluorescent substances and the damage degree of the target measurement part, the damage degree determination means determining the damage degree on the basis of the amount of fluorescent substances by use of the first correlation information.

With the configuration, the correlation (derived in advance as described above) between the amount of fluorescent substances included in the target measurement part and the damage degree of the target measurement part can be stored in advance in the correlation information storage section.

Accordingly, the damage degree determination means can repeatedly output the damage degree with ease and stable accuracy on the basis of the amount of fluorescent substances by use of the first correlation information, provided that the measurement result falls within an assumed range of the amount of fluorescent substances.

It is preferable that age calculation means for calculating measurement part age indicative of how aging of the target measurement part progresses on the basis of actual age of the test subject (living body) and the damage degree of the target measurement part, the actual age being entered to the measurement result processing device, the damage degree being determined by the damage degree determination means.

According to the configuration, the age calculation means can calculate the measurement part age indicative of how aging of the target measurement part progresses in consideration of the actual age of the test subject, with regard to the damage degree of the target measurement part, which damage degree is determined by the damage degree determination means. In the measurement result processing device, the damage degree which is an abstract conception is replaced with age which is more concrete conception. This makes it possible to provide the measurement result that a user can more easily understand than the damage degree.

Therefore, the user can analyze a measurement result and understand a state of a test subject with ease by comparing a measurement part age and an actual age of the test subject with each other, even in a case where the user does not have any special knowledge.

A measurement result processing device includes: a correlation information storage section for storing second correlation information indicative of a correlation between (I) the actual age of the test subject (living body) and the damage degree and (II) the measurement part age, the age calculation means calculating the measurement part age on the basis of the actual age of the living body and the damage degree by use of the second correlation information.

According to the configuration, the correlation (derived in advance as described above) between the damage degree of the target measurement part and a state of aging of the target measurement part can be stored in the correlation information storage section in advance.

Accordingly, the age calculation means can repeatedly output the blood vessel age with ease and stable accuracy on the basis of the actual age and the damage degree of the test subject by use of the second correlation information.

the age calculation means further (i) specifies an average life expectancy based on the actual age of the test subject (living body) and (ii) calculates the measurement part age by use of a formula as the second correlation information;

Measurement part age=Average life expectancy−(Average life expectancy/Damage degree)+(Actual age−10).

It is preferable that the age calculation means specifies the average life expectancy on the basis of gender and the actual age of the test subject (living body), the gender and the actual age being entered to the measurement result processing device. Since the average life expectancies are different between male and female, the average life expectancy is specified for each gender. This makes it possible to calculate more accurately the measurement part age by use of the aforementioned formula.

It is preferable that the feature extraction means extracts the fluorescence characteristic of the fluorescence emitted from the blood vessel, which fluorescence is obtained by irradiating, with excitation light, the blood vessel of the target measurement part; the substance amount specifying means specifies the amount of fluorescent substances contained in the blood vessel; the damage degree determination means determines the blood vessel wall damage degree indicative of a degree of damage of a blood vessel wall on the basis of the amount of fluorescent substances in the blood vessel; and the age calculation means calculates a blood vessel age on the basis of the actual age of the test subject (living body) and the blood vessel wall damage degree.

It is preferable that the feature extraction means extracts the fluorescence characteristic of the fluorescence emitted from the blood vessel, which fluorescence is obtained by irradiating, with excitation light, the blood vessel of the target measurement part; the substance amount specifying means specifies the amount of fluorescent substances contained in the blood vessel; and the damage degree determination means determines a blood vessel wall damage degree indicative of a degree of damage of the blood vessel wall on the basis of the amount of fluorescent substances in the blood vessel.

According to the configuration, it is possible to provide, to the user, not only the amount of fluorescent substances contained in the blood vessel of the test subject but also the blood vessel wall damage degree indicative of the degree of the damage of the blood vessel wall (and also provide, to the user, the blood vessel wall damage degree and the blood vessel age indicative of how aging of the blood vessel progresses).

Accordingly, the user can easily understand his/her health condition of the blood vessel of the test subject. To put it another way, the user can easily use the measurement result processing device of the present invention, without any special knowledge, as a tool for individuals' health management relating to circulatory diseases.

It is preferable that the feature extraction means extracts, as the fluorescence characteristic, a peak fluorescent intensity in a predetermined range of wavelength from a spectrum of fluorescence of the target measurement part obtained by irradiating, with excitation light, the target measurement part.

Accordingly, measurement of the amount of fluorescent substances and the state of the target measurement part can be determined with more ease and high accuracy by efficiently extracting a unique characteristic of the fluorescent substances serving as an effective indicator for understanding the state of the test subject.

It is preferable that the substance amount specifying means specifies an amount of advanced glycation end products contained in the target measurement part.

It is found that the amount of advanced glycation end products (AGEs) contained in the body of the test subject correlates with the health condition of the test subject. Therefore, the measurement result processing device can output the measurement result based on the amount of advanced glycation end products relating to the health condition of the test subject so that the user can understand the measurement result without any special knowledge.

It is preferable that display controlling means for controlling a display section to display a result of processing carried out by the measurement result processing device.

Out of various kinds of information (such as the fluorescence characteristic outputted by the feature extraction means the amount of fluorescent substances outputted by the substance amount specifying means, and the damage degree supplied from the damage degree determination means (or, in addition to them, the measurement part age supplied from the age calculation means)) of the measurement result processing device, some kinds of information which is easy for the user to understand can be provided to the user so that the user can visually confirm those some kinds of information.

In order to attain the aforementioned object, a measurement system of the present invention includes: a measurement device for acquiring measurement data of fluorescence generated by irradiating a target measurement part of a test subject (living body) with excitation light; and any one of the measurement result processing devices, which processes the measurement data acquired by the measurement device, said measurement device including: a light-shielding section for shielding environment light which is directed toward the target measurement part of the test subject; an excitation light source for irradiating the target measurement part of the test subject with excitation light; and a detector for generating the measurement data by analyzing the fluorescence generated by irradiating the target measurement part with the excitation light.

In the measurement system, the measurement device can further include: a blood vessel visualizing light source for visualizing the blood vessel of the target measurement part by irradiating the target measurement part; and a camera section for capturing the target measurement part irradiated with light of the blood vessel visualizing light source.

According to the configuration, in a case where the target measurement part is assumed to be the blood vessel of the test subject, accurate measurement data of the fluorescence of the blood vessel can be obtained. That is, it is possible to specify more accurately the amount of fluorescent substances in the blood vessel.

In order to attain the aforementioned object, a method of processing measurement result in accordance with the present invention includes the steps of: (A) extracting a fluorescence characteristic in fluorescence generated by a target measurement part obtained by irradiating, with excitation light, a part serving as the target measurement part of a body of a test subject; (B) specifying an amount of fluorescent substances contained in the target measurement part on the basis of the fluorescence characteristic extracted in the step (A); and (C) determining a damage degree indicative of a degree of damage received by the target measurement part or a part of the target measurement part on the basis of the amount of fluorescent substances specified in the step (B).

Note that the measurement device and the measurement result processing device can be realized by a computer. Accordingly, the scope of the present invention includes: (I) a control program of the measurement device for causing a computer to realize the measurement device, the control program causing the computer to function as each means of the measurement device; (II) a control program of the measurement result processing device for causing a computer to realize the measurement result processing device, the measurement result processing device causing the computer to function as each means of the measurement result in which the control program for causing a computer to realize the measurement device is stored; and (IV) a computer readable recording medium in which the control program for causing a computer to realize the measurement result processing device is stored.

(Other Modification)

The present invention is not limited to the description of the embodiments above, and can be modified in numerous ways by a skilled person as long as such modification falls within the scope of the claims. An embodiment derived from a proper combination of technical means disclosed in different embodiments is also encompassed in the technical scope of the present invention.

For example, a control device 20 and a measurement device 1 can be integrally formed. That is, the measurement device 1 can include: a microcomputer whose function is similar to that of a main control section 21; a section corresponding to a display section 30; a section corresponding to an input section 31; and a section corresponding to a storage section 32.

Further, for example, the control device 1020 and a measurement device 1001 can be integrally formed. That is, the measurement device 1001 includes: a microcomputer whose function is similar to that of a controlling section 1030; a section corresponding to a display section 1032; a section corresponding to an operation section 1033; a section corresponding to a storage section 1031; and a section corresponding to a communication section 1034.

Furthermore, the control device 20 and the control device 1020 can be integrally formed. That is, a control device can be a microcomputer having (i) the function similar to that of the main control section 21 and (ii) the function similar to that of the controlling section 1030. In this case, one measurement device can be formed as follows: sections (configurations) whose functions are similar to each other are eliminated from sections of the measurement device 1 and the measurement device 1001; and only necessary sections are appropriately incorporated with each other. It is therefore possible to realize a measurement device, a control device, and a measurement system, each of which can: (A) reduce variation of measurement values caused by a misalignment between irradiation locations irradiated with excitation light in a case where a target measurement part whose fluorescence varies depending on a location irradiated with excitation light is measured; and (B) provide to a user a measurement result (obtained in the measurement system of chemical substances) serving as information which can be easily understood without any expertise, and a radiation property obtained from excitation light is used in the measurement system.

Further, blocks of the control device 20 and blocks of a portable terminal 70, in particular, the main control section 21 can be configured by a hardware logic, or alternatively, can be configured by software by use of a CPU as follows. Furthermore, blocks of the control device 1020, in particular, the feature extraction section 1041, the accumulation amount specifying section 1042, the blood vessel state determination section 1043, the blood vessel age calculation section 1044, and the irradiation location determination section 1046 can be configured by a hardware logic, or alternatively, can be configured by software by use of a CPU as follows.

That is, the control device 20, the portable terminal 70, and the control device 1020 include a CPU (central processing unit) which carries out a command of a control program for realizing functions, a ROM (read only memory) which stores the program, a RAM (random access memory) which develops the program, and a storage apparatus (recording medium), such as a memory, which stores the program and various kinds of data. Further, the object of the present invention can be also realized in such a manner that: a recording medium is provided to the control device 20, the portable terminal 70, or the control device 1020, which recording medium has stored program codes (execution mode program, intermediate code program, and source program) (serving as software for realizing the aforementioned functions) of a control program in the control device 20, the portable terminal 70, or the control device 1020 so as to be readable by a computer; and the program codes stored in the recording medium are read out and carried out by the computer (or CPU or MPU).

Examples of the recording medium encompass: tapes such as a magnetic tape and a cassette tape; disks such as magnetic disks (e.g., a floppy (registered trademark) disk and a hard disk) and optical disks (e.g., a CD-ROM, an MO, an MD, a DVD, and a CD-R); cards such as an IC card (including a memory card) and an optical card; and semiconductor memories (e.g., a mask ROM, an EPROM, an EEPROM, and a flash ROM).

Further, the control device 20, the portable terminal 70, and the control device 1020 may be configured to be connect to a communication network, and the program code may be supplied via the communication network. The communication network is not particularly limited, and examples of the communication network encompass the Internet, an intranet, an extranet, a LAN, an ISDN, a VAN, a CATV communication network, a virtual private network, a telephone network, a mobile communication network, and a satellite communication network. In addition, a transmission medium constituting the communication network is not particularly limited, and examples of the transmission medium encompass: wired transmission media such as IEEE1394, a USB, a power-line carrier, a cable TV line, a telephone line, and an ADSL; and wireless transmission media such as infrared rays (e.g., IrDA and a remote controller), Bluetooth (registered trademark), 802.11 wireless, an HDR (high data rate), a cell-phone network, and a satellite line, and a digital terrestrial network. Note that the present invention may be also realized by a computer data signal which has the program codes specified with electronic transmission and is embedded in a carrier wave.

INDUSTRIAL APPLICABILITY

A measurement device of the present invention can be used for a measurement device and a measurement system in which measurement values differ depending on irradiation locations irradiated with excitation light. This makes it possible to reduce variation of the measurement values. A measurement result processing device of the present invention can be used for a measurement device and a measurement system for chemical substances in which a radiation property obtained with use of excitation light is used. This makes it possible to provide, to a user, the measurement result thus obtained as information which can be easily understood without any special knowledge. Further, the measurement result processing device of the present invention can be provided as a health indicator that a user can instinctively understand with ease, so that the measurement result processing device can be also suitably used as an individuals' health management system.

REFERENCE SIGNS LIST

1 measurement device
2 bottom section
2a insertion port
2b opening
3 cylindrical section
3a probe insertion port (slot section)
3b blocking member
4 image capturing housing (light-shielding section)
5 camera (image capturing section)
5a lens
6 blood vessel visualizing light source (illuminating section)
6a switch
7 probe (excitation light irradiation section, light guiding section)
7a incident fiber (excitation light irradiation section)
7b reflection fiber (light receiving section)
8 probe operation section (location adjustment section)
9 excitation light source
10 detector
20 control device
21 main control section
22 two-dimensional coordinate calculation section (location calculation unit)
23 angle calculation section (angle calculation unit)
24 area calculation section (area calculation unit)
25 distance calculation section (distance calculation unit)
26 moving section controlling section (location adjustment controlling unit)
27 angle adjustment section controlling section (location adjustment controlling unit)
28 distance adjustment section controlling section (location adjustment controlling unit)
29 measurement data analysis section
30 display section
31 input section
32 storage section (first storage section, second storage section)
40 measurement device
41 image capturing housing (light-shielding section)
42 opening
43 valvate member
44 arm pillow (fixing section)
50 measurement device
51 image capturing housing (light-shielding section)
52 opening
60 measurement device
61 near-infrared LED
62 red LED
63 substrate
64 opening
65 fixing washer
66 screw
70 portable terminal (control device)
71 display section
81 probe guide
82 support
83 distance adjustment section (location adjustment section)
84 angle adjustment section (location adjustment section)
85 moving section (location adjustment section)
86 rack rail
87 stage
100 measurement system
150 fluorescent intensity/accumulation amount correlation information
151 accumulation amount/blood vessel state correlation information (first correlation information)
152 gender and age/average life expectancy correlation information
153 blood vessel state/blood vessel age correlation information (second correlation information)
1001 measurement device
1002 bottom section
1002a insertion port
1002b opening
1003 measurement target housing section
1003a probe insertion port
1004 image capturing housing (light-shielding section)
1005 camera section
1006 blood vessel visualizing light source
1008 probe support section
1010 spectrograph (detector)

1020 control device (measurement result processing device)
1030 controlling section
1031 storage section
1032 display section
1033 operation section
1034 communication section
1040 spectrograph controlling section
1041 feature extraction section (feature extraction unit)
1042 accumulation amount specifying section (substance amount specifying unit)
1043 blood vessel state determination section (damage degree determination unit)
1044 blood vessel age calculation section (age calculation unit)
1045 display controlling section
1046 irradiation location determination section
1050 target feature storage section
1051 correlation information storage section
1060 substrate
1063 opening
1064 screw
1081 probe guide
1083 clamp
1100 measurement system

The invention claimed is:

1. A measurement system, comprising:
a measurement device for acquiring measurement data of fluorescence generated by irradiating a target measurement part of a living body with excitation light; and
a measurement result processing device which processes the measurement data acquired by the measurement device,
said measurement device including:
a light-shielding section for shielding environment light which is directed toward the target measurement part of the living body;
an excitation light source for irradiating the target measurement part of the living body with excitation light; and
a detector for generating the measurement data by analyzing the fluorescence generated by irradiating the target measurement part with the excitation light, said measurement result processing device including:
a feature extraction section configured to extract a fluorescence characteristic of fluorescence emitted from the target measurement part, which fluorescence is obtained by irradiating, with excitation light, the target measurement part of a living body;
a substance amount specifying section configured to specify an amount of fluorescent substances contained in the target measurement part on the basis of the fluorescence characteristic extracted by the feature extraction section;
a damage degree determination section configured to determine a damage degree indicative of a degree of damage received by the target measurement part or a part of the target measurement part on the basis of the amount of fluorescent substances specified by the substance amount specifying section;
an age calculation section for calculating measurement part age indicative of how aging of the target measurement part progresses on the basis of actual age of the living body and the damage degree of the target measurement part, the actual age being entered to the measurement result processing device, the damage degree being determined by the damage degree determination section; and
a correlation information storage section configured to store first correlation information indicative of a correlation between (I) the actual age of the living body, the average life expectancy, and the damage degree, and (II) the measurement part age,
the age calculation section calculating the measurement part age by use of formula as the first correlation information;

Measurement part age=Average life expectancy−(Average life expectancy/Damage degree)+(Actual age−10).

2. The measurement system as set forth in claim 1, wherein:
the correlation information storage section further stores second correlation information indicative of a correlation between the amount of fluorescent substances and the damage degree of the target measurement part; and
the damage degree determination section determines the damage degree on the basis of the amount of fluorescent substances by use of the second correlation information.

3. The measurement system as set forth in claim 1, wherein the age calculation section specifies the average life expectancy on the basis of gender and the actual age of the living body, the gender and the actual age being entered to the measurement result processing device.

4. The measurement system as set forth in claim 1, wherein the feature extraction section is configured to extract, as the fluorescence characteristic, a peak fluorescent intensity in a predetermined range of wavelength from a spectrum of fluorescence of the target measurement part obtained by irradiating, with excitation light, the target measurement part.

5. The measurement system as set forth in claim 1, wherein the substance amount specifying section is configured to specify an amount of advanced glycation end products contained in the target measurement part.

6. The measurement system as set forth in claim 1, further comprising
a display control unit for controlling a display section to display a result of processing carried out by the measurement result processing device.

7. The measurement system as set forth in claim 1, wherein the target measurement part includes a blood vessel and wherein:
the feature extraction section configured to extract the fluorescence characteristic of the fluorescence emitted from the blood vessel, which fluorescence is obtained by irradiating, with excitation light, the blood vessel of the target measurement part;
the substance amount specifying section configured to specify the amount of fluorescent substances contained in the blood vessel;
the damage degree determination section configured to determine the blood vessel wall damage degree indicative of a degree of damage of a blood vessel wall on the basis of the amount of fluorescent substances in the blood vessel;
the age calculation section configured to calculate a blood vessel age on the basis of the actual age of the living body, the average life expectancy, and the blood vessel wall damage degree; and
the measurement device, further includes:
a blood vessel visualizing light source for visualizing the blood vessel of the target measurement part by irradiating the target measurement part; and a camera section for capturing the target measurement part irradiated with light of the blood vessel visualizing light source.

8. A measurement result processing method executed by a processor based on measurement data of fluorescence generated by irradiating a target measurement part of a living body with a measurement device, said measurement device including: a light-shielding section for shielding environment light which is directed toward the target measurement part of the living body; an excitation light source for irradiating the target measurement part of the living body with excitation light; and a detector for generating the measurement data by analyzing the fluorescence generated by irradiating the target measurement part with the excitation light, the method comprising:
- (I) extracting a fluorescence characteristic in fluorescence from the measurement data;
- (II) specifying an amount of fluorescent substances contained in the target measurement part on the basis of the fluorescence characteristic extracted in the step (I);
- (III) determining a damage degree indicative of a degree of damage received by the target measurement part or a part of the target measurement part on the basis of the amount of fluorescent substances specified in the step (II);
- (IV) calculating measurement part age indicative of how aging of the target measurement part progresses on the basis of actual age of the living body, an average life expectancy specified based on the actual age, and the damage degree of the target measurement part, the actual age being entered to the processor, the damage degree being determined in the step (III); and storing first correlation information indicative of a correlation between (I) the actual age of the living body, the average life expectancy, and the damage degree, and (II) the measurement part age, the measurement part age calculation step calculating the measurement part age by use of formula as the first correlation information;

Measurement part age=Average life expectancy−(Average life expectancy/Damage degree)+(Actual age-10).

* * * * *